(12) United States Patent
Lee et al.

(10) Patent No.: US 11,385,144 B2
(45) Date of Patent: Jul. 12, 2022

(54) ANTIBODY-PROVIDING KIT, ANTIBODY-CONTAINING PATCH, METHOD AND DEVICE FOR IMMUNOASSAY USING THE SAME

(71) Applicant: NOUL CO., LTD., Gyeonggi-do (KR)

(72) Inventors: Dong Young Lee, Gyeonggi-do (KR); Chan Yang Lim, Gyeonggi-do (KR); Kyung Hwan Kim, Gyeonggi-do (KR)

(73) Assignee: Noul Co., Ltd., Yongin-si (KR)

( * ) Notice: Subject to any disclaimer, the term of this patent is extended or adjusted under 35 U.S.C. 154(b) by 0 days.

(21) Appl. No.: 16/079,451

(22) PCT Filed: Feb. 23, 2017

(86) PCT No.: PCT/KR2017/002028
§ 371 (c)(1),
(2) Date: Aug. 23, 2018

(87) PCT Pub. No.: WO2017/146504
PCT Pub. Date: Aug. 31, 2017

(65) Prior Publication Data
US 2019/0049349 A1 Feb. 14, 2019

Related U.S. Application Data

(60) Provisional application No. 62/298,959, filed on Feb. 23, 2016.

(30) Foreign Application Priority Data

Jun. 4, 2016 (KR) .......................... 10-2016-0069936
Jun. 4, 2016 (KR) .......................... 10-2016-0069937
(Continued)

(51) Int. Cl.
*G01N 1/31* (2006.01)
*G01N 1/30* (2006.01)
(Continued)

(52) U.S. Cl.
CPC ................ *G01N 1/312* (2013.01); *B01L 3/00* (2013.01); *C07K 16/3061* (2013.01);
(Continued)

(58) Field of Classification Search
CPC ........ G01N 1/312; G01N 15/14; G01N 33/49; G01N 33/60
See application file for complete search history.

(56) References Cited

U.S. PATENT DOCUMENTS 555,270 A 2/1896 Taylor
3,870,146 A 3/1975 Greenfield et al.
(Continued)

FOREIGN PATENT DOCUMENTS

CN 1034617 A 8/1989
CN 1207171 A 2/1999
(Continued)

OTHER PUBLICATIONS dictionary.com definition "mesh" accessed Jan. 2020. (Year: 2020).*
(Continued)

*Primary Examiner* — Melanie Brown
(74) *Attorney, Agent, or Firm* — Perkins Coie LLP

(57) ABSTRACT

The present disclosure relates to an immunoassay method for performing immunoassay by using a patch that contains antibodies. An immunoassay method according to an aspect of the present disclosure performs diagnosis by detecting a target protein from a sample to be diagnosed by using a patch which includes a mesh structural body forming micro-cavities and is configured to contain a liquid substance in the micro-cavities, and includes placing the sample to be diagnosed in a reaction region, and providing an antibodies that react specifically with a target protein to the reaction region by using a patch that contains the antibodies.

18 Claims, 84 Drawing Sheets

(30) Foreign Application Priority Data

| | | |
|---|---|---|
| Jun. 4, 2016 | (KR) | 10-2016-0069938 |
| Jul. 27, 2016 | (KR) | 10-2016-0095739 |
| Sep. 13, 2016 | (KR) | 10-2016-0118462 |
| Nov. 1, 2016 | (KR) | 10-2016-0144551 |
| Feb. 23, 2017 | (KR) | 10-2017-0024389 |

(51) Int. Cl.

| | |
|---|---|
| C12Q 1/6844 | (2018.01) |
| C12Q 1/6848 | (2018.01) |
| G01N 33/50 | (2006.01) |
| G01N 21/77 | (2006.01) |
| G01N 33/558 | (2006.01) |
| B01L 3/00 | (2006.01) |
| G01N 15/06 | (2006.01) |
| G01N 33/52 | (2006.01) |
| G01N 33/574 | (2006.01) |
| G01N 15/14 | (2006.01) |
| G01N 33/49 | (2006.01) |
| G01N 33/60 | (2006.01) |
| C12Q 1/686 | (2018.01) |
| C07K 16/30 | (2006.01) |
| C12Q 1/70 | (2006.01) |
| G01N 33/483 | (2006.01) |
| G06T 7/00 | (2017.01) |
| G01N 33/53 | (2006.01) |
| G01N 33/533 | (2006.01) |
| B01L 7/00 | (2006.01) |
| G01N 15/00 | (2006.01) |

(52) U.S. Cl.
CPC ............ *C12Q 1/686* (2013.01); *C12Q 1/6844* (2013.01); *C12Q 1/6848* (2013.01); *C12Q 1/701* (2013.01); *G01N 1/30* (2013.01); *G01N 1/31* (2013.01); *G01N 15/06* (2013.01); *G01N 15/14* (2013.01); *G01N 21/77* (2013.01); *G01N 33/4833* (2013.01); *G01N 33/49* (2013.01); *G01N 33/5082* (2013.01); *G01N 33/52* (2013.01); *G01N 33/533* (2013.01); *G01N 33/5304* (2013.01); *G01N 33/558* (2013.01); *G01N 33/574* (2013.01); *G01N 33/60* (2013.01); *G06T 7/0012* (2013.01); *G06T 7/0014* (2013.01); *B01L 3/505* (2013.01); *B01L 7/52* (2013.01); *G01N 2001/302* (2013.01); *G01N 2015/0065* (2013.01); *G01N 2015/0693* (2013.01); *G01N 2021/7723* (2013.01); *G01N 2021/7786* (2013.01)

(56) References Cited

U.S. PATENT DOCUMENTS

| | | | |
|---|---|---|---|
| 4,250,257 A | | 2/1981 | Lee et al. |
| 4,839,297 A | * | 6/1989 | Freitag ............. G01N 33/525 422/404 |
| 4,938,593 A | | 7/1990 | Morris et al. |
| 5,143,714 A | | 9/1992 | Cosgrove et al. |
| 5,552,270 A | | 9/1996 | Khrapko et al. |
| 5,552,279 A | | 9/1996 | Weisburg et al. |
| 5,776,684 A | | 7/1998 | Chirikjian et al. |
| 5,779,982 A | | 7/1998 | Aota et al. |
| 5,928,879 A | | 7/1999 | Dumler et al. |
| 6,063,029 A | | 5/2000 | Saita et al. |
| 6,174,683 B1 | | 1/2001 | Hahn et al. |
| 7,183,356 B2 | | 2/2007 | Ishida |
| 7,261,800 B1 | | 8/2007 | Nakazato |
| 7,522,757 B2 | | 4/2009 | Tsipouras et al. |
| 7,767,414 B1 | | 8/2010 | Smith et al. |
| 8,293,487 B1 | | 10/2012 | Zhang |
| 8,305,579 B2 | | 11/2012 | Treynor et al. |
| 8,409,849 B2 | | 4/2013 | Yamasaki |
| 8,597,574 B2 | | 12/2013 | Gumbrecht et al. |
| 8,628,787 B2 | | 1/2014 | Soldani et al. |
| 8,809,027 B1 | | 8/2014 | Lynch et al. |
| 8,936,912 B2 | | 1/2015 | Mitra et al. |
| 10,234,447 B2 | | 3/2019 | Manaresi et al. |
| 10,254,286 B2 | | 4/2019 | Pirie-Shepherd et al. |
| 10,345,204 B2 | | 7/2019 | Lee et al. |
| 10,371,610 B2 | | 8/2019 | Lee et al. |
| 11,041,842 B2 | | 6/2021 | Lee et al. |
| 2002/0055126 A1 | * | 5/2002 | Schaffler ............. G01N 33/532 435/7.9 |
| 2003/0083294 A1 | | 5/2003 | Sullenger et al. |
| 2003/0086927 A1 | | 5/2003 | Gordon et al. |
| 2003/0124619 A1 | | 7/2003 | Weigl et al. |
| 2003/0211507 A1 | | 11/2003 | Hatch et al. |
| 2004/0038306 A1 | | 2/2004 | Agnew et al. |
| 2004/0126826 A1 | * | 7/2004 | Yusuf ............. G01N 33/54366 435/7.32 |
| 2004/0175710 A1 | | 9/2004 | Haushalter |
| 2005/0139511 A1 | | 6/2005 | Burns et al. |
| 2005/0175987 A1 | | 8/2005 | Jansen et al. |
| 2005/0175997 A1 | | 8/2005 | Ono et al. |
| 2005/0202567 A1 | | 9/2005 | Zanzucchi et al. |
| 2005/0244976 A1 | | 11/2005 | Gee et al. |
| 2006/0088847 A1 | | 4/2006 | Gu et al. |
| 2006/0111331 A1 | | 5/2006 | Eishingdrelo et al. |
| 2006/0115905 A1 | | 6/2006 | Hatch et al. |
| 2006/0121474 A1 | | 6/2006 | Kim et al. |
| 2006/0172278 A1 | | 8/2006 | Bonner et al. |
| 2007/0051630 A1 | | 3/2007 | Larsson et al. |
| 2007/0087362 A1 | | 4/2007 | Church et al. |
| 2007/0117177 A1 | | 5/2007 | Luo et al. |
| 2007/0128073 A1 | | 6/2007 | Tappen |
| 2007/0224701 A1 | * | 9/2007 | Rosenstein ....... G01N 33/54386 436/514 |
| 2008/0090267 A1 | | 4/2008 | Komatsu et al. |
| 2008/0145934 A1 | * | 6/2008 | Harris ................... A61L 27/52 435/404 |
| 2008/0166745 A1 | * | 7/2008 | Khan ..................... G01N 33/92 435/11 |
| 2008/0182287 A1 | | 7/2008 | Smith et al. |
| 2008/0241890 A1 | | 10/2008 | Gumbrecht et al. |
| 2009/0098165 A1 | | 4/2009 | Arulanandam et al. |
| 2009/0220968 A1 | | 9/2009 | Issadore et al. |
| 2009/0226911 A1 | | 9/2009 | Mauk et al. |
| 2010/0047790 A1 | | 2/2010 | Southern et al. |
| 2010/0168390 A1 | | 7/2010 | Brix et al. |
| 2011/0041978 A1 | | 2/2011 | Wallace et al. |
| 2011/0070606 A1 | | 3/2011 | Winkelman et al. |
| 2011/0257666 A1 | | 10/2011 | Ladet et al. |
| 2012/0040397 A1 | | 2/2012 | Luo et al. |
| 2012/0064041 A1 | | 3/2012 | Alexanian |
| 2012/0070485 A1 | | 3/2012 | Soldani et al. |
| 2012/0171290 A1 | | 7/2012 | Coursaget et al. |
| 2012/0196320 A1 | | 8/2012 | Seibel et al. |
| 2013/0213811 A1 | | 8/2013 | Kennedy et al. |
| 2013/0288273 A1 | | 10/2013 | Takagi et al. |
| 2013/0296761 A1 | | 11/2013 | Goto et al. |
| 2013/0338016 A1 | | 12/2013 | McDonough et al. |
| 2014/0004527 A1 | | 1/2014 | Oka et al. |
| 2014/0038230 A1 | | 2/2014 | Beck et al. |
| 2014/0073063 A1 | * | 3/2014 | Lieber ................. H01L 51/0504 438/1 |
| 2014/0242601 A1 | * | 8/2014 | Belbruno ......... G01N 33/54386 435/7.1 |
| 2014/0273088 A1 | | 9/2014 | Winther |
| 2015/0080252 A1 | | 3/2015 | Godwin et al. |
| 2015/0139511 A1 | | 5/2015 | Yoon et al. |
| 2015/0167073 A1 | | 6/2015 | Romanov et al. |
| 2016/0265028 A1 | | 9/2016 | Kim et al. |
| 2019/0025281 A1 | | 1/2019 | Lee et al. |
| 2019/0048395 A1 | | 2/2019 | Lee et al. |
| 2019/0049426 A1 | | 2/2019 | Lee et al. |
| 2019/0056296 A1 | | 2/2019 | Lee et al. |
| 2019/0056298 A1 | | 2/2019 | Lee et al. |
| 2019/0064140 A1 | | 2/2019 | Lee et al. |

(56) References Cited

U.S. PATENT DOCUMENTS

| | | |
|---|---|---|
| 2019/0316695 A1 | 10/2019 | Feith et al. |
| 2019/0316995 A1 | 10/2019 | Lee et al. |
| 2020/0240882 A1 | 7/2020 | Lee et al. |
| 2020/0249134 A1 | 8/2020 | Lee et al. |
| 2021/0340607 A1 | 11/2021 | Lee et al. |

FOREIGN PATENT DOCUMENTS

| | | |
|---|---|---|
| CN | 1363006 A | 8/2002 |
| CN | 1409110 A | 4/2003 |
| CN | 1561202 A | 1/2005 |
| CN | 1747703 A | 3/2006 |
| CN | 1971276 A | 5/2007 |
| CN | 101004377 A | 7/2007 |
| CN | 101225430 A | 7/2008 |
| CN | 101464237 A | 6/2009 |
| CN | 101598731 A | 12/2009 |
| CN | 101610847 A | 12/2009 |
| CN | 102245305 A | 11/2011 |
| CN | 102245755 A | 11/2011 |
| CN | 102272595 A | 12/2011 |
| CN | 102665917 A | 9/2012 |
| CN | 103038639 A | 4/2013 |
| CN | 103261872 A | 8/2013 |
| CN | 103328651 A | 9/2013 |
| CN | 103800040 A | 5/2014 |
| CN | 103808551 A | 5/2014 |
| CN | 104271191 A | 1/2015 |
| CN | 104349769 A | 2/2015 |
| CN | 104651473 A | 5/2015 |
| CN | 105122034 A | 12/2015 |
| CN | 105136795 A | 12/2015 |
| CN | 105259095 A | 1/2016 |
| EP | 2072993 A2 | 6/2009 |
| EP | 2072993 A3 | 6/2009 |
| EP | 2206462 A1 | 4/2010 |
| EP | 2940474 A1 | 11/2015 |
| JP | S 63-281050 A | 11/1988 |
| JP | H 08-271390 A | 10/1996 |
| JP | S 52-89375 A | 7/1997 |
| JP | 2003344394 A | 12/2003 |
| JP | 2004-077387 A | 3/2004 |
| JP | 2008518662 A | 6/2008 |
| JP | 2008164520 A | 7/2008 |
| JP | 2009518651 A | 5/2009 |
| JP | 2012515931 A | 7/2012 |
| JP | 5198399 B2 | 5/2013 |
| JP | 2013515235 A | 5/2013 |
| JP | 2013515955 A | 5/2013 |
| KR | 10-0601831 B1 | 7/2006 |
| KR | 10-2006-0112258 A | 10/2006 |
| KR | 10-2011-0084636 A | 7/2011 |
| KR | 10-2011-0136782 A | 12/2011 |
| KR | 10-2013-0138153 A | 12/2013 |
| KR | 10-2014-0082757 A | 7/2014 |
| KR | 10-2014-0100580 A | 8/2014 |
| KR | 10-2014-0103350 A | 8/2014 |
| KR | 10-1453796 B1 | 10/2014 |
| KR | 10-2015-0048964 A | 5/2015 |
| KR | 10-1540845 B1 | 7/2015 |
| WO | WO 2000077293 A1 | 12/2000 |
| WO | WO 2002072262 A1 | 3/2002 |
| WO | WO 2002072081 A1 | 9/2002 |
| WO | WO 2004024955 A1 | 3/2004 |
| WO | WO 2004071469 A2 | 8/2004 |
| WO | WO 2004071469 A3 | 8/2004 |
| WO | WO 2006050032 A2 | 5/2006 |
| WO | WO 2006050032 A3 | 5/2006 |
| WO | WO 2006053770 A1 | 5/2006 |
| WO | WO 2006108087 A2 | 10/2006 |
| WO | WO 2006108087 A3 | 10/2006 |
| WO | WO 2007067847 A2 | 6/2007 |
| WO | WO 2007067847 A3 | 6/2007 |
| WO | WO 2008075086 A1 | 6/2008 |
| WO | WO 2010039627 A2 | 4/2010 |
| WO | WO 2010039627 A3 | 4/2010 |
| WO | WO 2010041088 A1 | 4/2010 |
| WO | WO 2010052543 A1 | 5/2010 |
| WO | WO 2010052543 A8 | 5/2010 |
| WO | 2010/081393 * | 7/2010 |
| WO | WO 2010082820 A2 | 7/2010 |
| WO | WO 2010082820 A3 | 7/2010 |
| WO | WO 2011066449 A1 | 6/2011 |
| WO | WO 2011076705 A1 | 6/2011 |
| WO | WO 2011080539 A1 | 7/2011 |
| WO | WO 2011143075 A2 | 11/2011 |
| WO | WO 2011143075 A3 | 11/2011 |
| WO | WO 2012003579 A1 | 1/2012 |
| WO | WO 2012030313 A1 | 3/2012 |
| WO | WO 2012048154 A1 | 4/2012 |
| WO | WO 2012072980 A1 | 6/2012 |
| WO | WO 2012137506 A1 | 10/2012 |
| WO | WO 2013095896 A1 | 12/2012 |
| WO | WO 2013086015 A1 | 6/2013 |
| WO | WO 2013103712 A1 | 7/2013 |
| WO | WO 2013111054 A1 | 8/2013 |
| WO | WO 2013169924 A1 | 11/2013 |
| WO | WO 2014041093 A1 | 3/2014 |
| WO | WO 2014146062 A2 | 9/2014 |
| WO | WO 2014146062 A3 | 9/2014 |
| WO | WO 2015137595 A1 | 9/2015 |
| WO | WO 2017048871 A1 | 3/2017 |

OTHER PUBLICATIONS

Beck, M., et al., "On-chip sample preparation by controlled release of antibodies for simple CD4 counting", Lab Chip, 2012, 12, 167, 7 pages.

Deiss et al., 2014, "Antimicrobial susceptibility assays in paper-based portable culture devices," Lab on a Chip, 14(1):167-171.

English translation of the International Search Report and Written Opinion dated Jul. 6, 2017 of PCT Application No. PCT/KR2017/002028 (published as WO 2017/146504) (9 pages).

English translation of the International Search Report and Written Opinion dated May 29, 2017 of PCT Application No. PCT/KR2017/002026 (published as WO 2017/146502) (7 pages).

English translation of the International Search Report and Written Opinion dated May 29, 2017 of PCT Application No. PCT/KR2017/002027 (published as WO 2017/146503) (8 pages).

English translation of the International Search Report and Written Opinion dated May 29, 2017 of PCT Application No. PCT/KR2017/002029 (published as WO 2017/146505) (9 pages).

English translation of the International Search Report and Written Opinion dated May 29, 2017 of PCT Application No. PCT/KR2017/002030 (published as WO 2017/146506) (9 pages).

English translation of the International Search Report and Written Opinion dated May 29, 2017 of PCT Application No. PCT/KR2017/002031 (published as WO 2017/146507) (12 pages).

English translation of the International Search Report and Written Opinion dated May 29, 2017 of PCT Application No. PCT/KR2017/002032 (published as WO 2017/146508) (11 pages).

Horibata et al., 2015, "Utilization of the Soft Agar Colony Formation Assay to Identify Inhibitors of Tumorigenicity in Breast Cancer Cells," J Vis Exp., (99):e52727 (7 pages).

Hudzicki, 2009, "Kirby-Bauer Disk Diffusion Susceptibility Test Protocol," American Society for Microbiology, retreived from the internet: https://www.asm.org/getattachment/2594ce26-bd44-47f6-8287-0657aa9185ad/kirby-bauer-disk-diffusion-susceptibility-test-protocol-pdf.pdf, retreived on Jul. 23, 2019 (23 pages).

Matsuo et al., 2001, "A simple method for classification of cell death by use of thin layer collagen gel for the detection of apoptosis and/or necrosis after cancer chemotherapy," Jpn J Cancer Res., 92(7):813-819.

Notodihardjo et al., 2015, "Gelatin hydrogel impregnated with platelet-rich plasma releasate promotes angiogenesis and wound healing in murine model," J Artif Organs., 18(1):64-71.

Oss-Ronen et al., 2011, "Polymer-conjugated albumin and fibrinogen composite hydrogels as cell scaffolds designed for affinity-based drug delivery," Acta Biomater, 7(1):163-170.

(56) References Cited

OTHER PUBLICATIONS

Wakayama et al., 2013, "Design of a single-step immunoassay principle based on the combination of an enzyme-labeled antibody release coating and a hydrogel copolymerized with a fluorescent enzyme substrate in a microfluidic capillary device," Lab Chip, 13(22):4304-4307.

Wu et al., 2008, "Disposable reagentless electrochemical immunosensor array based on a biopolymer/sol-gel membrane for simultaneous measurement of several tumor markers," Clin Chem., 54(9):1481-1488.

Becton, Dickinson and Company, 2013, "BD™ EMB Agar (Eosin Methylene Blue Agar), Modified Intended Use," retreived from the internet: URL: https://legacy.bd.com/RESOURCE.ASPX?IDX=8973 [retreived on Apr. 2, 2020] (3 pages).

Cardinal Health, 2013, "Histology vol. II: Laboratory products for your Histology needs," retrived from the Internet: URL:http://www.henryschein.com/assets/medical/2883001.pdf [retreived on Apr. 2, 2020] (95 pages).

Geckil et al., 2010, "Engineering hydrogels as extracellular matrix mimics," Nanomedicine (Lond), 5(3):469-484.

Liu et al., 2009, "Aptamer-nanoparticle strip biosensor for sensitive detection of cancer cells," Anal Chem., 81(24):10013-10018.

Massart et al., 2009, "Striatal GPR88 expression is confined to the whole projection neuron population and is regulated by dopaminergic and glutamatergic afferents," Eur J Neurosci., 30(3):397-414.

Punyani et al., 2006, "Sustained release of iodine from a polymeric hydrogel device for water disinfection," Journal of Applied Polymer Science, 103(5):3334-3340.

Rand, 1996, "Crystal violet can be used to visualize DNA bands during gel electrophoresis and to improve cloning efficiency," Technical Tips Online, 1:23-24.

Romano et al., 2015, "Controlled antiseptic/eosin release from chitosan-based hydrogel modified fibrous substrates," Carbohydr Polym., 131:306-314.

Zhu et al., 2015, "Microbiology Experiment and Learning Guide—Experiment 6 In Vitro Antibacterial Test of Drug," Fourth Force Medical University Press, pp. 24-26 (in Chinese with English translation), 11 pages.

Zustiak et al., 2010, "Solute diffusion and interactions in cross-linked poly(ethylene glycol) hydrogels studied by Fluorescence Correlation Spectroscopy," Soft Matter, 6(15):3609-3618.

Man et al., 2011, "Currently Used Markers for CTC Isolation—Advantages, Limitations and Impact on Cancer Prognosis," J Clinic Experiment Pathol, 1:1 (7 pages).

\* cited by examiner

ANTIBODY-PROVIDING KIT, ANTIBODY-CONTAINING PATCH, METHOD AND DEVICE FOR IMMUNOASSAY USING THE SAME

CROSS-REFERENCES TO RELATED APPLICATIONS

This application is a U.S. national phase application, pursuant to 35 U.S.C. § 371, of PCT/KR2017/002028, filed Feb. 23, 2017, designating the United States, which claims the benefit of U.S. Provisional Application No. 62/298,959, filed Feb. 23, 2016, and claims priority to Korean Application No. 10-2016-0069936, filed Jun. 4, 2016, to Korean Application No. 10-2016-0069937, filed Jun. 4, 2016, to Korean Application No. 10-2016-0069938, filed Jun. 4, 2016, to Korean Application No. 10-2016-0095739, filed Jul. 27, 2016, to Korean Application No. 10-2016-0118462, filed Sep. 13, 2016, to Korean Application No. 10-2016-0144551, filed Nov. 1, 2016, and to Korean Application No. 10-2017-0024389, filed Feb. 23, 2017. The entire contents of the aforementioned patent applications are incorporated herein by this reference.

TECHNICAL FIELD

The present disclosure relates to an antibody-containing patch, a method of and device for immunoassay using the same, and more particularly, to a patch that contains an antibody and a method and device for performing immunoassay using the same for economically performing diagnosis using an immunological characteristic from a sample and promptly acquiring a result.

BACKGROUND ART

Due to a rapidly aging society and increasing need for quality of life, the diagnostic market which aims at early diagnosis and early treatment is growing every year in the world, including South Korea, and quick and easy diagnosis is becoming an important issue. In particular, forms of diagnosis are being transitioned into forms in which diagnosis can be performed without using large diagnostic equipment, such as in-vitro diagnosis (IVD) or point-of-care testing (POCT) which is immediately performed next to a patient. Immunochemical diagnosis, which is one specific diagnostic field for performing IVD, is one diagnostic method that accounts for a large portion in the IVD field and is widely used.

Immunochemical diagnosis, which is a collective term for diagnosis through clinical immunoassay and diagnosis through chemical analysis, uses an antigen-antibody reaction, and is used in diagnosing various diseases and monitoring tumor markers, allergies, and the like. Due to a variety of diseases that are detectable by immunochemical diagnosis and ease of detection thereby, immunochemical diagnosis is evaluated as a form of diagnosis that is particularly suitable for POCT. Demand for such immunochemical diagnosis has been steadily increasing worldwide, and the increasing trend is particularly noticeable in China.

In a conventional immunoassay method, in a process in which an antibody is applied to a specimen to detect an antigen that causes a disease which is desired to be diagnosed, a washing process in which a large amount of washing solution is poured to rinse a plate or the like in order to remove unbound antibodies or other factors that interfere with the detection is necessarily required. In this case, there is a problem that a large amount of washing solution is wasted. Also, the conventional immunoassay method has disadvantages in that separate effort is required for designing a region on which an antibody is applied to increase an effective contact surface area between a fixated antibody and an applied antigen, and the complexly-designed region also affects detection of a reaction.

Accordingly, a means for effectively removing factors that interfere with detection while minimizing an amount of solution required for diagnosis is needed. Also, provision of a reaction space that facilitates performance of diagnosis and allows a result to be easily detected is needed.

SUMMARY

An aspect of the present disclosure is to provide a patch capable of storing a substance.

An aspect of the present disclosure is to provide a patch capable of providing a reaction space for a substance.

An aspect of the present disclosure is to provide a patch capable of providing a substance.

An aspect of the present disclosure is to provide a patch capable of absorbing a substance.

An aspect of the present disclosure is to provide a patch capable of providing an environment.

An aspect of the present disclosure is to provide a patch that contains an antibody.

An aspect of the present disclosure is to provide an immunoassay method using a patch.

According to an aspect of the present disclosure, there is provided an immunoassay device for performing diagnosis by detecting a target protein from a sample to be diagnosed by using a patch which includes a mesh structural body forming micro-cavities and is configured to contain a liquid substance in the micro-cavities, the immunoassay device including a plate supporter configured to support a plate on which a reaction region is placed and a sample to be diagnosed is placed in the reaction region, a patch controller configured to use the patch, which is configured to contain antibodies that react specifically with a target protein, and control a position of the patch relative to the reaction region so that the antibodies are provided to the reaction region, and a reaction detector configured to detect a specific reaction between the antibodies and the target protein to diagnose a target disease.

According to another aspect of the present disclosure, there is provided an antibody-containing patch including antibodies that react specifically with a target protein, and a mesh structural body provided in a mesh structure forming micro-cavities in which the antibodies are contained that is configured to come into contact with a reaction region in which the target protein is placed and provide some of the contained antibodies to the reaction region.

The antibodies that react specifically with the target protein may be primary antibodies which specifically bind to a target antigen.

The antibodies that react specifically with the target protein may be secondary antibodies which specifically bind to antibodies which specifically bind to a target antigen.

The target protein may be an antigen, the antibodies may be a pair of antibodies formed by binding between a primary antibody which specifically binds to the antigen and a secondary antibody which specifically binds to the primary antibody, and the pair of antibodies may react specifically with the antigen.

Multiple target proteins may be present, the multiple target proteins may include a first target protein and a second target protein, and the antibodies may include a first antibody that reacts specifically with the first target protein and a second antibody that reacts specifically with the second target protein.

According to yet another aspect of the present disclosure, there is provided a patch cluster that includes a plurality of antibody-containing patches, wherein the antibody-containing patch includes antibodies that react specifically with a target protein and a mesh structural body that forms micro-cavities in which the antibodies are contained.

The plurality of antibody-containing patches may include a first antibody-containing patch and a second antibody-containing patch, and a target protein with which a first antibody contained in the first antibody-containing patch reacts specifically may be different from a target protein with which a second antibody contained in the second antibody-containing patch reacts specifically.

According to still another aspect of the present disclosure, there is provided a substrate-containing patch including substrates that produce a product through a chemical reaction that is catalyzed by an enzyme attached to an antibody that binds specifically to a target protein, and a mesh structural body provided in a mesh structure forming micro-cavities in which the substrates are contained that is configured to come into contact with a reaction region in which the target protein is placed and provide some of the contained substrates to the reaction region.

According to still another aspect of the present disclosure, there is provided an immunoassay method of performing diagnosis by detecting a target protein from a sample to be diagnosed by using a patch which includes a mesh structural body forming micro-cavities and is configured to contain a liquid substance in the micro-cavities, the immunoassay method including placing the sample to be diagnosed in a reaction region, and providing antibodies that react specifically with a target protein to the reaction region by using a patch that contains the antibodies.

The immunoassay method may further include providing a substrate, which produces a product through a chemical reaction catalyzed by an enzyme attached to the antibodies, to the reaction region by using a patch that contains the substrate. The immunoassay method may further include detecting a specific reaction between the antibodies and the target protein to diagnose a target disease.

In this case, the detecting of the specific reaction may include detecting the specific reaction by measuring a change in an electrical characteristic of the patch that occurs due to the specific reaction.

The detecting of the specific reaction may be performed by at least any one of measuring fluorescence that occurs due to a chemical reaction catalyzed by an enzyme attached to the antibodies that bind specifically to the target protein, measuring luminescence that occurs due to the chemical reaction, and measuring color that develops due to the chemical reaction.

The placing of the sample to be diagnosed may be performed by any one of a method of fixating the sample to the plate, a method of smearing the sample on the plate, and a method of smearing the sample on the plate and fixating the sample.

The providing of the antibodies to the reaction region by using the patch may include contacting the patch with the reaction region so that the antibodies are movable to the reaction region, and separating the patch from the reaction region, wherein when the patch is separated from the reaction region, antibodies that have not reacted specifically with the target protein from among the antibodies may be removed from the reaction region.

The immunoassay method may further include absorbing antibodies that have not reacted specifically with the target protein from among the provided antibodies from the reaction region by using a washing patch.

The providing of the antibodies to the reaction region by using the patch may include using a first patch that contains a first antibody that reacts specifically with the target protein to provide the first antibody to the reaction region, and using a second patch that contains a second antibody that reacts specifically with the first antibody to provide the second antibody to the reaction region.

In the immunoassay method, the reaction region may be located on a plate, and the immunoassay method may further include, prior to the placing of the sample to be diagnosed in the reaction region, providing the plate on which bottom antibodies, which are antibodies that react specifically with the target protein, are fixated on the reaction region, and the placing of the sample to be diagnosed in the reaction region may include placing the sample to be diagnosed in the reaction region on which the bottom antibodies are fixated In the immunoassay method, multiple target proteins may be present, the multiple target proteins may include a first target protein and a second target protein, and the patch may contain a first antibody that reacts specifically with the first target protein and a first antibody that react specifically with the second target protein.

In the immunoassay method, multiple target proteins may be present, a plurality of patches that contain the antibodies may be present, the multiple target proteins may include a first target protein and a second target protein, and the plurality of patches may include a first patch that contains a first antibody that reacts specifically with the first target protein and a second patch that contains a second antibody that reacts specifically with the second target protein.

According to still another aspect of the present disclosure, there is provided an immunoassay method for performing diagnosis by detecting a target protein from a sample to be diagnosed by using a patch which includes a mesh structural body forming micro-cavities and is configured to contain a liquid substance in the micro-cavities, the immunoassay method including placing the sample to be diagnosed in a reaction region, using a patch that contains a first antibody that reacts specifically with a first target protein to provide the first antibody to the reaction region, and using a patch that contains a second antibody that reacts specifically with a second target protein to provide the second antibody to the reaction region.

In the above embodiment, the immunoassay method may further include, after the providing of the second antibody, detecting the first target protein and the second target protein.

In this case, the detecting of the first target protein may include detecting first fluorescence that is detected from a fluorescence label attached to the first antibody bound specifically to the first target protein, and the detecting of the second target protein may include detecting second fluorescence that is detected from a fluorescence label attached to the second antibody bound specifically to the second target protein. Here, a wavelength band from which the first fluorescence is detected and a wavelength band from which the second fluorescence is detected may be different from each other.

In the above embodiment, the immunoassay method may further include, after the providing of the first antibody to the reaction region, detecting the first target protein, and after the providing of the second antibody to the reaction region, detecting the second target protein.

In this case, the detecting of the first target protein may include detecting first fluorescence that is detected from a fluorescence label attached to the first antibody bound specifically to the first target protein, and the detecting of the second target protein may include detecting second fluorescence that is detected from a fluorescence label attached to the second antibody bound specifically to the second target protein.

Here, a wavelength band from which the first fluorescence is detected may overlap at least a portion of a wavelength band from which the second fluorescence is detected, and the detecting of the second fluorescence may be performed by comparing fluorescence detected from the sample after the second antibody is provided to the reaction region and fluorescence detected from the sample before the second antibody is provided to the reaction region.

According to still another aspect of the present disclosure, there is provided an antibody providing kit that includes a medium which contains antibodies that react specifically with a target protein, and an antibody providing patch which includes a mesh structural body forming micro-cavities and is configured to come into contact with the medium to absorb some of the antibodies contained in the medium and come into contact with a reaction region in which the target protein is placed to provide at least some of the absorbed antibodies to the reaction region.

According to still another aspect of the present disclosure, there is provided an immunoassay method for performing diagnosis by detecting a target protein from a sample to be diagnosed by using a patch which includes a mesh structural body forming micro-cavities and is configured to handle a liquid substance in the micro-cavities, the immunoassay method including contacting a medium, which contains antibodies that react specifically with the target protein, with the patch, and contacting the patch with a reaction region in which the target protein is placed, wherein, when the medium is brought into contact with the patch, at least some of the antibodies contained in the medium are absorbed into the patch. In this case, when the patch is brought into contact with the reaction region, at least some of the antibodies absorbed into the patch may be movable to the reaction region.

The contacting of the medium with the patch may include contacting a surface of the medium with the patch, and the contacting of the patch with the reaction region may include contacting a surface of the patch, which is not with the medium, into contact with the reaction region.

Solutions for solving the technical problems of the present disclosure are not limited to the above-described solutions, and other unmentioned solution should be clearly understood by those of ordinary skill in the art to which the present disclosure pertains from the present specification and the accompanying drawings.

According to the present disclosure, containing, providing, and absorption of a substance can be easily performed.

According to the present disclosure, a reaction region for a substance can be provided or a predetermined environment can be provided to a target region.

According to the present disclosure, immunoassay can be more conveniently performed, and a diagnosis result can be promptly obtained.

According to the present disclosure, a diagnosis result with sufficient validity can be obtained using a small amount of sample.

According to the present disclosure, providing and absorption of a substance can be suitably adjusted using a path, and an amount of a solution required for diagnosis can be significantly reduced.

According to the present disclosure, diagnosis can be performed by simultaneously detecting a plurality of targets, and patient-specific diagnosis can be performed as a result.

Advantageous effects of the present disclosure are not limited to those mentioned above, and unmentioned advantageous effects should be clearly understood by those of ordinary skill in the art to which the present disclosure pertains from the present specification and the accompanying drawings.

DETAILED DESCRIPTION

Figure 1:
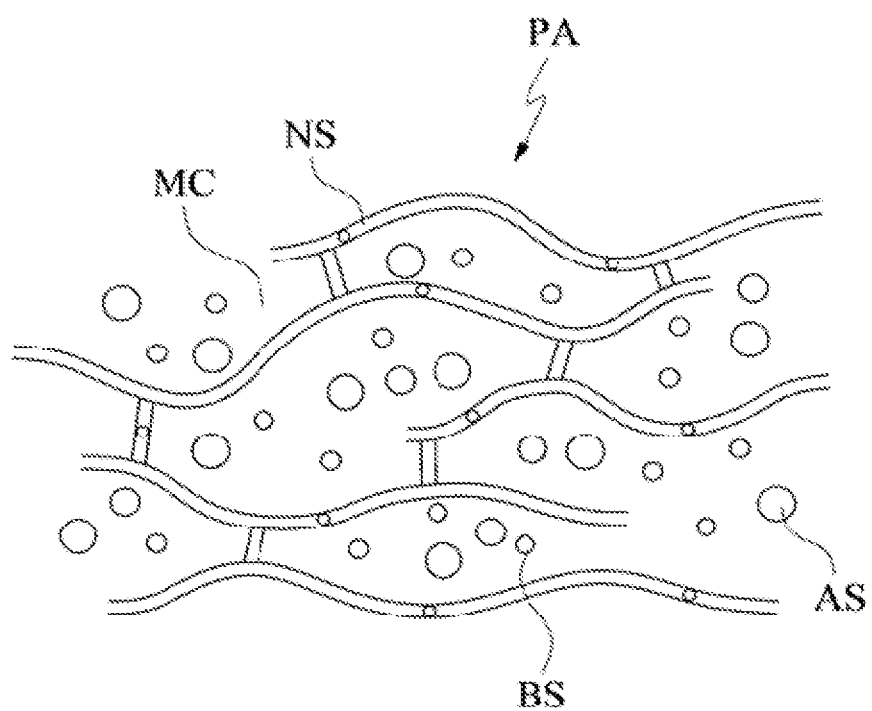
FIG. 1 illustrates an example of a patch in detail according to the present application.

Since embodiments described herein are for clearly describing the spirit of the present disclosure to those of ordinary skill in the art to which the present disclosure pertains, the present disclosure is not limited to the embodiments described herein, and the scope of the present disclosure should be construed as including revised examples or modified examples not departing from the spirit of the present disclosure.

General terms currently being used as widely as possible have been selected as terms used herein in consideration of functions in the present disclosure, but the terms may be changed according to intentions and practices of those of ordinary skill in the art to which the present disclosure pertains or the advent of new technologies, etc. However, instead, when a particular term is defined as a certain meaning and used, the meaning of the term will be separately described. Consequently, the terms used herein should be construed on the basis of substantial meanings of the terms and content throughout the present specification instead of simply on the basis of names of the terms.

The accompanying drawings herein are for easily describing the present disclosure. Since shapes illustrated in the drawings may have been exaggeratedly depicted as much as necessary to assist in understating the present disclosure, the present disclosure is not limited by the drawings.

When detailed description of a known configuration or function related to the present disclosure is deemed to obscure the gist of the present disclosure in the present specification, the detailed description related thereto will be omitted as necessary.

1. Patch 1.1 Meaning of Patch

In the present application, a patch for managing a liquid substance is disclosed.

The liquid substance may mean a substance which is in a liquid state and can flow.

The liquid substance may be a substance formed of a single component having fluidity. Alternatively, the liquid substance may be a mixture that includes a substance formed of a plurality of components.

When the liquid substance is a substance formed of a single component, the liquid substance may be a substance formed of a single chemical element or a compound including a plurality of chemical elements.

When the liquid substance is a mixture, a portion of the substance formed of a plurality of components may serve as a solvent, and the other portion may serve as a solute. That is, the mixture may be a solution.

A plurality of components constituting the mixture which forms the substance may be uniformly distributed. Alternatively, the mixture including the substance formed of a plurality of components may be a uniformly mixed mixture.

The substance formed of a plurality of components may include a solvent and a substance that is not dissolved in the solvent and is uniformly distributed.

A portion of the substance formed of a plurality of components may be non-uniformly distributed. The non-uniformly distributed substance may include non-uniformly distributed particle components in the solvent. In this case, the non-uniformly distributed particle components may be in a solid phase.

For example, a substance that may be managed using the patch may be in a state of 1) a liquid formed of a single component, 2) a solution, or 3) a colloid, or according to circumstances, may be in a state in which 4) solid particles are non-uniformly distributed within another liquid substance.

Hereinafter, the patch according to the present application will be described in more detail.

1.2 General Nature of Patch 1.2.1 Configuration

Figure 2:
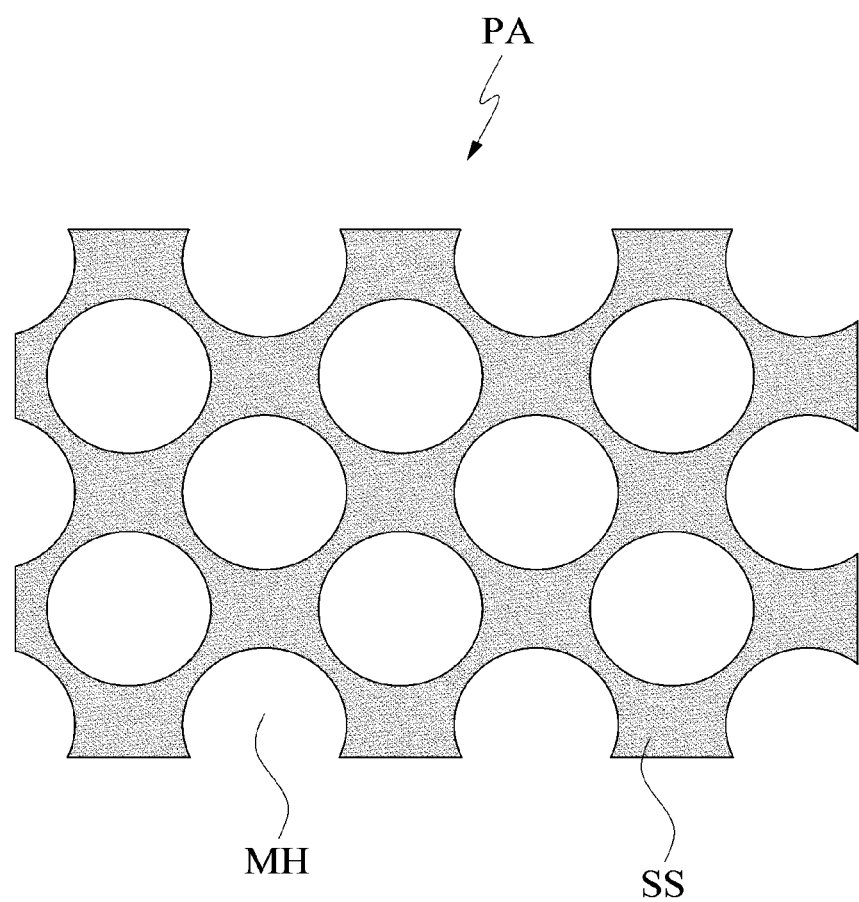
FIG. 2 illustrates an example of a patch in detail according to the present application.

FIGS. 1 and 2 are views illustrating an example of a patch according to the present application. The patch according to the present application will be described below with reference to FIGS. 1 and 2.

Referring to FIG. 1, a patch PA according to the present application may include a mesh structural body NS and a liquid substance.

As the liquid substance, a base substance BS and an additive substance AS may be taken into consideration separately.

The patch PA may be in a gel state (gel type). The patch PA may be implemented as a gel-type structural body in which colloidal molecules are bound and mesh tissues are formed.

The patch PA according to the present application is a structure for managing a liquid substance SB, and may include a three-dimensional mesh (net-like) structural body NS. The mesh structural body NS may be a continuously distributed solid structure. The mesh structural body NS may have a mesh structure in which a plurality of micro-threads are intertwined. However, the mesh structural body NS is not limited to the mesh form in which the plurality of micro-threads are intertwined, and may also be implemented in the form of an arbitrary three-dimensional matrix that is formed by connection of a plurality of micro-structures. For example, the mesh structural body NS may be a frame structural body that includes a plurality of micro-cavities. In other words, the mesh structural body NS may form a plurality of micro-cavities MC.

FIG. 2 illustrates a structure of a patch according to an embodiment of the present application. Referring to FIG. 2, the mesh structural body of the patch PA may have a sponge structure SS. The mesh structural body of the sponge structure SS may include a plurality of micro-holes MH. Hereinafter, the terms micro-holes MH and the micro-cavities MC may be used interchangeably, and unless particularly mentioned otherwise, the term micro-cavities MC is defined as encompassing the concept of the micro-holes MH.

The mesh structural body NS may have a regular or irregular pattern. Furthermore, the mesh structural body NS may include both a region having a regular pattern and a region having an irregular pattern.

A density of the mesh structural body NS may have a value within a predetermined range. Preferably, the predetermined range may be set within a limit in which the form of the liquid substance SB captured in the patch PA is maintained in a form that corresponds to the patch PA. The density may be defined as a degree to which the mesh structural body NS is dense or a mass ratio, a volume ratio, or the like that the mesh structural body NS occupies in the patch.

The patch according to the present application may manage the liquid substance SB by having a three-dimensional mesh structure.

The patch PA according to the present application may include the liquid substance SB, and the fluidity of the liquid substance SB included in the patch PA may be limited by the form of the mesh structural body NS of the patch PA.

The liquid substance SB may freely flow within the mesh structural body NS. In other words, the liquid substance SB is placed in the plurality of micro-cavities formed by the mesh structural body NS. An exchange of liquid substance SB may occur between neighboring micro-cavities. In this case, the liquid substance SB may be present in a state in which the liquid substance SB permeating into a frame structural body that forms the mesh tissues. In such a case, nano-sized pores into which the liquid substances SB may permeate may be formed in the frame structural body.

Further, whether to the liquid substance SB is filled in the frame structural body of the mesh structure may be determined depending on a molecular weight or a particle size of the liquid substance SB to be captured in the patch PA. A substance having a relatively large molecular weight may be captured in the micro-cavities, and a substance having a relatively small molecular weight may be captured by the frame structural body and filled in the micro-cavities and/or the frame structural body of the mesh structural body NS.

In the present specification, the term "capture" may be defined as a state in which the liquid substance SB is placed in the plurality of micro-cavities and/or nano-sized holes formed by the mesh structural body NS. As described above, the state in which the liquid substance SB is captured in the patch PA is defined as including a state in which the liquid substance SB may flow between the micro-cavities and/or the nano-sized holes.

As in the following, the base substance BS and the additive substance AS may be taken into consideration separately as the liquid substance SB.

The base substance BS may be a liquid substance SB having fluidity.

The additive substance AS may be a substance that is mixed with the base substance BS and has fluidity. In other words, the base substance BS may be a solvent. The additive substance AS may be a solute that is dissolved in the solvent or may be particles that are not melted in the solvent.

The base substance BS may be a substance capable of flowing inside a matrix formed by the mesh structural body NS. The base substance BS may be uniformly distributed in the mesh structural body NS or may be distributed only in a partial region of the mesh structural body NS. The base substance BS may be a liquid having a single component.

The additive substance AS may be a substance that is mixed with the base substance BS or dissolved in the base substance BS. For example, the additive substance AS may serve as a solute while the base substance BS is a solvent. The additive substance AS may be uniformly distributed in the base substance BS.

The additive substance AS may be fine particles that are not dissolved in the base substance BS. For example, the additive substance AS may include colloidal molecules and fine particles such as microorganisms.

The additive substance AS may include particles larger than the micro-cavities formed by the mesh structural body NS. When the size of the micro-cavities is smaller than the size of the particles included in the additive substance AS, fluidity of the additive substance AS may be limited.

According to an embodiment, the additive substance AS may include a component that is selectively included in the patch PA.

The additive substance AS does not necessarily refer to a substance that is lower in quantity or inferior in function in comparison to the above-described base substance BS.

Hereinafter, characteristics of the liquid substance SB captured in the patch PA may be presumed as characteristics of the patch PA. That is, the characteristics of the patch PA may depend on characteristics of a substance captured in the patch PA.

1.2.2 Characteristics

As described above, the patch PA according to the present application may include the mesh structural body NS. The patch PA may manage the liquid substance SB through the mesh structural body NS. The patch PA may allow the liquid substance SB captured in the patch PA to maintain at least some of its unique characteristics.

For example, diffusion of a substance may occur in a region of the patch PA in which the liquid substance SB is distributed, and a force such as surface tension may come into action.

The patch PA may provide a liquid environment in which diffusion of a target substance is caused due to thermal motion of a substance or a difference in density or concentration thereof. Generally, "diffusion" refers to a phenomenon in which particles that constitute a substance are spread from a side at which concentration is high to a side at which a concentration is low due to a difference in concentration. Such a diffusion phenomenon may be basically understood as a phenomenon that occurs due to motion of molecules (translational motion in a gas or liquid, vibrational motion in a solid, and the like). In the present application, in addition to referring to the phenomenon in which particles are spread from a side at which a concentration is high toward a side at which a concentration is low due to a difference in concentration or density, "diffusion" also refers to a phenomenon in which particles move due to irregular motion of molecules that occurs even when a concentration is uniform. The expression "irregular motion" may also have the same meaning as "diffusion" unless particularly mentioned otherwise. The diffused substance may be a solute that is dissolved in the liquid substance SB, and the diffused substance may be provided in a solid, liquid, or gas state.

More specifically, a non-uniformly-distributed substance in the liquid substance SB captured by the patch PA may be diffused in a space provided by the patch PA. In other words, the additive substance AS may be diffused in a space defined by the patch PA.

The non-uniformly-distributed substance or the additive substance AS in the liquid substance SB managed by the patch PA may be diffused within the micro-cavities provided by the mesh structural body NS of the patch PA. A region in which the non-uniformly-distributed substance or the additive substance AS may be diffused may be changed by the patch PA being connected or coming into contact with another substance.

Even when, after the concentration of the substance or the additive substance AS has become uniform, as a result of diffusion of the non-uniformly-distributed substance or the additive substance AS within the patch PA or within an external region connected to the patch PA, the substance or the additive substance AS may continuously move due to irregular motion of molecules inside the patch PA and/or within the external region connected to the patch PA.

The patch PA may be implemented to exhibit a hydrophilic or hydrophobic property. In other words, the mesh structural body NS of the patch PA may have a hydrophilic or hydrophobic property.

When properties of the mesh structural body NS and the liquid substance SB are similar, the mesh structural body NS may be able to manage the liquid substance SB more effectively.

The base substance BS may be a polar hydrophilic substance or a nonpolar hydrophobic substance. The additive substance AS may exhibit a hydrophilic or hydrophobic property.

The properties of the liquid substance SB may be related to the base substance BS and/or the additive substance AS. For example, when both the base substance BS and the additive substance AS are hydrophilic, the liquid substance SB may be hydrophilic, and when both the base substance BS and the additive substance AS are hydrophobic, the liquid substance SB may be hydrophobic. When polarities of the base substance BS and the additive substance AS are different, the liquid substance SB may be hydrophilic or hydrophobic.

When polarities of both the mesh structural body NS and the liquid substance SB are hydrophilic or hydrophobic, an attractive force may come into action between the mesh structural body NS and the liquid substance SB. When polarities of the mesh structural body NS and the liquid substance SB are opposite, e.g., when the polarity of the mesh structural body NS is hydrophobic and the polarity of the liquid substance SB is hydrophilic, a repulsive force may act between the mesh structural body NS and the liquid substance SB.

On the basis of the above-described properties, the patch PA may be solely used, a plurality of patches PA may be used, or the patch PA may be used with another medium to induce a desired reaction. Hereinafter, functional aspects of the patch PA will be described.

However, hereinafter, for convenience of description, the patch PA is assumed as being a gel type that may include a hydrophilic solution. In other words, unless particularly mentioned otherwise, the mesh structural body NS of the patch PA is assumed to have a hydrophilic property.

However, the scope of the present application should not be interpreted as being limited to the gel-type patch PA having a hydrophilic property. In addition to a gel-type patch PA that includes a solution exhibiting a hydrophobic property, a gel-type patch PA from which a solvent is removed and even a sol-type patch PA, as long as it is capable of implementing functions according to the present application, may belong to the scope of the present application.

2. Functions of Patch

Due to the above-described characteristics, the patch according to the present application may have some useful functions. In other words, by capturing the liquid substance SB, the patch may become involved in behavior of the liquid substance SB.

Accordingly, hereinafter, in accordance with forms of behavior of the substance with respect to the patch PA, a reservoir function in which a state of the substance is defined in a predetermined region formed by the patch PA and a channeling function in which a state of the substance is defined in a region including an external region of the patch PA will be separately described.

2.1 Reservoir 2.1.1 Meaning

As described above, the patch PA according to the present application may capture the liquid substance SB. In other words, the patch PA may perform a function as a reservoir.

The patch PA may capture the liquid substance SB in the plurality of micro-cavities formed in the mesh structural body NS using the mesh structural body NS. The liquid substance SB may occupy at least a portion of the fine micro-cavities formed by the three-dimensional mesh structural body NS of the patch PA or be penetrated in the nano-sized pores formed in the mesh structural body NS.

The liquid substance SB placed in the patch PA does not lose properties of a liquid even when the liquid substance SB is distributed in the plurality of micro-cavities. That is, the liquid substance SB has fluidity even in the patch PA, and diffusion of a substance may occur in the liquid substance SB distributed in the patch PA, and an appropriate solute may be dissolved in the substance.

The reservoir function of the patch PA will be described below in more detail.

2.1.2 Containing

In the present application, the patch PA may capture a target substance due to the above-described characteristics. The patch PA may have resistance to a change in an external environment within a predetermined range. In this way, the patch PA may maintain a state in which the substance is captured therein. The liquid substance SB, which is a target to be captured, may occupy the three-dimensional mesh structural body NS.

Hereinafter, for convenience, the above-described function of the patch PA will be referred to as "containing."

However, "the patch PA containing the liquid substance" is defined to encompass a case in which the liquid substance is contained in a space formed by the mesh structure and/or a case in which the liquid substance is contained in the frame structural body constituting the mesh structural body NS.

The patch PA may contain the liquid substance SB. For example, the patch PA may contain the liquid substance SB, due to an attractive force that acts between the mesh structural body NS of the patch PA and the liquid substance SB. The liquid substance SB may be bound to the mesh structural body NS with an attractive force of a predetermined strength or higher and contained in the patch PA.

Properties of the liquid substance SB contained in the patch PA may be classified in accordance with properties of the patch PA. More specifically, when the patch PA exhibits a hydrophilic property, the patch PA may be bound to a hydrophilic liquid substance SB which is polar in general and contain the hydrophilic liquid substance SB in the three-dimensional micro-cavities. Alternatively, when the patch PA exhibits a hydrophobic property, the hydrophobic liquid substance SB may be contained in the micro-cavities of the three-dimensional mesh structural body NS.

The amount of substance that may be contained in the patch PA may be proportional to a volume of the patch PA. In other words, the amount of substance contained in the patch PA may be proportional to an amount of three-dimensional mesh structural body NS that serves as a support body that contributes to the form of the patch PA. However, there is no constant proportional factor between the amount of substance that may be contained in the patch PA and the volume of the patch PA, and thus the relationship between the amount of substance that may be contained in the patch PA and the volume of the patch PA may be changed in accordance with the design or manufacturing method of the mesh structure.

The amount of substance contained in the patch PA may be reduced due to evaporation, loss, etc. with time. The substance may be additionally injected into the patch PA to increase or maintain the content of the substance contained in the patch PA. For example, a moisture keeping agent for suppressing evaporation of moisture may be added to the patch PA.

The patch PA may be implemented in a form in which it is easy to store the liquid substance SB. This signifies that, when the substance is affected by environmental factors such as humidity level, amount of light, and temperature, the patch PA may be implemented to minimize denaturalization of the substance. For example, to prevent the patch PA from being denaturalized due to external factors such as bacteria, the patch PA may be treated with a bacteria inhibitor.

A liquid substance SB having a plurality of components may be contained in the patch PA. In this case, the substance formed of a plurality of components may be placed together in the patch PA before a reference time point, or a primarily-injected substance may be first contained in the patch PA and then a secondary substance may be contained in the patch PA after a predetermined amount of time. For example, when a liquid substance SB formed of two components is contained in the patch PA, the two components may be contained in the patch PA upon manufacturing the patch PA, only one component may be contained in the patch PA upon manufacturing the patch PA and the other component may be contained therein later, or the two components may be sequentially contained in the patch PA after the patch PA is manufactured.

As described above, the substance contained in the patch may exhibit fluidity, and the substance may move irregularly or be diffused due to molecular motion in the patch PA.

2.1.3 Providing of Reaction Space

Figure 3:
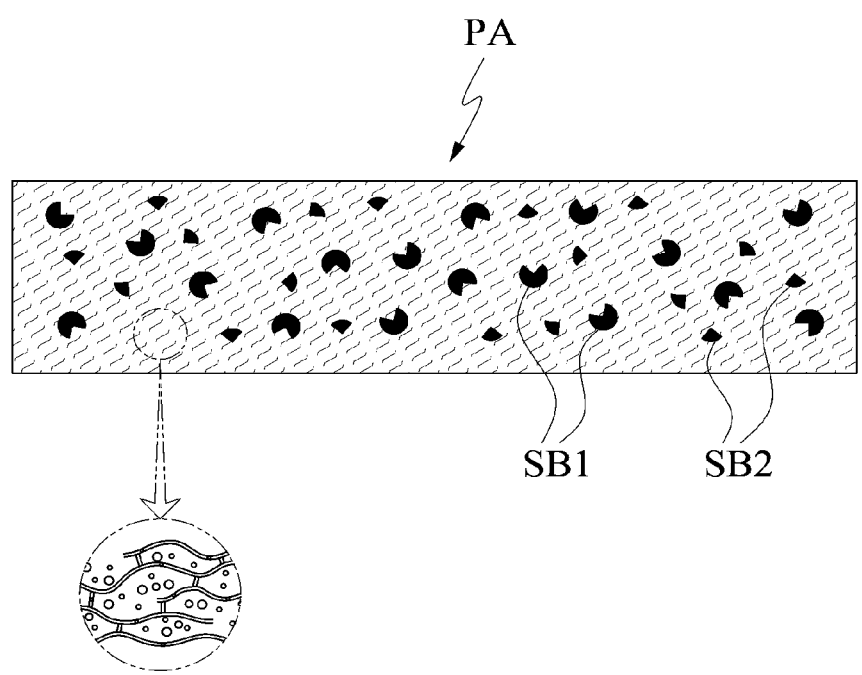
FIG. 3 illustrates providing of a reaction space as an example of a function of a patch according to the present application.
Figure 4:
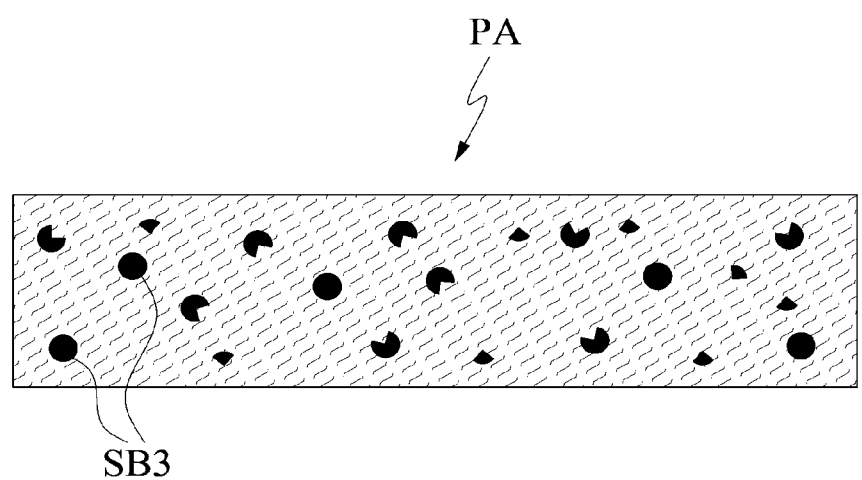
FIG. 4 illustrates providing of a reaction space as an example of a function of a patch according to the present application.

FIGS. 3 and 4 are views illustrating providing a reaction space as an example of a function of the patch according to the present application.

As illustrated in FIGS. 3 and 4, the patch PA according to the present application may perform a function of providing a space. In other words, the patch PA may provide a space in which the liquid substance SB may move through a space formed by the mesh structural body NS and/or a space constituting the mesh structural body NS.

The patch PA may provide a space for activity other than diffusion of particles and/or irregular motion of particles (hereinafter referred to as activity other than diffusion). The activity other than diffusion may refer to a chemical reaction, but is not limited thereto, and may also refer to a physical state change. More specifically, the activity other than diffusion may include a chemical reaction in which a chemical composition of the substance changes after the activity, a specific binding reaction between components included in the substance, homogenization of solutes or particles included in the substance and non-uniformly distributed therein, condensation of some components included in the substance, or a biological activity of a portion of the substance.

When a plurality of substances become involved in the activity, the plurality of substances may be placed together in the patch PA before a reference time point. The plurality of substances may be sequentially inserted into the patch PA.

By changing environmental conditions of the patch PA, efficiency of the function of providing a space for activities other than diffusion in the patch PA may be enhanced. For example, the activity may be promoted or a start of the activity may be induced by changing a temperature condition of the patch PA or adding an electrical condition thereto.

According to FIGS. 3 and 4, a first substance SB1 and a second substance SB2 placed in the patch PA may react inside the patch PA and be deformed into a third substance SB3 or generate the third substance SB3.

2.2 Channel

2.2.1 Meaning

Movement of a substance may occur between the patch PA and an external region. The substance may be moved from the patch PA to the external region of the patch PA or may be moved from the external region to the patch PA.

The patch PA may form a substance movement path or get involved in movement of the substance. More specifically, the patch PA may become involved in movement of the liquid substance SB captured in the patch PA or become involved in movement of an external substance through the liquid substance SB captured in the patch PA. The base substance BS or the additive substance AS may move out from the patch PA, or an external substance may be introduced from an external region to the patch PA.

The patch PA may provide a substance movement path. That is, the patch PA may become involved in movement of the substance and provide a substance movement channel. The patch PA may provide a substance movement channel based on unique properties of the liquid substance SB.

In accordance with whether the patch PA is connected to the external region, the patch PA may be in a state in which the liquid substance SB is movable between the patch PA and the external region or a state in which the liquid substance SB is immovable between the patch PA and the external region. When channeling between the patch PA and the external region begins, the patch PA may have unique functions.

Hereinafter, the state in which the substance is movable and the state in which the substance is immovable will be described first, and the unique functions of the patch PA will be described in detail in connection with whether the patch PA and the external region are connected.

Basically, irregular motion and/or diffusion of the substance are fundamental causes of movement of the liquid substance SB between the patch PA and the external region. However, controlling an external environmental factor (e.g., controlling a temperature condition, controlling an electrical condition, or the like) in order to control movement of a substance between the patch PA and the external region has already been described.

2.2.2 Movable State

In the state in which the substance is movable, a flow may occur between the liquid substance SB captured in the patch PA and/or the substance placed in the external region. In the state in which the substance is movable, substance movement may occur between the liquid substance SB captured in the patch PA and the external region.

For example, in the state in which the substance is movable, the liquid substance SB or some components of the liquid substance SB may be diffused to the external region or moved due to irregular motion. Alternatively, in the state in which the substance is movable, an external substance placed in the external region or some components of the external substance may be diffused to the liquid substance SB in the patch PA or moved due to irregular motion.

The state in which the substance is movable may be caused by contact. The contact may refer to connection between the liquid substance SB captured in the patch PA and the external region. Contact may refer to at least a partial overlap between a flow region of the liquid substance SB and the external region. The contact may refer to the external substance being connected to at least a portion of the patch PA. It may be understood that the range in which the captured liquid substance SB may flow is expanded in the state in which the substance is movable. In other words, in the state in which the substance is movable, the range in which the liquid substance SB may flow may be expanded to include at least a portion of the external region of the captured liquid substance SB. For example, when the liquid substance SB is in contact with the external region, the range in which the captured liquid substance SB may flow may be expanded to include at least a portion of the external region in contact. More specifically, when the external region is an external plate, the region in which the liquid substance SB may flow may be expanded to include a region of the external plate in contact with the liquid substance SB.

2.2.3 Immovable State

In the state in which the substance is immovable, substance movement may not occur between the liquid substance SB captured in the patch PA and the external region. However, substance movement may respectively occur in the liquid substance SB captured in the patch PA and in external substance placed in the external region.

The state in which the substance is immovable may be a state in which the contact is released. In other words, in the state in which contact between the patch PA and the external region is released, substance movement is not possible between the liquid substance SB remaining in the patch PA and the external region or the external substance.

More specifically, the state in which the contact is released may refer to a state in which the liquid substance SB captured in the patch PA is not connected to the external region. The state in which the contact is released may refer to a state in which the liquid substance SB is not connected to an external substance placed in the external region. For example, the state in which movement of the substance is impossible may be caused by separation between the patch PA and the external region.

In the present specification, although "movable state" has a meaning differentiated from that of "immovable state," a transition may occur between the states due to an elapse of time, an environmental change, and the like. In other words, the patch PA may be in the immovable state after being in the movable state, in the movable state after being in the immovable state, or may be in the movable state again, after being in the immovable state after being in the movable state.

2.2.4 Differentiation of Functions 2.2.4.1 Delivery

In the present application, due to the above-described characteristics, the patch PA may deliver at least a portion of the liquid substance SB captured in the patch PA to a desired external region. The delivery of the substance may refer to separation of a portion of the liquid substance SB captured in the patch PA from the patch PA due to a predetermined condition being satisfied. The separation of the portion of the liquid substance SB may refer to the portion of the substance being extracted, emitted, or released from a region that is affected by the patch PA. This is a concept subordinate to the above-described channeling function of the patch PA, and may be understood as defining transfer (delivery) of the substance placed in the patch PA to the outside of the patch PA.

The desired external region may be another patch PA, a dried region, or a liquid region.

The predetermined condition for the delivery to occur may be set as an environmental condition such as a temperature change, a pressure change, a change in an electrical characteristic, and a change in a physical state. For example, when the patch PA is in contact with an object whose force of binding to the liquid substance SB is larger than a force of binding to the mesh structural body NS of the patch PA, the liquid substance SB may be chemically bound with the object in contact, and as a result, at least a portion of the liquid substance SB may be provided to the object.

Hereinafter, for convenience, the above-described function of the patch PA will be referred to as "delivery."

The delivery may occur between the patch PA and the external region, via the state in which the liquid substance SB is movable and the state in which the liquid substance SB is immovable between the patch PA and the external region.

More specifically, when the liquid substance SB is in the movable state, the liquid substance SB may be diffused between the patch PA and the external region or may be moved to the external region due to irregular motion. In other words, the base solution and/or the additive substance AS included in the liquid substance SB may be moved from the patch PA to the external region. In the state in which the liquid substance SB is immovable, the liquid substance SB is unable to move between the patch PA and the external region. In other words, due to a transition from the movable state to the immovable state, a portion of the substance that has moved from the patch PA to the external region due to diffusion and/or irregular motion of the liquid substance SB become unable to move back to the patch PA. Thus, a portion of the liquid substance SB may be provided to the external region.

The delivery may be performed due to a difference between an attractive force between the liquid substance SB and the mesh structural body NS and an attractive force between the liquid substance SB and the external region or the external substance. The attractive force may be caused by similarity between polarities or a specific binding relationship.

More specifically, when the liquid substance SB is hydrophilic and the external region or the external substance is more hydrophilic than the mesh structural body NS, at least a portion of the liquid substance SB captured in the patch PA may be provided to the external region via the movable state and the immovable state.

The delivery of the liquid substance SB may also be performed selectively. For example, when a specific binding relationship exists between some components included in the liquid substance SB and the external substance, some of the ingredients may be selectively delivered via the state in which the substance is movable and the state in which the substance is immovable.

More specifically, when it is assumed that the patch PA provides a substance to an external plate PL, which is in a form of a flat plate, a substance that binds specifically to a portion of the liquid substance SB captured in the patch PA (e.g., a portion of a solute) may be applied on the external plate PL. In this case, the patch PA may selectively deliver a portion of the solute that binds specifically to the substance applied on the external plate PL from the patch PA to the plate PL via the movable state and the immovable state.

The delivery as a function of the patch PA will be described below according to a few examples of different regions to which the substance is moved. However, in giving the detailed description, the concepts of "release" of the liquid substance SB and "delivery" of the liquid substance SB may be interchangeably used.

Here, a case in which the liquid substance SB is provided from the patch PA to a separate external plate PL will be described. For example, a case in which the substance is moved from the patch PA to a plate PL, such as a slide glass, may be taken into consideration.

As the patch PA and the plate PL come into contact, at least a portion of the liquid substance SB captured in the patch PA is diffused to the plate PL or moved due to irregular motion. When the contact between the patch PA and the plate PL is released, the portion of the substance that has been moved from the patch PA to the plate PL (that is, the portion of the liquid substance SB) become unable to move back to the patch PA. As a result, the portion of the substance may be provided from the patch PA to the plate PL. In this case, the portion of the substance being provided may be the additive substance AS. For a substance in the patch PA to be "provided" by the contact and separation, an attractive force and/or binding force that acts between the substance and the plate PL should be present, and the attractive force and/or the binding force should be larger than the attractive force acting between the substance and the patch PA. Therefore, if the above-described "delivery condition" is not satisfied, delivery of a substance may not occur between the patch PA and the plate PL.

The delivery of a substance may be controlled by providing a temperature condition or an electrical condition to the patch PA.

The movement of a substance from the patch PA to the plate PL may depend on an extent of a contact area between the patch PA and the plate PL. For example, the substance movement efficiency between the patch PA and the plate PL may be increased or decreased in accordance with an extent of an area in which the patch PA and the plate PL come into contact.

When the patch PA includes a plurality of components, only some of the components may be selectively moved to the external plate PL. More specifically, a substance that binds specifically to some of the plurality of components may be fixed to the external plate PL. In this case, the substance fixed to the external plate PL may be in a liquid or solid state, or may be fixed to a different region. In this case, a portion of the substance of the plurality of components moves to the plate PL and binds specifically to the plate PL due to contact between the patch PA and the different region, and when the patch PA is separated from the plate PL, only some of the components may be selectively released to the plate PL.

Figure 5:
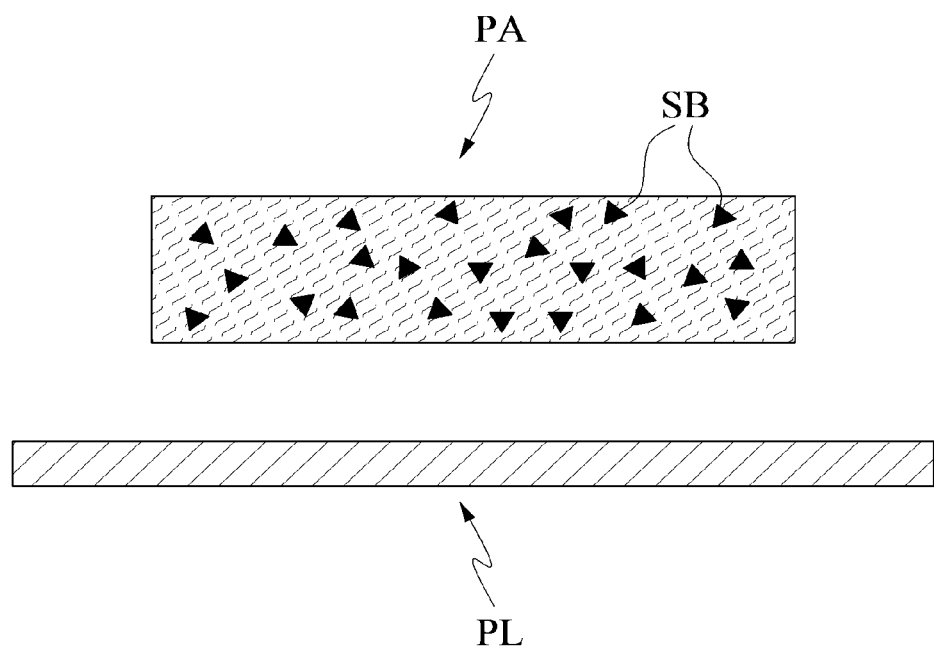
FIG. 5 illustrates providing of a substance as an example of a function of a patch according to the present application.
Figure 6:
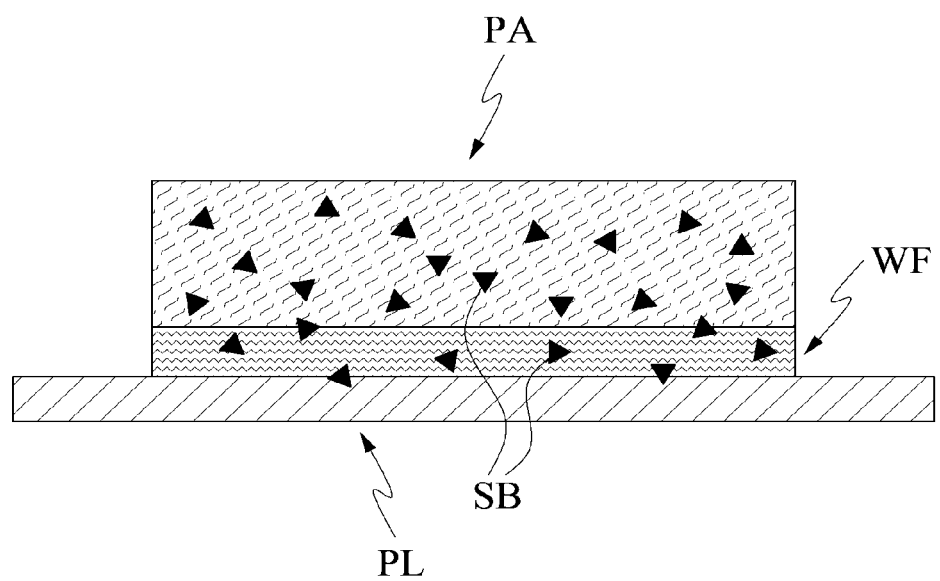
FIG. 6 illustrates providing of a substance as an example of a function of a patch according to the present application.
Figure 7:
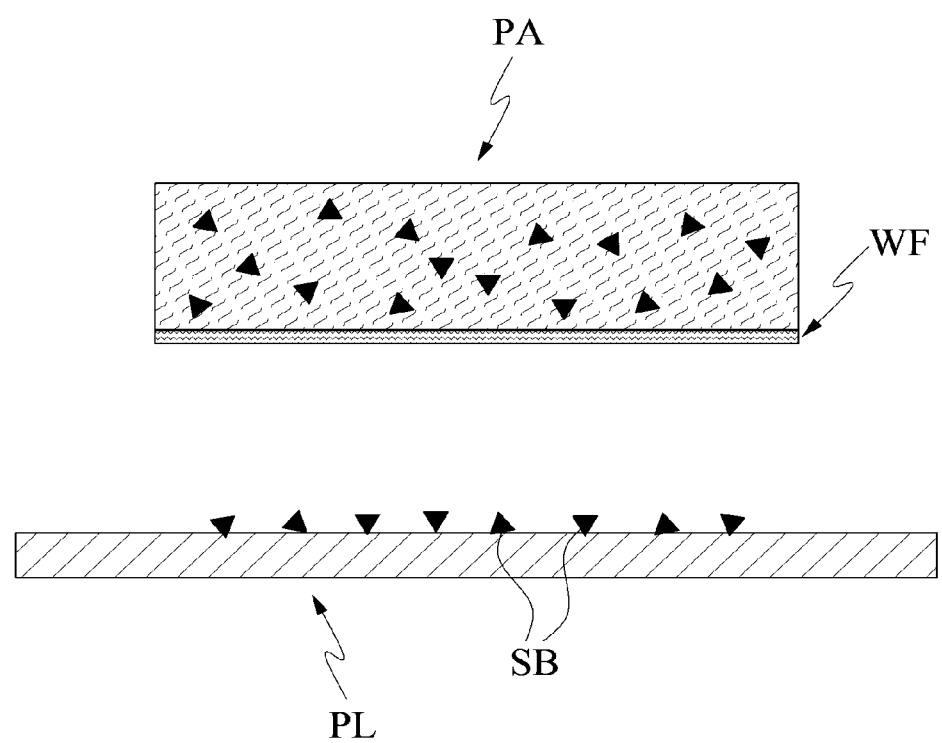
FIG. 7 illustrates providing of a substance as an example of a function of a patch according to the present application.

FIGS. 5 to 7 illustrate delivery of a substance from the patch PA to the external plate PL as an example of delivery of a substance from among the functions of the patch PA according to the present application. According to FIGS. 5 to 7, by the patch PA coming into contact with the external plate PL, a portion of a substance contained in the patch PA may be provided to the plate PL. In this case, providing of the substance may become possible by the patch PA coming into contact with the plate so that the substance is movable. In this case, a water film WF may be formed in the vicinity of a contact surface at which the plate and the patch PA come into contact, and the substance may be movable through the formed water film WF.

Here, a case in which the liquid substance SB is provided from the patch PA to a substance having fluidity SL will be described. The substance having fluidity SL may be a liquid substance that is held in other containing space or that is flowing.

As the patch PA and the substance having fluidity come into contact (for example, the patch PA is put into a solution), at least a portion of the liquid substance SB captured in the patch PA may be diffused or moved due to irregular motion to the substance having fluidity SL. When the patch PA and the substance having fluidity SL are separated, a portion of the liquid substance SB that has been moved from the patch PA to the substance having fluidity become unable to move back to the patch PA so that a portion of the substance in the patch PA may be provided to the substance having fluidity.

The substance movement between the patch PA and the substance having fluidity SL may depend on an extent of a contact area between the patch PA and the substance having fluidity SL. For example, the substance movement efficiency between the patch PA and the substance having fluidity SL may be increased or decreased in accordance with an extent of an area at which the patch PA and the substance having fluidity SL come into contact (for example, a depth at which the patch PA is immersed into a solution or the like).

The substance movement between the patch PA and the substance having fluidity SL may be controlled through physical separation between the patch PA and the substance having fluidity.

A partial concentration of the additive substance AS in the liquid substance SB and a partial concentration of the additive substance AS in the substance having fluidity may be different, and the additive substance AS may be provided from the patch PA to the substance having fluidity.

However, in the patch PA providing the liquid substance SB to the substance having fluidity SL, the physical separation between the patch PA and the substance having fluidity SL is not essential. For example, when a force (driving force/casual force) that causes a substance to move from the patch PA to a liquid having fluidity disappears or is decreased to a reference value or lower, the movement of the substance may be stopped.

In "delivery" between the patch PA and the substance having fluidity SL, the above-described "delivery condition" between the patch PA and the substance having fluidity SL may not be required. It may be understood that substances that have already moved to the substance having fluidity SL are diffused and/or moved due to irregular motion in the substance having fluidity SL, and the substance has been provided to the substance having fluidity SL when a distance between the moved substance and the patch PA become larger a predetermined distance. Since, while in the case of the plate PL, a movable range expanded due to the contact is extremely limited, and thus the attractive force between the patch PA and the substances that have moved to the plate PL may be significant, in the relationship between the patch PA and the substance having fluidity, a movable range expanded due to contact between the patch PA and the plate PL is relatively much wider, and thus the attractive force between the patch PA and the substances that have moved to the substance having fluidity SL is insignificant.

Figure 8:
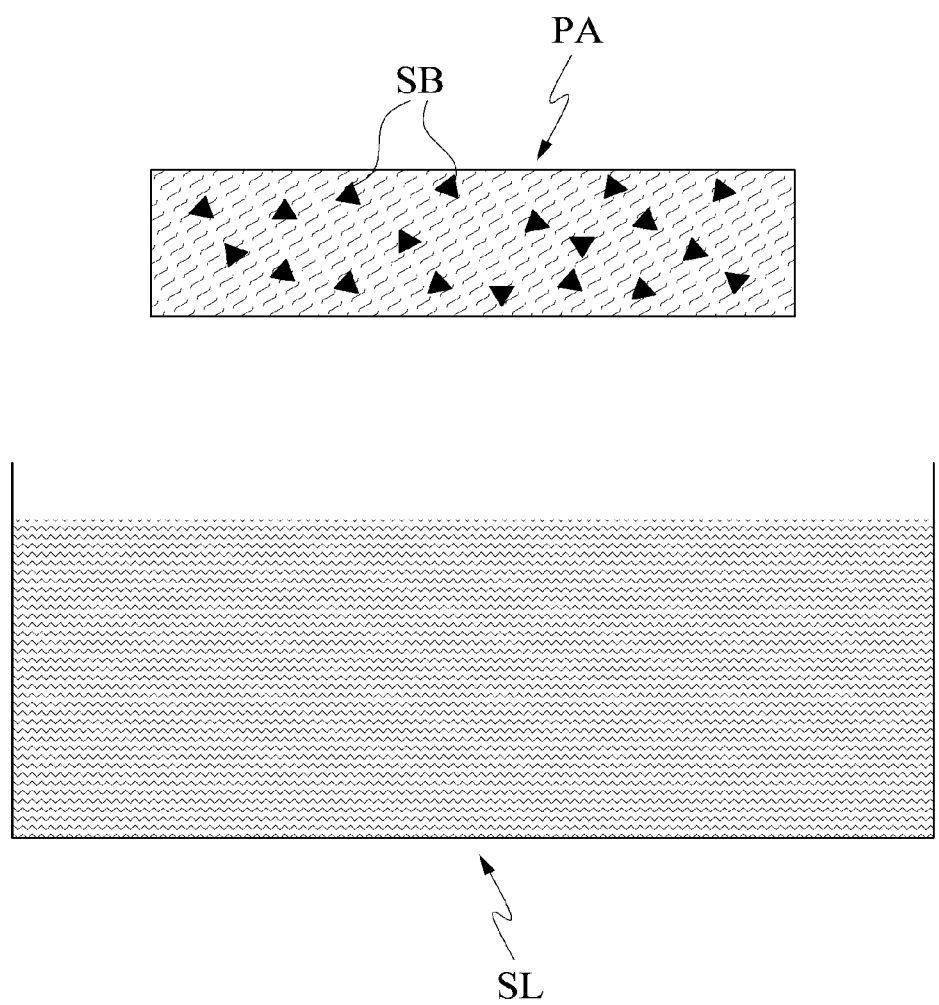
FIG. 8 illustrates providing of a substance as an example of a function of a patch according to the present application.
Figure 9:
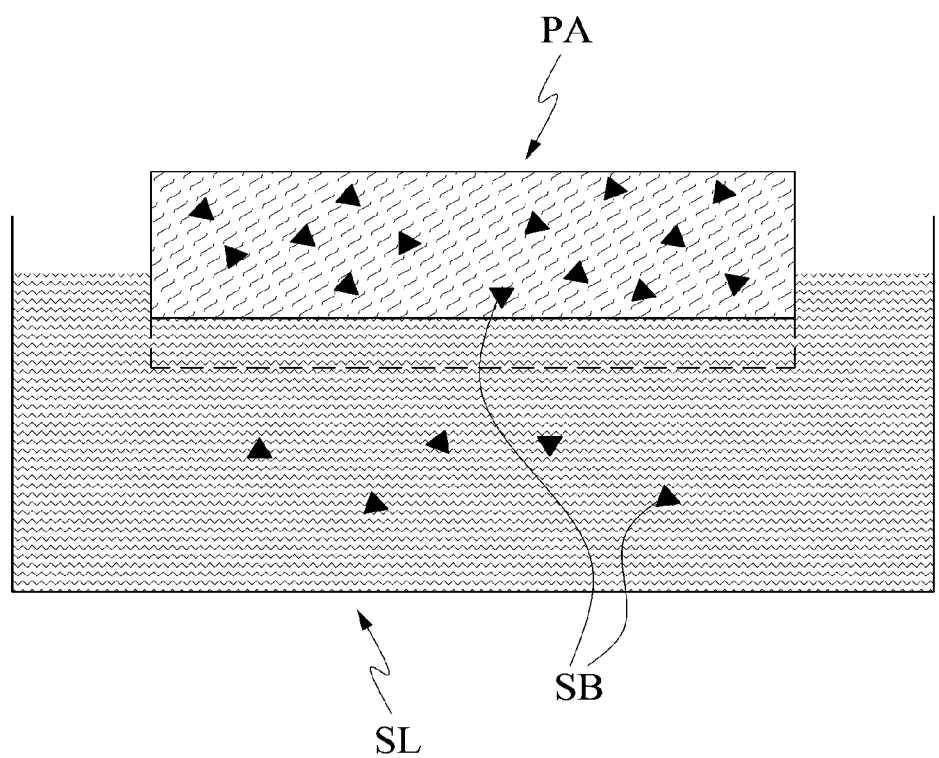
FIG. 9 illustrates providing of a substance as an example of a function of a patch according to the present application.
Figure 10:
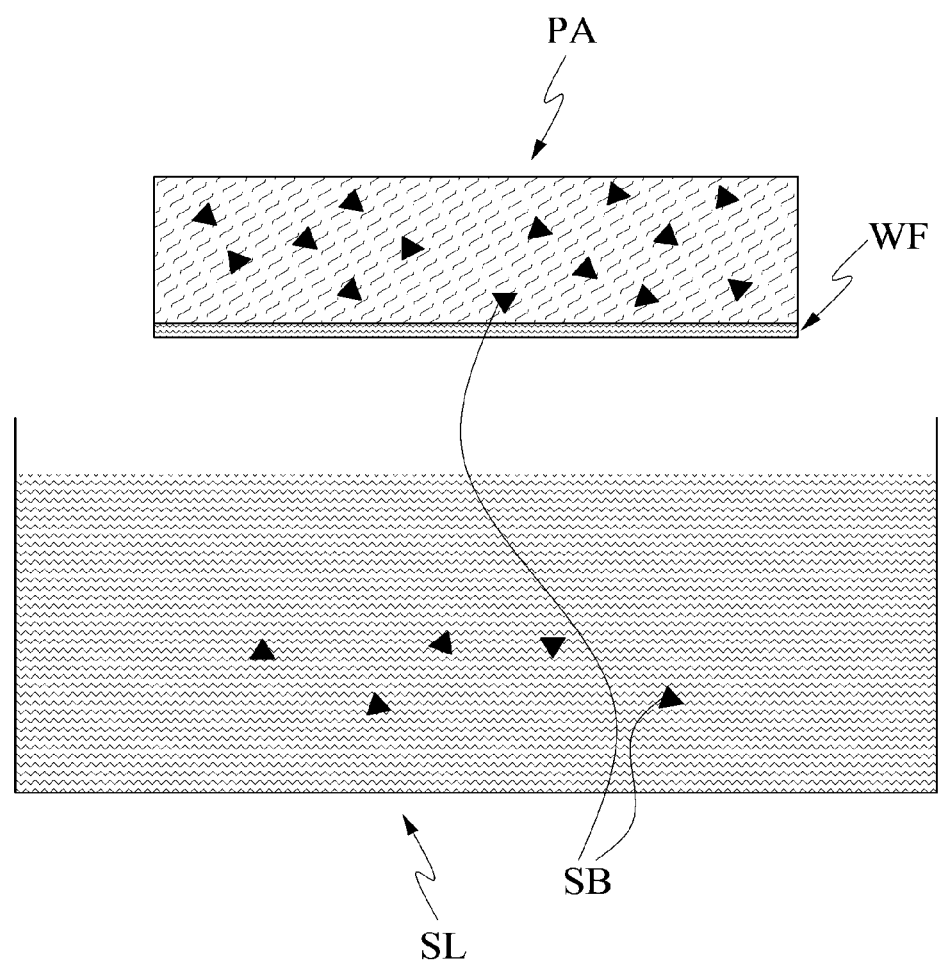
FIG. 10 illustrates providing of a substance as an example of a function of a patch according to the present application.

FIGS. 8 to 10 illustrate delivery of a substance from the patch PA to the substance having fluidity as an example of delivery of a substance from among the functions of the patch PA according to the present application. According to FIGS. 8 to 10, the patch PA may deliver a portion of a substance contained in the patch PA to an external substance having fluidity. The delivery of the portion of the contained substance may be performed by the patch PA being inserted into or coming into contact with the substance having fluidity so that substance movement is possible between the liquid substance SB captured in the patch PA and the substance having fluidity.

Here, it is assumed that a substance is moved from the patch PA to another patch PA. In a contact region in which the patch PA and the other patch PA are in contact, at least a portion of the liquid substance B provided in the patch PA may be moved to the other patch PA.

In the contact region, the liquid substance SB provided in each patch PA may be diffused and moved to the other patch PA. In this case, due to the movement of the substance, a concentration of the liquid substance SB provided in each patch PA may be changed. Also in the present embodiment, as described above, the patch PA and the other patch PA may be separated, and a portion of the liquid substance SB in the patch PA may be provided to the other patch PA.

The substance movement between the patch PA and the other patch PA may be performed through a change in an environmental condition including a change in a physical state.

The substance movement between the patch PA and another patch PA may depend on an extent of a contact area between the patch PA and the other patch PA. For example, the substance movement efficiency between the patch PA and the other patch PA may be increased or decreased in accordance with an extent of an area where the patch PA comes into contact with the other patch PA.

Figure 11:
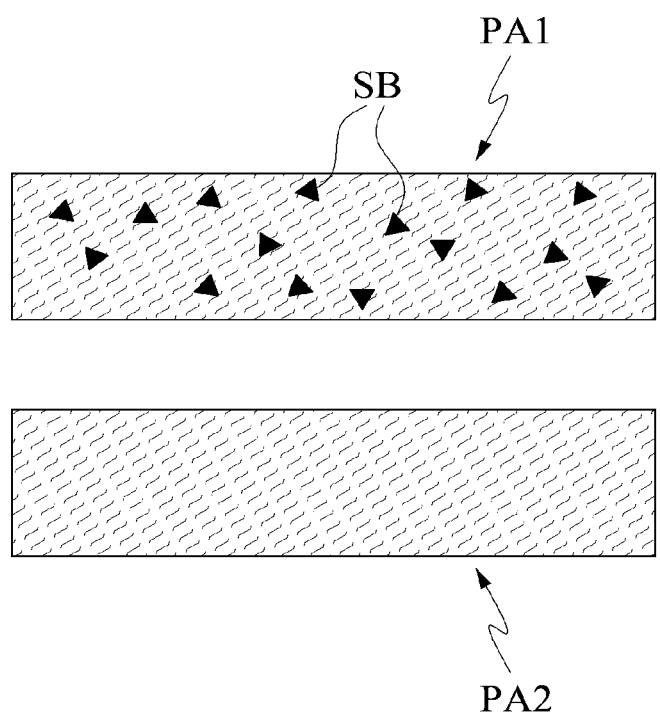
FIG. 11 illustrates providing of a substance as an example of a function of a patch according to the present application.
Figure 12:
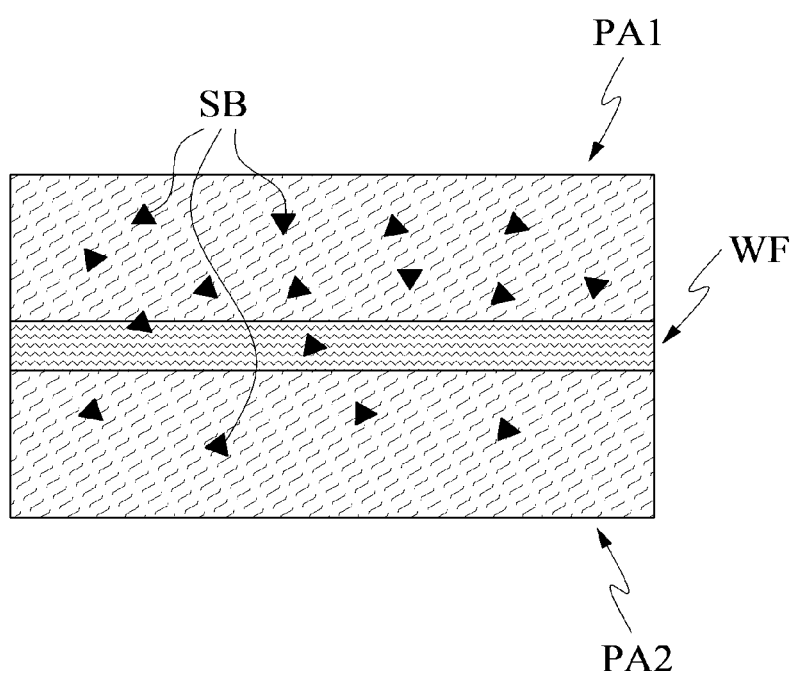
FIG. 12 illustrates providing of a substance as an example of a function of a patch according to the present application.
Figure 13:
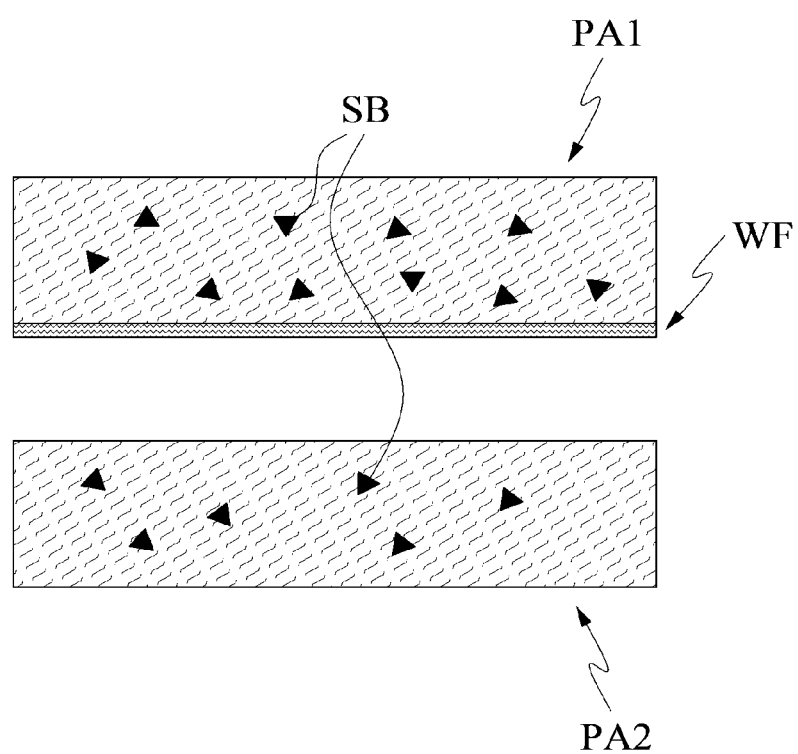
FIG. 13 illustrates providing of a substance as an example of a function of a patch according to the present application.

FIGS. 11 to 13 illustrate delivery of a substance from a patch PA1 to another patch PA2 as an example of delivery of a substance among the functions of the patch PA according to the present application. According to FIGS. 11 to 13, the patch PA1 may deliver a portion of a substance contained in the patch PA1 to the other patch PA2. The delivery of the portion of the substance may be performed by the patch PA1 coming into contact with the other patch PA2 and becoming a state in which a liquid substance SB captured in the patch PA1 and a substance captured in the other patch PA2 are exchangeable.

2.2.4.2 Absorption

Prior to description, it should be noted that, among the functions of the patch PA according to the present application, "absorption" may be managed similarly as the above-described "delivery" in some embodiments. For example, in a case in which a substance moves due to a concentration differences between substances, the "absorption" may be similar to the "delivery" in that a concentration of the liquid substance SB, particularly, a concentration of the additive substance AS, may be changed to control a direction in which the substance is moved. The "absorption" may also be similar to "delivery" in terms of controlling movement and selective absorption of a substance through a release of physical contact with the patch PA, and this may be clearly understood by those of ordinary skill in the art to which the present application pertains.

Due to the above-described characteristics, the patch PA according to the present application may capture an external substance. The patch PA may pull in an external substance present outside a region defined by the patch PA toward a region affected by the patch PA. The pulled external substance may be captured along with the liquid substance SB of the patch PA. The pulling of the external substance may be caused by an attractive force between the external substance and the liquid substance SB already captured in the patch PA. Alternatively, the pulling of the external substance may be caused by an attractive force between the external substance and a region of the mesh structural body NS not occupied by the liquid substance SB. The pulling of the external substance may be caused by a force of surface tension.

Hereinafter, for convenience, the above-described function of the patch PA will be referred to as "absorption." Absorption may be understood as a concept subordinate to the above-described channeling function of the patch PA, the concept defining movement of an external substance to the patch PA.

The absorption may occur by the patch PA via a state in which the substance is movable and a state in which the substance is immovable.

A substance that is absorbable by the patch PA may be in a liquid or solid state. For example, when the patch PA comes into contact with an external substance including a solid state substance, absorption of the substance may be performed due to an attractive force between the solid state substance included in the external substance and the liquid substance SB placed in the patch PA. As another example, when the patch PA comes into contact with a liquid external substance, the absorption may be performed due to binding between the liquid external substance and the liquid substance SB placed in the patch PA.

The external substance absorbed into the patch PA may be moved to the inside of the patch PA through the microcavities of the mesh structural body NS forming the patch PA or may be distributed on a surface of the patch PA.

Positions at which the external substance is distributed may be set on the basis of a molecular weight or a particle size of the external substance.

While the absorption is performed, the form of the patch PA may be changed. For example, the volume, color, and the like of the patch PA may be changed. While the absorption into the patch PA is being performed, the absorption into the patch PA may be activated or delayed by adding external conditions such as a temperature change and a physical state change to an absorption environment of the patch PA.

The absorption will be described below as a function of the patch PA according to some examples of an external region that provides a substance to be absorbed into the patch PA when the absorption occurs.

Hereinafter, it will be assumed that the patch PA absorbs an external substance from a external plate PL. An example of the external plate may include a plate PL in which the external substance may be placed while the external substance is not absorbed thereinto.

A substance may be applied on the external plate PL. Particularly, a substance may be applied in a form of powder on the plate PL. The substance applied on the plate PL may be a single component or a mixture of a plurality of components.

The plate PL may have the shape of a flat plate. The shape of the plate PL may be deformed for improvement in ability to contain the substance or the like. For example, a well may be formed to improve the ability to contain the substance, a surface of the plate PL may be deformed by engraving or embossing, or a patterned plate PL may be used to improve contact with the patch PA.

The absorption of a substance from the plate PL by the patch PA according to the present application may be performed through contact between the plate PL and the patch PA. In this case, in a contact region in the vicinity of a contact surface between the plate PL and the patch PA, a water film WF may be formed due to the liquid substance SB captured in the patch PA and/or the substance applied on the plate PL. When the water film (aquaplane, hydroplane) WF is formed in the contact region, the substance applied on the plate PL may be captured by the water film WE The substance captured in the water film WF may freely flow within the patch PA.

When the patch PA is spaced a predetermined distance or more apart and separated from the plate PL, the water film WF may be moved along with the patch PA, and the substance applied on the plate PL may be absorbed into the patch PA. The substance applied on the plate PL may be absorbed into the patch PA as the patch PA is separated a predetermined distance or more apart from the plate PL. When the patch PA and the plate PL are spaced apart and separated, the liquid substance SB provided to the patch PA may not be moved to the plate PL, or only an insignificant amount thereof may be absorbed into the patch PA.

A portion of or the entire substance applied on the plate PL may react specifically with a portion of or the entire substance captured in the patch PA. In this respect, absorption of a substance from the plate PL by the patch PA may be selectively performed. Particularly, the absorption may be performed selectively when the patch PA has a stronger attractive force than the plate PL with respect to a portion of the substance captured in the patch PA.

As an example, a portion of the substance may be fixed to the plate PL. In other words, a portion of the substance may be fixed to the plate PL while another portion of the substance is applied to have fluidity or not be fixed. In this case, when the patch PA and the plate PL are brought into contact and separated, the substance, excluding the portion of the substance fixed to the plate PL of the substance applied on the plate PL, may be selectively absorbed into the patch PA. Instead, the selective absorption may also occur due to polarities of a substance placed on the plate PL and a substance captured in the patch PA regardless of whether the substance is fixed.

As another example, when the liquid substance SB captured in the patch PA is bound specifically to at least a portion of a substance applied on the plate PL, only the portion of the substance applied on the plate PL bound specifically to the liquid substance SB may be absorbed into the patch PA when the patch PA is brought into contact with and then separated from the substance applied on the plate PL.

As yet another example, a portion of the substance applied on the plate PL may react specifically with a substance fixed to the plate PL in advance. In this case, only a remaining substance, excluding the substance that reacts specifically with the substance fixed to the plate PL in advance of the substance being applied to the plate PL, may be absorbed into the patch PA.

Figure 14:
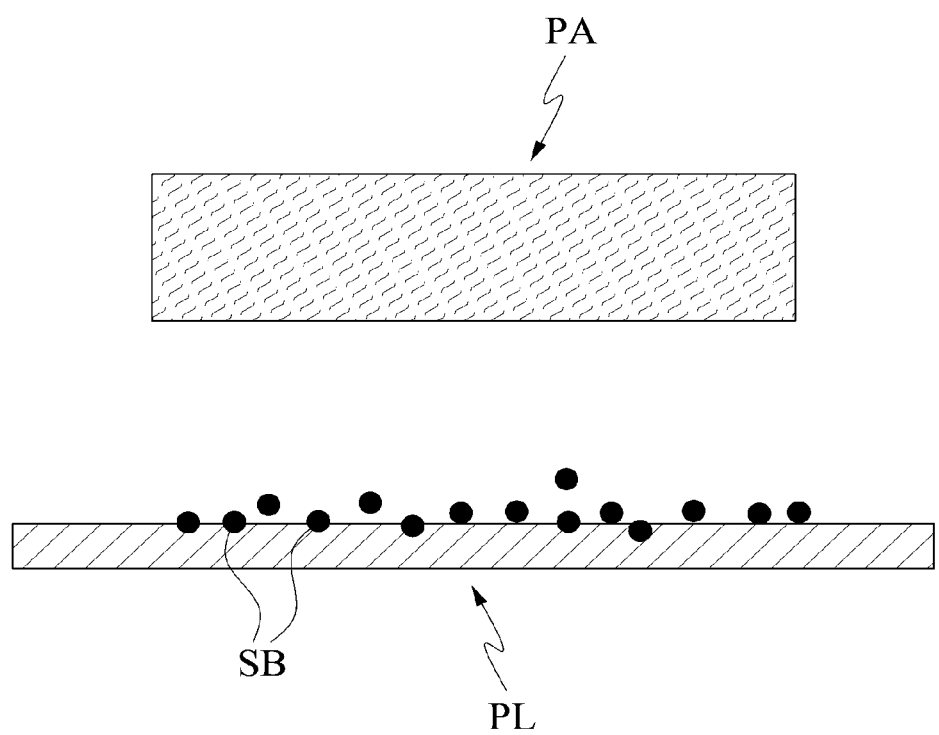
FIG. 14 illustrates absorbing of a substance as an example of a function of a patch according to the present application.
Figure 15:
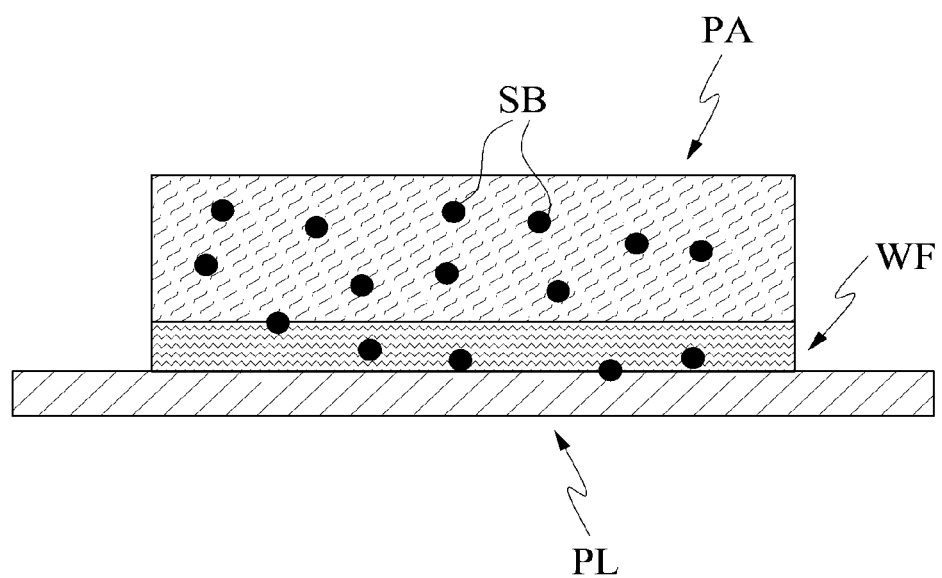
FIG. 15 illustrates absorbing of a substance as an example of a function of a patch according to the present application.
Figure 16:
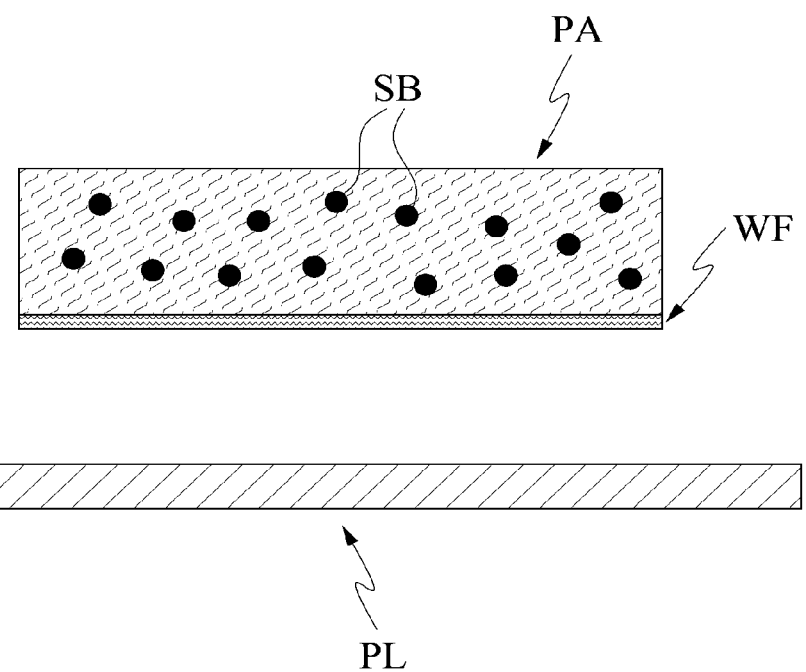
FIG. 16 illustrates absorbing of a substance as an example of a function of a patch according to the present application.

FIGS. 14 to 16 illustrate absorption of a substance from an external plate PL by the patch PA as an example of absorption of a substance from among the functions of the patch PA according to the present application. According to FIGS. 14 to 16, the patch PA may absorb a portion of a substance placed on the external plate PL from the external plate PL. The absorption of the substance may be performed by the patch PA coming into contact with the external plate PL, the water film WF being formed in the vicinity of a contact region between the external plate PL and the patch PA, and the substance being movable to the patch PA through the water film WF.

Here, it will be assumed that a substance is absorbed into the patch PA from the substance having fluidity SL. The substance having fluidity SL may refer to a liquid external substance that is held in other containing space or that is flowing. More specifically, by having an environment in which the substance having fluidity SL and the liquid substance SB captured in the patch PA may flow to and from each other, a portion of or the entire substance having fluidity SL may be absorbed into the patch PA. In this case, the environment in which the substance having fluidity SL and the liquid substance SB may flow to and from each other may be formed by the patch PA coming into contact with at least a portion of the substance having fluidity SL.

When the patch PA comes into contact with the substance having fluidity SL, the patch PA may be in a state in which a substance is movable from the substance having fluidity SL. When the patch PA is separated from the substance having fluidity SL, at least a portion of the substance having fluidity SL may be absorbed into the patch PA.

The absorption of a substance into the patch PA from the substance having fluidity SL may depend on a concentration difference between the substance captured in the patch PA and the substance having fluidity SL. In other words, when the concentration of the liquid substance SB captured in the patch PA with respect to a predetermined additive substance AS is lower than the concentration of the substance having fluidity SL with respect to the predetermined additive substance AS, the predetermined additive substance AS may be absorbed into the patch PA.

When a substance is absorbed into the patch PA from the substance having fluidity SL, in addition to the absorption depending on the concentration difference while the patch PA and the substance having fluidity SL are in contact as described above, the absorption into the patch PA may also be controlled by adding an electrical factor or changing a physical condition. Further, without direct contact between the substance captured in the patch PA and a substance to be absorbed, the absorption of a substance may also be performed through indirect contact therebetween via a medium.

Figure 17:
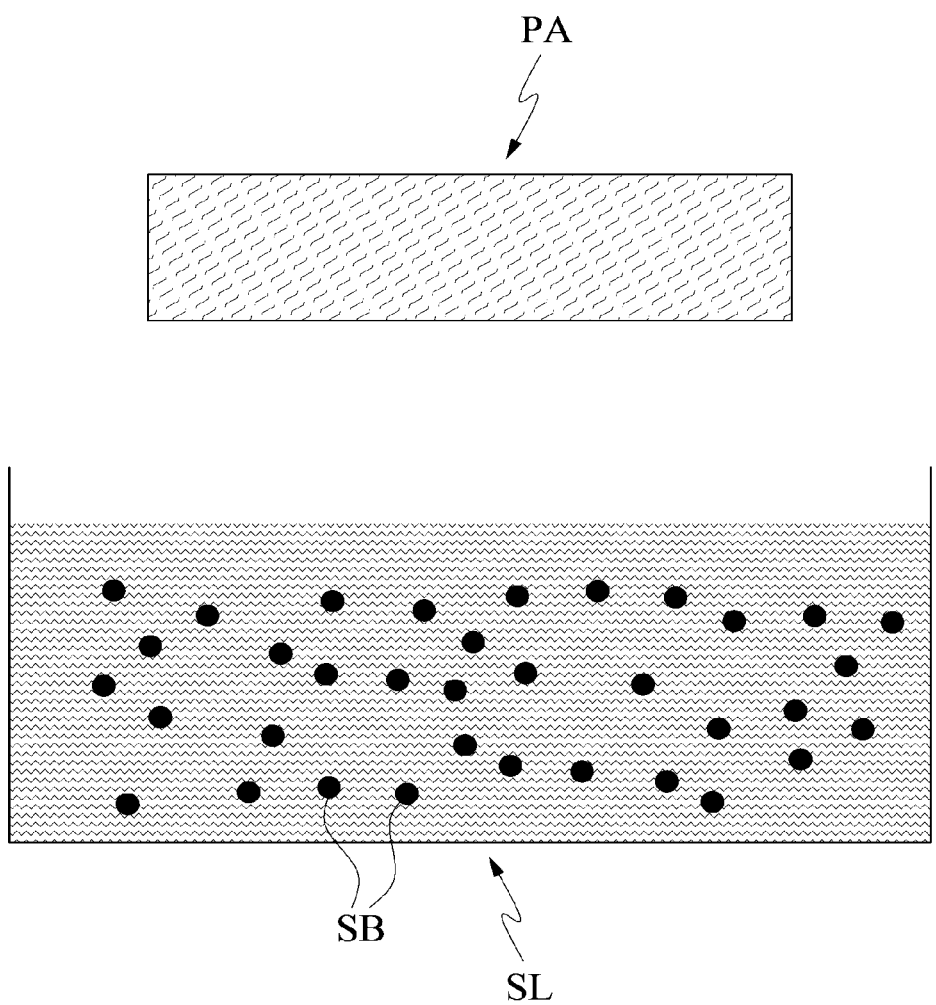
FIG. 17 illustrates absorbing of a substance as an example of a function of a patch according to the present application.
Figure 18:
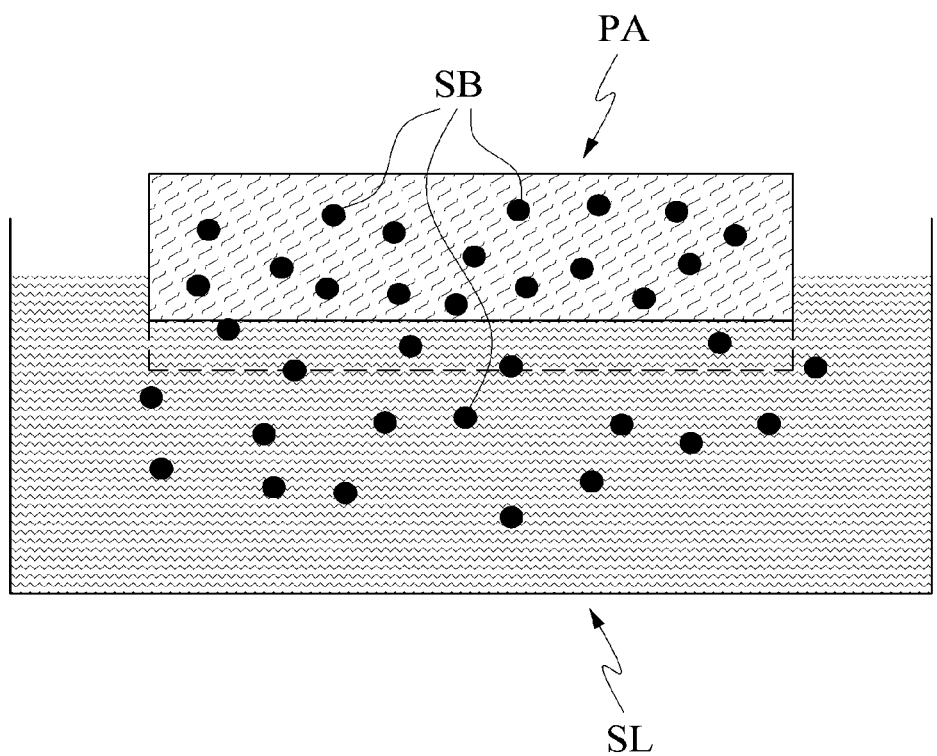
FIG. 18 illustrates absorbing of a substance as an example of a function of a patch according to the present application.
Figure 19:
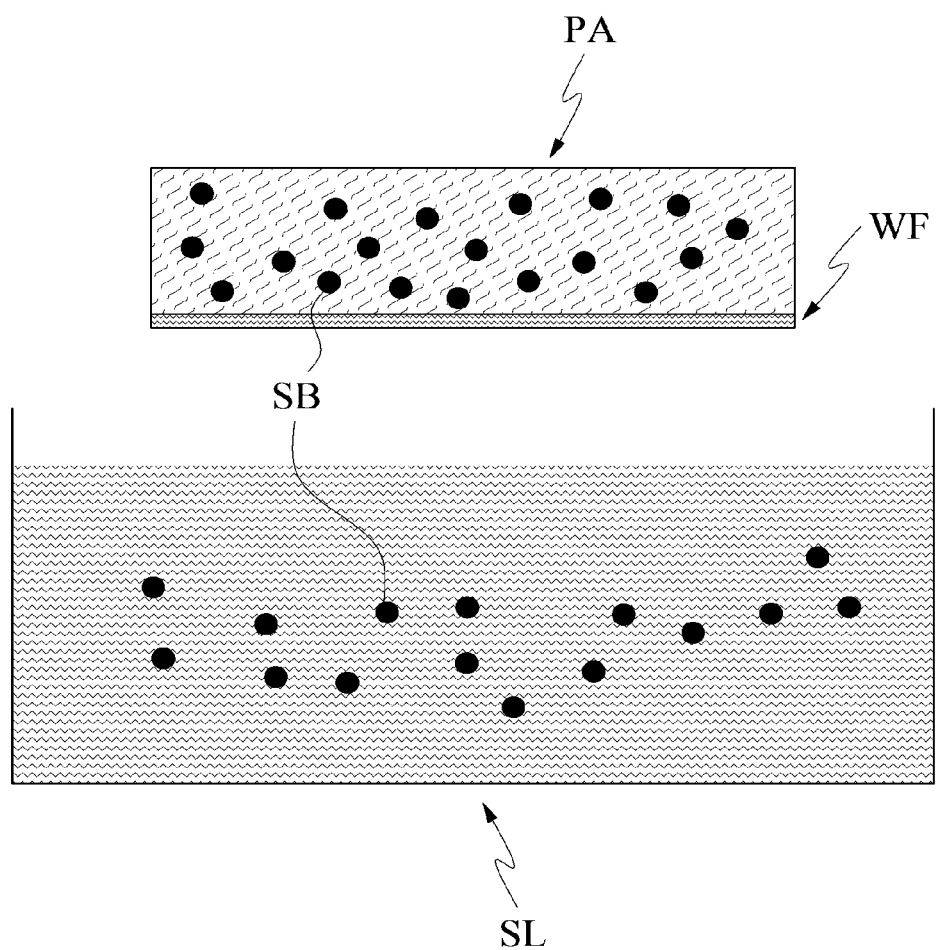
FIG. 19 illustrates absorbing of a substance as an example of a function of a patch according to the present application.

FIGS. 17 to 19 illustrate absorption of a substance from the substance having fluidity SL by the patch PA as an example of absorption of a substance from among the functions of the patch PA according to the present application. According to FIGS. 17 to 19, the patch PA may absorb a portion of the substance having fluidity SL. The absorption of a substance may be performed by the patch PA being immersed into the substance having fluidity SL or coming into contact with the substance having fluidity SL so that the liquid substance SB captured in the patch PA and the substance having fluidity SL are movable to and from each other.

Here, it will be assumed that the patch PA absorbs an external substance from another patch PA.

The absorption of an external substance from another patch PA by the patch PA may be performed due to a difference in binding force between the absorbed external substance and the substance already captured in the patch PA and between the absorbed external substance and the external substance not absorbed into the patch PA. For example, when the absorbed substance exhibits hydrophilic property, the patch PA exhibits hydrophilic property, and an attractive force between the absorbed substance and the patch PA is stronger than an attractive force between the other patch PA and the absorbed substance (that is, when the patch PA is more hydrophilic than the other patch PA), at least a portion of the external substance may be absorbed into the patch PA when the patch PA and the other patch PA are separated after being brought into contact.

Figure 20:
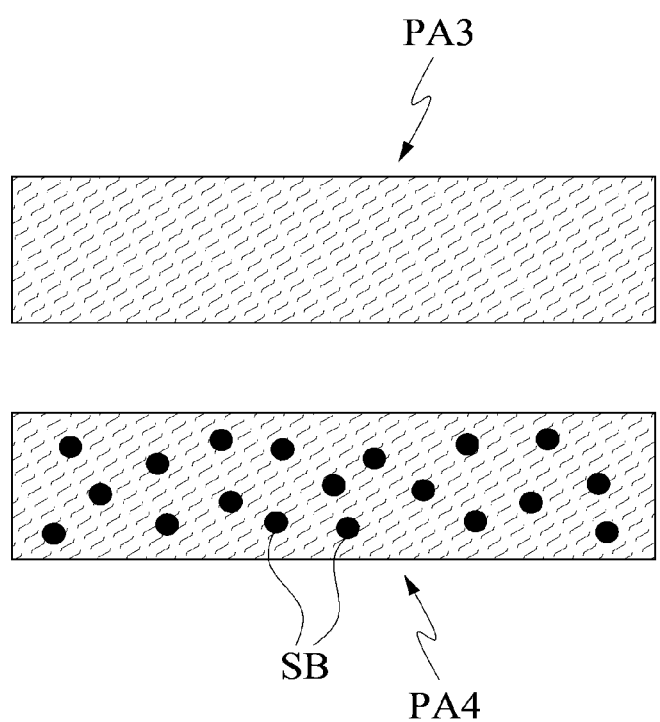
FIG. 20 illustrates absorbing of a substance as an example of a function of a patch according to the present application.
Figure 21:
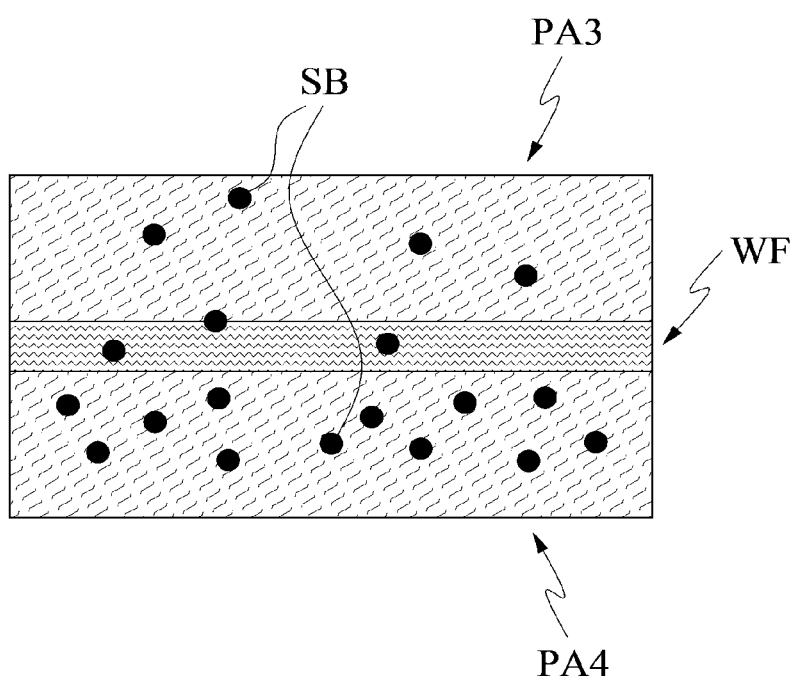
FIG. 21 illustrates absorbing of a substance as an example of a function of a patch according to the present application.
Figure 22:
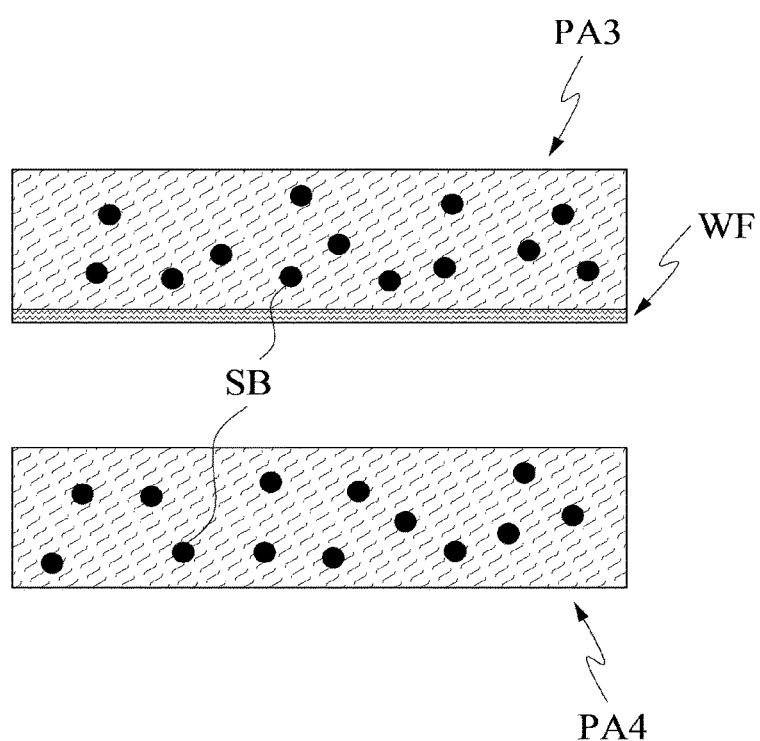
FIG. 22 illustrates absorbing of a substance as an example of a function of a patch according to the present application.

FIGS. 20 to 22 illustrate absorption of a substance from another patch PA4 by a patch PA3 as an example of absorption of a substance among the functions of the patch PA according to the present application. According to FIGS. 20 to 22, the patch PA3 may absorb a portion of a substance placed in the other patch PA4. The absorption of the substance may be performed by the patch PA3 coming into contact with the other patch PA4 so that a liquid substance SB captured in the patch PA3 and a liquid substance SB captured in the other patch PA4 are exchangeable.

A binding force of the patch PA to the external substance absorbed thereinto may be changed in accordance with a proportion of a frame structural body of the three-dimensional mesh structural body NS constituting the patch PA with respect to the total volume of the patch PA. For example, as the proportion of a volume occupied by the frame structural body in the entire patch PA increases, the amount of substance captured in the structural body may be reduced. In this case, a binding force between the patch PA and a target substance may be reduced due to a reason such as reduction in a contact area between the target substance and the substance captured in the patch PA.

In relation to this, ratios of materials that constitutes the mesh structural body NS may be adjusted during manufacturing process of the patch PA so that polarity of the patch PA is controlled. For example, in the case of a patch PA manufactured using agarose, a concentration of the agarose may be controlled to adjust a degree of the absorption.

When the certain region has a weaker binding force than the patch PA with respect to a substance provided from the patch PA, and the patch PA and another patch PA are brought into contact and then separated, the absorbed external substance may be separated from the other patch PA along with the patch PA.

2.2.4.3 Providing of Environment

Due to the above-described characteristics, the patch PA according to the present application may perform a function of adjusting an environmental condition of a desired region. The patch PA may provide an environment due to the patch PA to the desired region.

The environmental condition due to the patch PA may depend on the liquid substance SB captured in the patch PA. The patch PA may create a desired environment in a substance placed in an external region on the basis of characteristics of a substance accommodated in the patch PA or for a purpose of making the environment correspond to characteristics of the substance accommodated in the patch PA.

The adjustment of the environment may be understood as changing an environmental condition of the desired region. The changing of the environmental condition of the desired region may be implemented in a form in which a region affected by the patch PA is expanded to include at least a portion of the desired region or a form in which an environment of the patch PA is shared with the desired region.

Hereinafter, for convenience, the above-described function of the patch PA will be referred to as "providing of an environment."

The providing of an environment by the patch PA may be performed in a state in which a substance is movable between the patch PA and an external region subject to provide the environment. The providing of an environment by the patch PA may be performed through contact. For example, when the patch PA comes into contact with a desired region (for example, an external substance, a plate PL, or the like), a specific environment may be provided to the desired region by the patch PA.

The patch PA may adjust an environment of a target region TA by providing an environment with an appropriate pH, osmotic pressure, humidity level, concentration, temperature, and the like. For example, the patch PA may provide fluidity (liquidity) to the target region TA or a target substance. Such providing of fluidity may occur due to movement of a portion of a substance captured in the patch PA. A moist environment may be provided to the target region TA through the liquid substance SB or the base substance BS captured in the patch PA.

The environmental factors provided by the patch PA may be constantly maintained in accordance with a purpose. For example, the patch PA may provide homeostasis to the desired region. As another example, as a result of providing an environment, the substance captured in the patch PA may be adapted to an environmental condition of the desired region The providing of an environment by the patch PA may result from diffusion of the liquid substance SB included in the patch PA. That is, when the patch PA and the desired region come into contact, a substance may be movable through a contact region that is formed due to contact between the patch PA and the desired region. In relation to this, an environmental change due to an osmotic pressure, an environmental change due to a change in ionic concentration, providing of a moist environment, and a change in a pH level may be implemented in accordance with a direction in which the substance is diffused.

Figure 23:
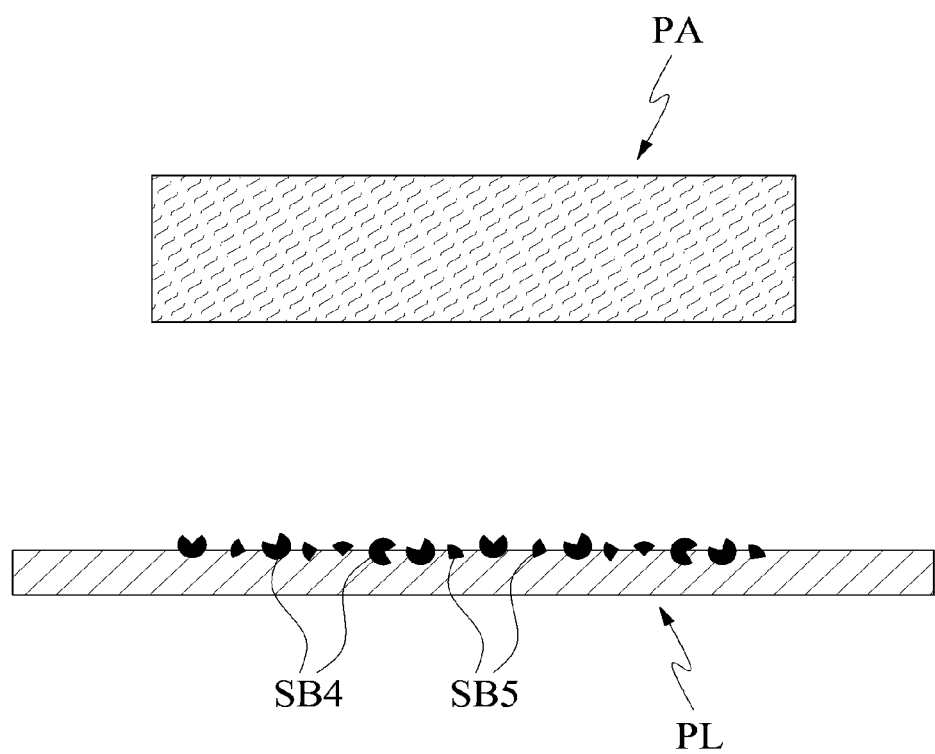
FIG. 23 illustrates providing of an environment as an example of a function of a patch according to the present application.
Figure 24:
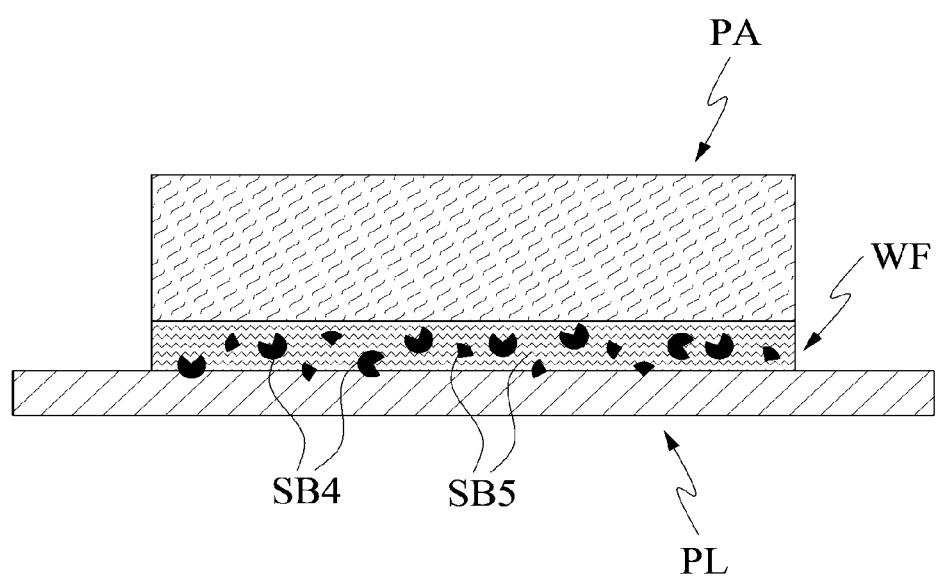
FIG. 24 illustrates providing of an environment as an example of a function of a patch according to the present application.
Figure 25:
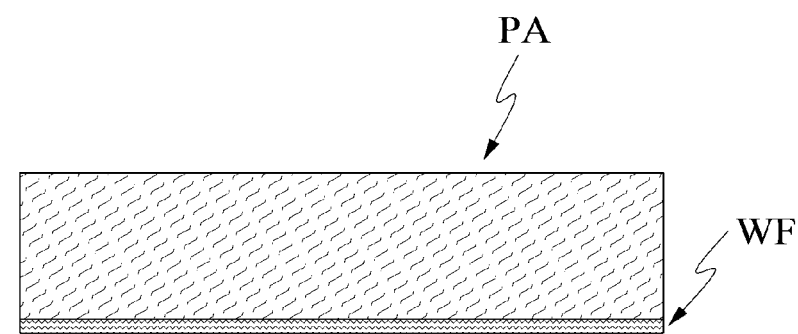
FIG. 25 illustrates providing of an environment as an example of a function of a patch according to the present application.
Figure 25:
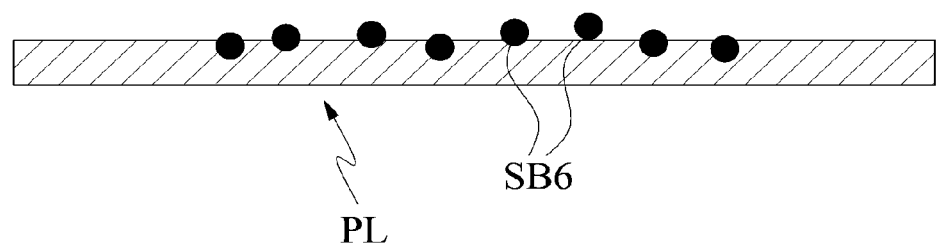

FIGS. 23 to 25 illustrate providing of a predetermined environment to an external plate PL by the patch PA as an example of providing of an environment among the functions of the patch PA according to the present application.

According to FIGS. 23 to 25, the patch PA may provide a predetermined environment to an external plate PL on which a fourth substance SB4 and a fifth substance SB5 are placed. For example, the patch PA may provide a predetermined environment to the plate PL for the fourth substance SB4 and the fifth substance SB5 to react and form a sixth substance SB6. The providing of the environment may be performed by the patch PA coming into contact with the plate PL so that a water film WF is formed in the vicinity of a contact region and the fourth substance SB4 and the fifth substance SB5 are captured in the water film WF.

3. Application of Patch

The patch PA according to the present application may be implemented to perform various functions by suitably applying the above-described functions of the patch PA.

The technical spirit of the present application will be described below by disclosing some embodiments. However, the technical scope to which functions of the patch PA disclosed by the present application are applied may be interpreted in a broad sense within the scope that may be easily derived by those of ordinary skill in the art, and the scope of the present application should not be interpreted as being limited by the embodiments disclosed herein.

3.1. In-Patch

The patch PA may provide a reaction region for a substance. In other words, a reaction of a substance may occur in at least a portion of a spatial region affected by the patch PA. In this case, the reaction of a substance may be a reaction between liquid substances SB captured in the patch PA and/or a reaction between the captured liquid substance SB and a substance provided from the outside of the patch PA. The providing of a reaction region for a substance may activate or promote a reaction of a substance.

In this case, the liquid substance SB captured in the patch PA may include at least one of a substance added upon manufacturing the patch PA, a substance additive into the patch PA after the manufacturing of the patch PA and contained in the patch PA, and a substance temporarily captured in the patch PA. In other words, regardless of a form in which a substance is captured in the patch PA, any substance captured in the patch PA at a time point at which a reaction in the patch PA is activated may react in the patch PA. Further, a substance injected after the manufacturing of the patch PA may also act as a reaction initiator.

The providing of a reaction region for a reaction related to the liquid substance SB captured in the patch PA may be a concept subordinate, in terms of embodiment, to the above-described Section 2.1.3 (that is, providing of reaction space). Alternatively, the providing of a reaction region for a reaction related to the liquid substance SB captured in the patch PA may consist of multiple concepts that perform combined functions of the above-described Section 2.1.3 and Section 2.2.4.2 (that is, absorption). The providing of a reaction region for a reaction related to the liquid substance SB captured in the patch PA is not limited thereto and may be implemented in the form in which two or more functions are combined.

3.1.1 First Embodiment

Hereinafter, description will be given by assuming that the function of absorption into the patch PA and the function of providing of a reaction space (hereinafter referred to as "providing function") are performed by a single patch PA. In this case, the absorption function and the providing function may be simultaneously-performed functions, functions performed at different time points, or functions sequentially performed to perform another function. The patch PA further including other functions in addition to the absorption and providing functions may also be considered as belonging to the present embodiment.

As described above, the patch PA may perform a function of capturing a substance, and the substance may have fluidity even when the substance is captured. When some components of the liquid substance SB are non-uniformly distributed, the non-uniform components may be diffused. Even when components of the liquid substance SB are uniformly distributed, the liquid substance SB may have a predetermined level of mobility due to irregular motion of particles. In this case, a reaction between substances, for example, specific binding between substances, may occur inside the patch PA.

For example, in the patch PA, in addition to a reaction between captured substances, a reaction in a form in which a substance having fluidity that is newly captured in the patch PA and the substance that has been captured in the patch PA bind specifically to each other may also be possible.

The reaction between the substance having fluidity and the substance that has been captured in the patch PA may also occur after the substance patch being separated from an space that has been provided. For example, after the patch PA absorbs the substance having fluidity from an arbitrary space, the patch PA may be separated from the arbitrary space, and a reaction between the absorbed substance and the substance that has been captured in the patch PA may occur in the patch PA.

In addition, the patch PA may allow a reaction of a substance captured therein to occur by performing the absorption function with respect to a substance having fluidity. In other words, the absorption of the substance having fluidity by the patch PA may act as a trigger for a reaction between the absorbed substance and the substance that has been captured in the patch PA. The reaction may occur inside a space defined by the patch PA.

A composition of the liquid substance SB captured in the patch PA may be changed due to the reaction occurring inside the patch PA. When, particularly, a substance captured inside the patch PA is a compound, a chemical composition thereof may be changed before and after a reaction. Alternatively, a composition distribution of a substance may be changed in accordance with a position of the substance in the patch PA. For example, this may be due to diffusion or particles having an attractive force specific to another substance.

When the composition of the liquid substance SB is changed due to a reaction inside the patch PA, a portion of the substance may be absorbed into the patch PA due to a concentration difference between the patch PA and a substance outside the patch PA (when a substance in contact with the patch PA is present, the corresponding substance), or the substance may be released from the patch PA to the substance outside the patch PA.

3.1.2 Second Embodiment

Hereinafter, an embodiment in which the containing function of the patch PA and the function of providing of a reaction space for a substance are performed together for at least a predetermined amount of time will be described. More specifically, the patch PA may perform a function of providing a space for at least a portion of the liquid substance SB contained in the patch PA to react.

The patch PA may contain a substance and provide a reaction space for the contained substance. In this case, the reaction space provided by the patch PA may be the microcavities formed by the mesh structural body NS of the patch PA or a surface region of the patch PA. Particularly, when a substance contained in the patch PA and a substance applied on a surface of the patch PA react, the reaction space may be the surface region of the patch PA.

The reaction space provided by the patch PA may serve to provide a specific environmental condition. While a reaction occurs in the liquid substance SB placed in the patch PA, an environmental condition of the reaction may be adjusted by the patch PA. For example, the patch PA may serve as a buffer solution.

By containing a substance through a mesh structure, the patch PA does not require a container, separately. When the reaction space of the patch PA is a surface of the patch PA, a reaction may be easily observed through the surface of the patch PA. For this, the shape of the patch PA may be deformed into a shape that facilitates the observation.

The liquid substance SB contained in the patch PA may be denaturalized or react with a different type of substance. The composition of the liquid substance SB contained in the patch PA may be changed with time.

The reaction may refer to a chemical reaction in which a chemical formula is changed, a physical state change, or a biological reaction. In this case, the liquid substance SB contained in the patch PA may be a substance formed of a single component or a mixture including a plurality of components.

3.2 Providing of Movement Path (Channeling)

Hereinafter, the patch PA that performs a function of providing a substance movement path will be described. More specifically, as described above, the patch PA may capture, absorb, release, and/or contain a substance having fluidity. Various embodiments of the patch PA that performs the function of providing a substance movement path may be implemented by each of the above-described functions of the patch PA or a combination thereof. However, a few embodiments will be disclosed for a better understanding.

3.2.1 Third Embodiment

The patch PA may be implemented to perform functions described in Section 2.2.4.1 (that is, the section related to delivery) and Section 2.2.4.2 (that is, the section related to absorption) among the above-described functions of the patch PA. In this case, the absorption function and the delivery function may be provided together or sequentially provided.

The patch PA may perform the absorption and delivery functions together to provide a substance movement path. Particularly, the patch PA may absorb an external substance and provide the absorbed external substance to an external region, thereby providing a movement path to the external substance.

The providing of the movement path of the external substance by the patch PA may be performed by absorbing the external substance and releasing the external substance. More specifically, the patch PA may come into contact with the external substance, absorb the external substance, come into contact with the external region, and deliver the external substance to the external region. In this case, the capturing of the external substance and the delivery of the captured external substance to the external region by the patch PA may be performed through a process similar to those of the above-described absorption and delivery.

The external substance absorbed into the patch PA and provided may be in a liquid phase or a solid phase.

In this way, the patch PA may allow a portion of the external substance to be provided to another external substance. The external substance and the other external substance may simultaneously come into contact with the patch PA. The external substance and the other external substance may come into contact with the patch PA at different time points.

The external substance and the other external substance may come into contact with the patch PA at different time points. When the external substances come into contact with the patch PA at different time points, the external substance may come into contact with the patch PA first, and after the external substance and the patch PA are separated, the patch PA and the other external substance may come into contact. In this case, the patch PA may temporarily contain a substance captured from the external substance.

The patch PA may simultaneously provide a substance movement path and additionally provide a time delay. The patch PA may perform a function of suitably adjusting an amount of substance provided to another external substance and a speed of such providing.

Such a series of processes may be carried out in one direction with respect to the patch PA. As a specific example, absorption of a substance may be performed through a surface of the patch PA, an environment may be provided in an inner space of the patch PA, and the substance may be released through another surface facing the surface.

3.2.2 Fourth Embodiment

The patch PA may perform the absorbing and releasing of a substance among the above-described functions of the patch PA and the providing of a reaction space for the substance simultaneously. In this case, the absorption and release of the substance and the providing of the reaction space may be performed simultaneously or sequentially.

According to an embodiment, in performing the processes of absorbing and releasing an external substance, the patch PA may provide a reaction space to the absorbed external substance for at least a predetermined amount of time. The patch PA may provide a specific environment for at least some time to the liquid substance SB captured in the patch PA, including the absorbed external substance.

The liquid substance SB that has been captured in the patch PA and the external substance captured in the patch PA may react inside the patch PA. The external substance absorbed into the patch PA may be affected by an environment provided by the patch PA. The substance released from the patch PA may include at least a portion of a substance generated through the reaction. The external substance may be released from the patch PA after the composition, characteristics, and the like of the external substance are changed.

The absorbed substance may be released from the patch PA. The external substance being absorbed into the patch PA and being released from the patch PA may be understood as the external substance passing through the patch PA. The external substance that has passed through the patch PA may lose integrity due to a reaction inside the patch PA or an influence of an environment provided by the patch PA.

The above-described processes of absorption of an external substance, reaction of a substance, and providing of the substance may be carried out in one direction. In other words, the absorption of a substance may be performed at one position of the patch PA, the providing of an environment may be performed at another position of the patch PA, and the release of the substance may be performed at yet another position of the patch PA.

Figure 26:
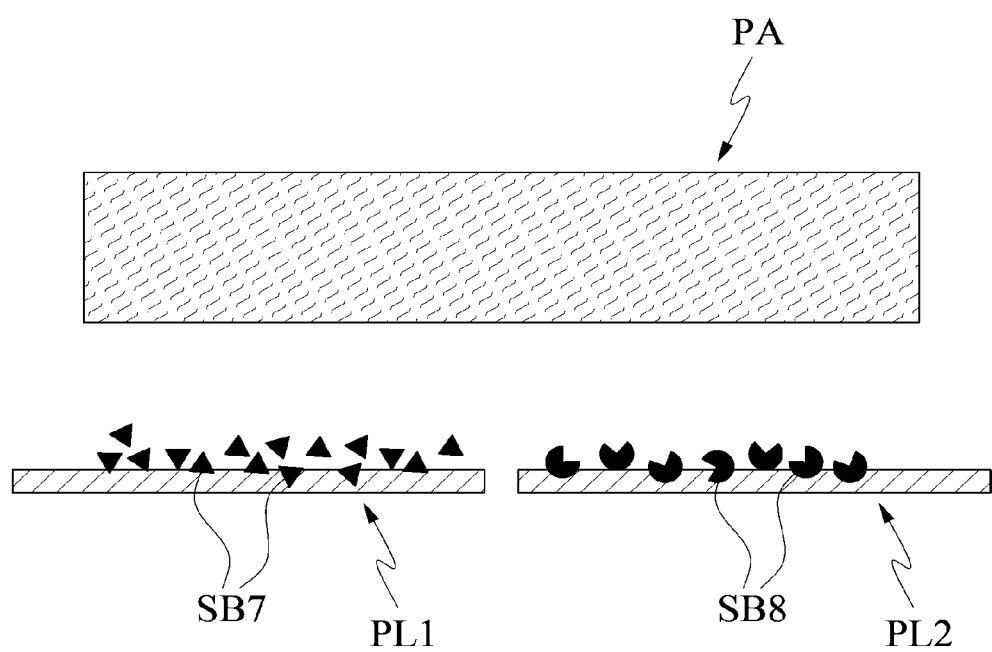
FIG. 26 illustrates performance of absorbing and providing of a substance as an embodiment of a patch according to the present application.
Figure 27:
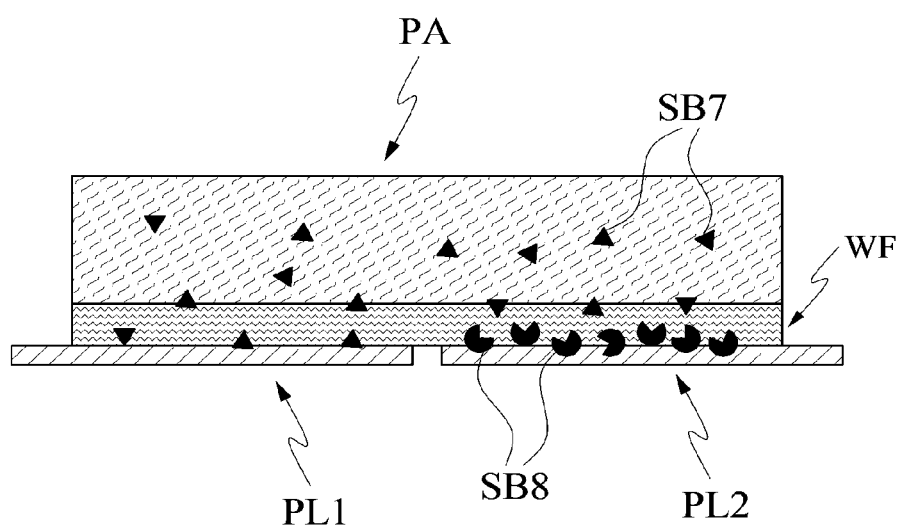
FIG. 27 illustrates performance of absorbing and providing of a substance as an embodiment of a patch according to the present application.
Figure 28:
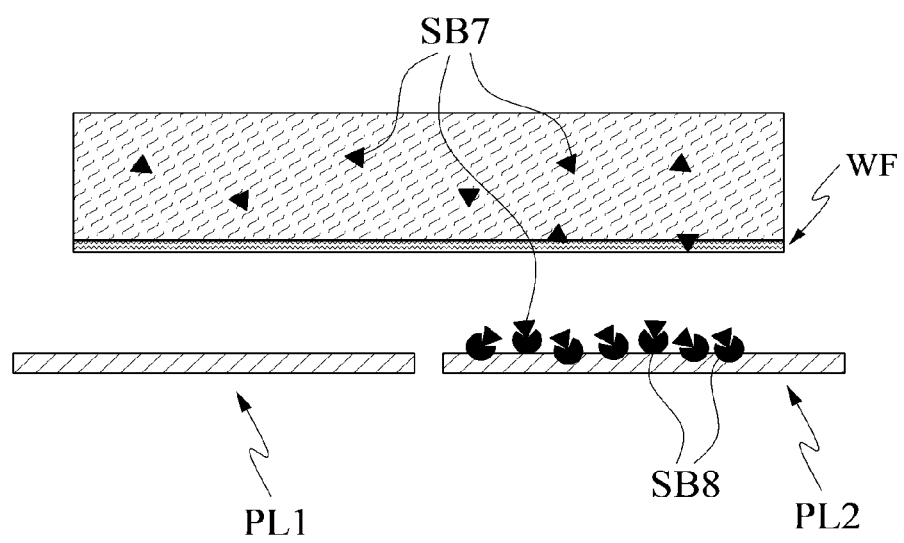
FIG. 28 illustrates performance of absorbing and providing of a substance as an embodiment of a patch according to the present application.

FIGS. 26 to 28 illustrate providing of a substance movement path between two plates PL as an embodiment of the patch PA according to the present application. According to FIGS. 26 to 28, the patch PA may provide a substance movement path between a plate PL1 on which a seventh substance SB7 is applied and a plate PL2 on which an eighth substance SB8 is applied. As a specific example, when the seventh substance SB7 is capable of binding to the eighth substance, and the eighth substance is fixed to the plate PL2, the patch PA may come into contact with the plates PL1 and PL2 so that the seventh substance SB7 is moved through the patch PA and bound to the eighth substance SB8. The seventh substance SB7 and the eighth substance SB8 may be connected to the patch PA through a water film WF formed by the patch PA coming into contact with the plates PL1 and PL2.

Figure 29:
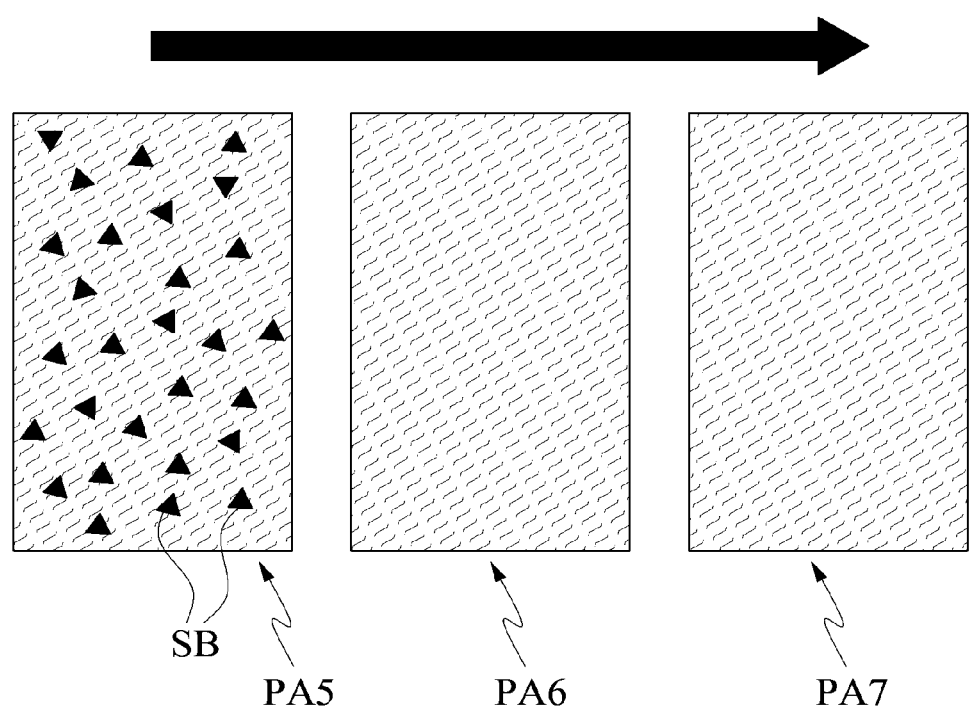
FIG. 29 illustrates performance of absorbing and providing of a substance as an embodiment of a patch according to the present application.
Figure 30:
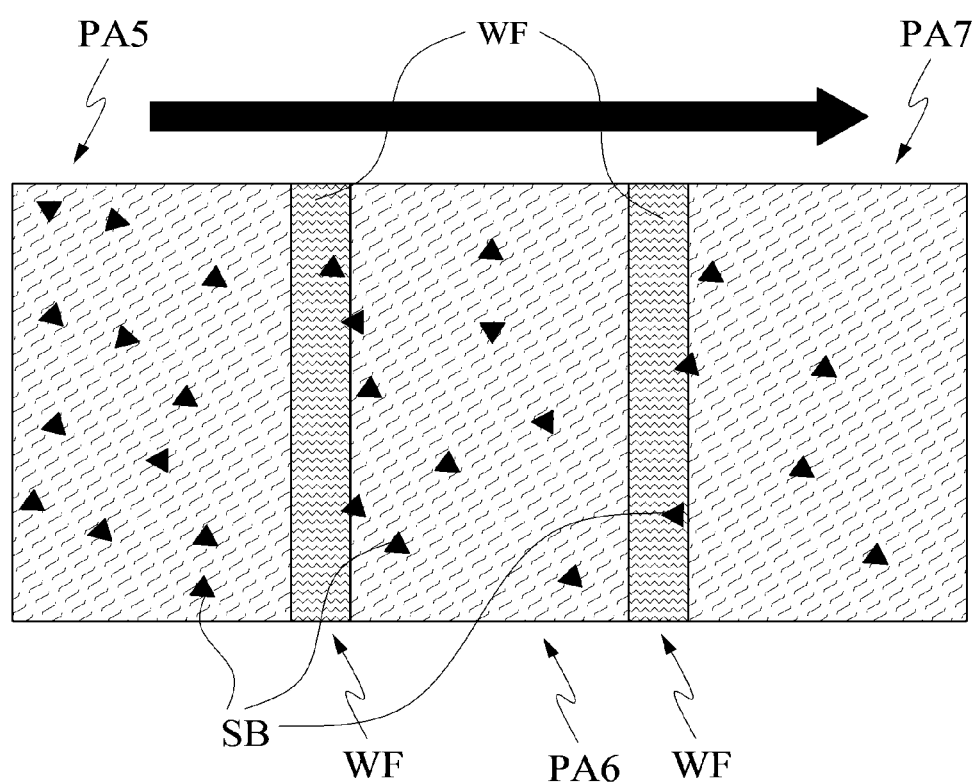
FIG. 30 illustrates performance of absorbing and providing of a substance as an embodiment of a patch according to the present application.

FIGS. 29 and 30 illustrate providing of a substance movement path between two patches as an embodiment of the patch PA according to the present application. According to FIGS. 29 and 30, a patch PA6 configured to provide the movement path may be in contact with a patch PA5 configured to contain a substance to be moved, and a patch PA7 configured to receive the substance to be moved. The patch PA6 configured to provide the movement path may come into contact with the patch PA5 configured to contain the substance to be moved and the patch PA7 configured to receive the substance to be moved, and the substance to be moved may be moved to the patch PA7 configured to receive the substance to be moved. The movement of the substance between the patches may be performed by a water film WF formed in the vicinity of a contact region between the patches.

Figure 31:
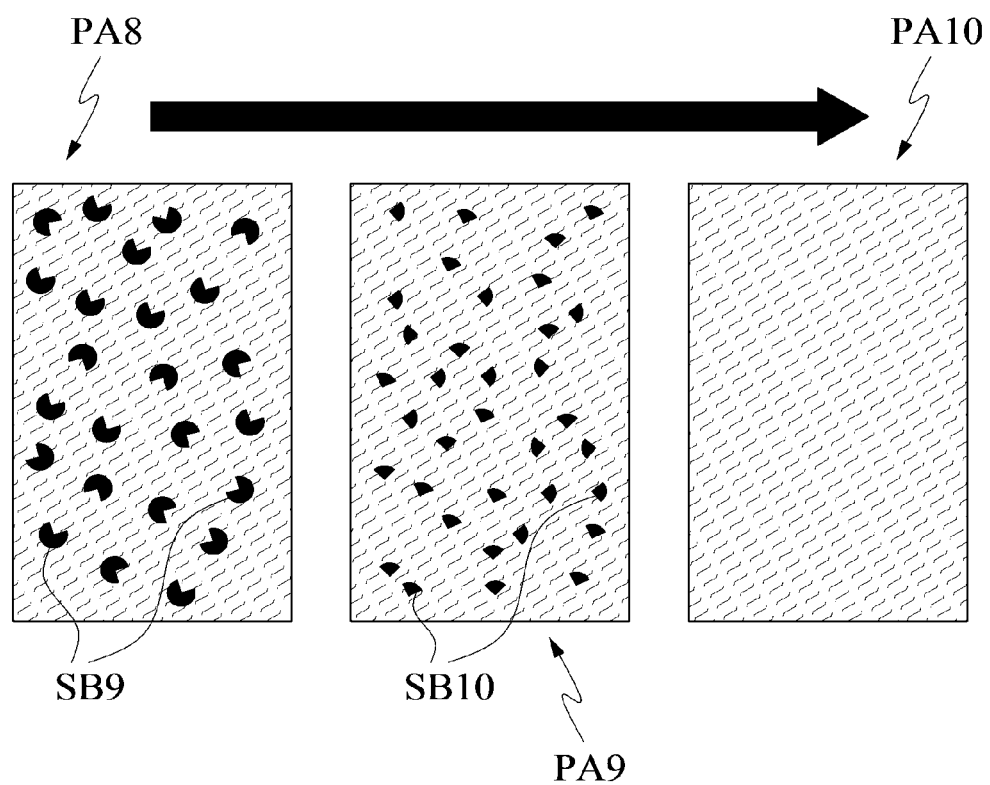
FIG. 31 illustrates performance of absorbing and providing of a substance and providing of an environment as an embodiment of a patch according to the present application.
Figure 32:
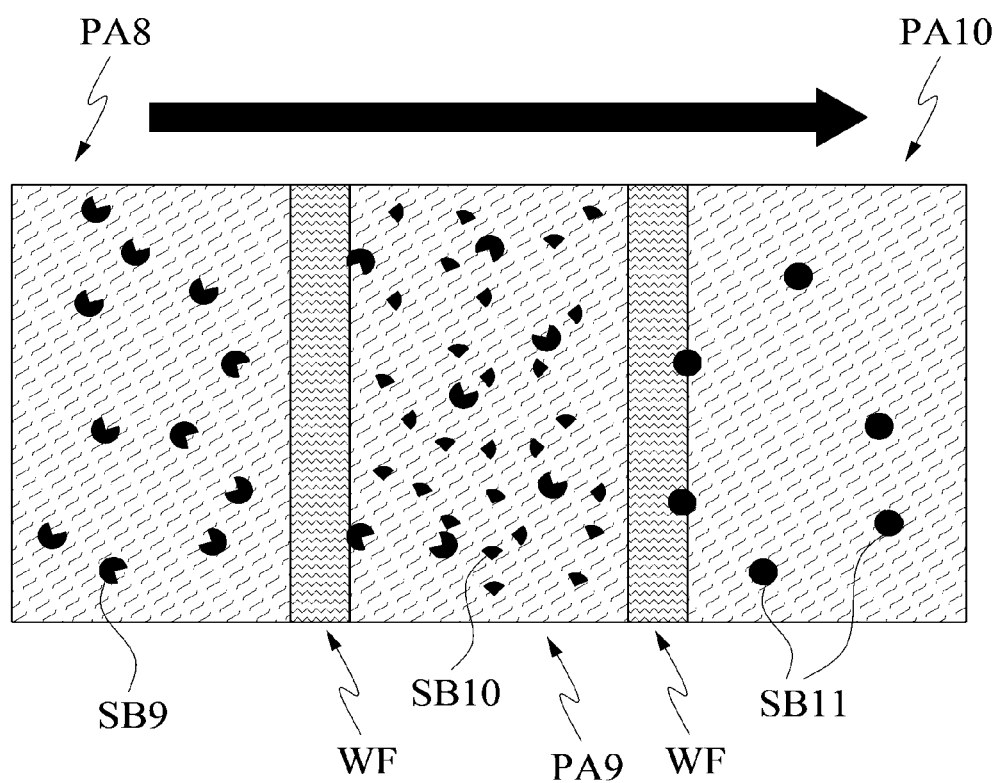
FIG. 32 illustrates performance of absorbing and providing of a substance and providing of an environment as an embodiment of a patch according to the present application.

FIGS. 31 and 32 illustrate providing of a substance movement path between two patches as an embodiment of the patch according to the present application. According to FIGS. 29 and 30, a patch PA9 configured to provide the movement path may be in contact with a patch PA8 configured to contain a ninth substance SB9 and a patch PA10 configured to receive a substance. The patch PA9 providing the movement path may come into contact with the patch PA8 configured to contain the ninth substance SB9 to absorb the ninth substance SB9. The absorbed ninth substance SB9 may react with a tenth substance SB10 contained in the patch PA9, which is configured to provide the movement path, and generate an eleventh substance. An eleventh substance SB11 may be provided from the patch PA9 configured to provide the movement path to the patch PA10 configured to receive the substance. The movement of a substance between the patches PA may be performed through a water film WF formed in the vicinity of a contact region between the patches PA.

3.3 Multi-Patch

A patch PA may be solely used, or a plurality of patches PA may be used together. In this case, the plurality of patches PA being able to be used together includes a case in which the plurality of patches PA are sequentially used as well as a case in which the plurality of patches PA are used simultaneously.

When the plurality of patches PA are used simultaneously, the patches PA may perform different functions. Although each patch PA of the plurality of patches PA may contain the same substance, the plurality of patches PA may also contain different substances.

When the plurality of patches PA are used simultaneously, the patches PA may not come into contact with each other such that substance movement does not occur between the patches PA, or a desired function may be performed in a state in which substances contained in the patches PA are exchangeable.

Although the plurality of patches PA used together may be manufactured in shapes similar to each other or in the same size, the plurality of patches PA may be used together even when the plurality of patches PA have different shapes. Each patch PA constituting the plurality of patches PA may be manufactured such that densities of the mesh structural bodies NS are different or components constituting the mesh structural bodies NS are different.

3.3.1 Contact with Plurality of Patches

When a plurality of patches PA are used, the plurality of patches PA may come into contact with a single target region TA. The plurality of patches PA may come into contact with the single target region TA and perform a desired function.

When a plurality of target regions TA are present, the plurality of patches PA may come into contact with different target regions TA. When the plurality of target regions TA are present, the plurality of patches PA may respectively come into contact with corresponding target regions TA and perform a desired function.

The plurality of patches PA may come into contact with a substance applied on the target region TA. In this case, the substance applied on the target region TA may be fixed or have fluidity.

The desired function may be a function of providing or absorbing the substance. However, each patch PA does not necessarily provide the same substance or absorb the same substance, and the patches PA may provide different substances to the target region TA or absorb different components from a substance placed in the target region TA.

The desired function may be different for each patch PA constituting the plurality of patches PA. For example, one patch PA may perform the function of providing a substance to the target region TA, and another patch PA may perform the function of absorbing the substance from the target region TA.

The plurality of patches PA may include different substances, and the different substances may be provided to a single target region TA and used to induce a desired reaction. When a plurality of components of a substance is required for the desired reaction to occur, the plurality of components may be contained in a plurality of patches PA respectively and provided to the target region TA. Such use of the plurality of patches PA may be particularly useful when properties of substances required for a desired reaction are lost or altered when the substances required for the reaction being mixed for reasons such as being contained in a single patch PA.

According to an embodiment, when the plurality of patches PA include substances formed of different components, and the substances formed of different components have different specific binding relationships, the substances formed of different components may be provided to the target region TA. The plurality of patches PA may be used to detect a plurality of specific bindings from the substances applied on the target region TA, by providing the substances including different components.

According to another embodiment, the plurality of patches PA may include substances formed of the same component, but each patch PA may have a different concentration with respect to the substance formed of the same component. The plurality of patches PA including the substances formed of the same component may come into contact with the target region TA and be used to determine an influence in accordance with a concentration of the substance included in the plurality of patches PA.

When the plurality of patches PA are used as described above, the patches PA may be grouped into more efficient forms and used. In other words, the configuration of the plurality of patches PA being used may be changed every time the plurality of patches PA are used. The plurality of patches PA may be manufactured in the form of a cartridge and used. In this case, the form of each patch PA being used may be suitably standardized and manufactured.

The plurality of patches PA in the form of a cartridge may be suitable when patches PA configured to contain a plurality of types of substances are manufactured to be used by being chosen as necessary.

Particularly, when attempting to detect a specific reaction of each substance from the target region TA using a plurality of types of substances, a combination of specific reactions to be detected may be changed every time the detection is performed.

Figure 33:
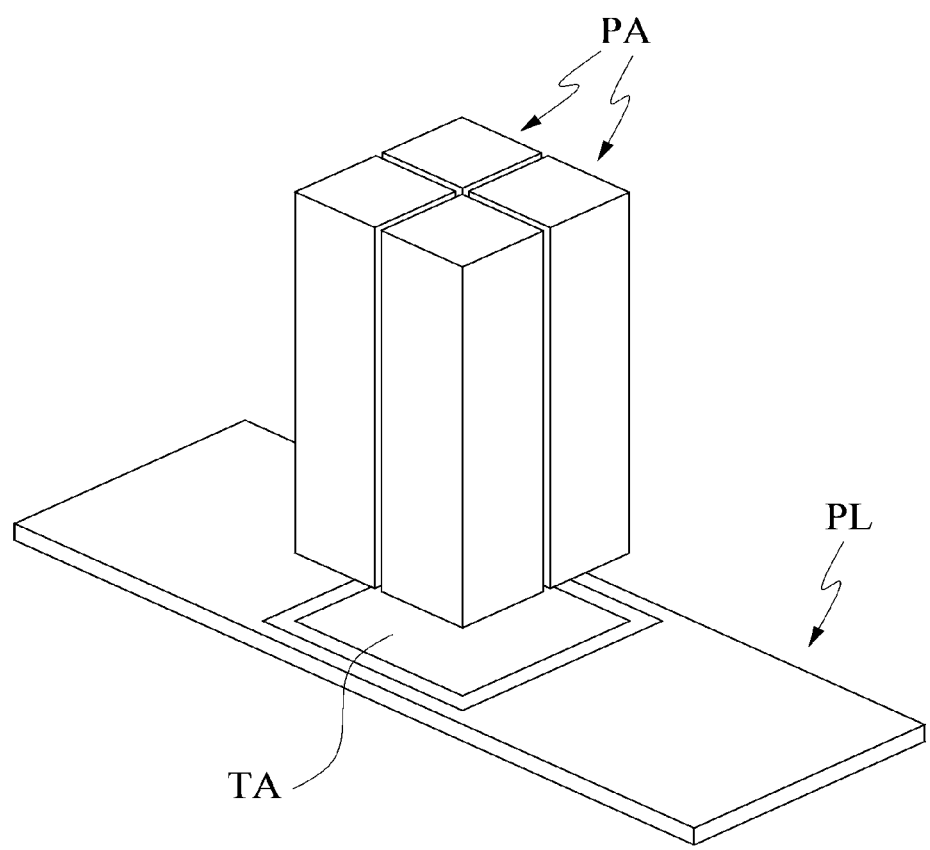
FIG. 33 illustrates an implementation of a plurality of patches as an embodiment of a patch according to the present application.

FIG. 33 illustrates a case in which the plurality of patches PA are used together as an embodiment of the patch PA according to the present application. According to FIG. 33, the plurality of patches PA according to an embodiment of the present application may simultaneously come into contact with a target region TA placed on a plate PL. The patches PA constituting the plurality of patches PA may have a standardized form. The plurality of patches PA may include a first patch and a second patch, and a substance contained in the first patch may be different from a substance contained in the second patch.

Figure 34:
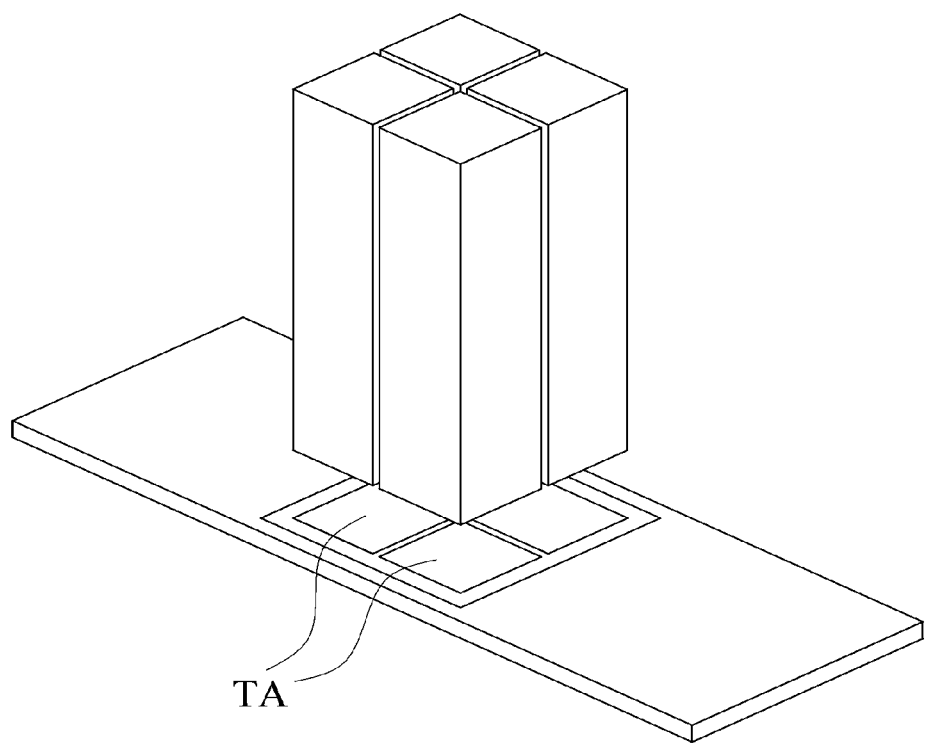
FIG. 34 illustrates an implementation of a plurality of patches and a plate having a plurality of target regions as an embodiment of a patch according to the present application.

FIG. 34 illustrates a case in which the plurality of patches PA are used and the plate PL includes a plurality of target regions TA. According to FIG. 34, the plurality of patches PA according to an embodiment of the present application may simultaneously come into contact with the plurality of target regions TA placed on the plate PL. The plurality of patches PA may include a first patch PA and a second patch PA, the plurality of target regions TA may include a first target region and a second target region, and the first patch may come into contact with the first target region and the second patch may come into contact with the second target region.

3.3.2 Fifth Embodiment

The plurality of patches PA may perform a plurality of functions. As described above, the patches PA may simultaneously perform a plurality of functions, and the patches PA may also simultaneously perform different functions. However, embodiments are not limited to the above, and the functions may also be combined and performed in the plurality of patches PA.

First, in the case in which the patches PA simultaneously perform the plurality of functions, the patches PA may perform both containing and release of a substance. For example, the patches PA may contain different substances and release substances contained in the target regions TA. In this case, the contained substances may be simultaneously or sequentially released.

Next, in the case in which the patches PA simultaneously perform different functions, the patches PA may separately perform containing and release of a substance. In this case, only some of the patches PA may come into contact with a target region TA and release a substance to the target region TA.

3.3.3 Sixth Embodiment

When a plurality of patches PA are used, as described above, the plurality of patches PA may perform a plurality of functions. First, the patches PA may simultaneously perform containing, releasing, and absorbing of substances. Alternatively, the patches PA may also separately perform the containing, releasing, and absorbing of the substances. However, embodiments are not limited thereto, and the functions may also be combined and performed in the plurality of patches PA.

For example, at least some of the plurality of patches PA may contain a substance and release the contained substance to the target region TA. In this case, at least a remainder of the plurality of patches PA may absorb a substance from the target region TA. Some of the plurality of patches PA may release a substance that binds specifically to a substance placed in the target region TA. In this case, specific binding may be detected by absorption of a substance that has not formed specific binding from the substance placed in the target region TA using another patch PA.

3.3.4 Seventh Embodiment

When a plurality of patches PA are used, the patches PA may simultaneously perform containing and release of a substance and providing of an environment. Alternatively, the patches PA may separately perform the containing and release of a substance and providing of an environment. However, embodiments are not limited thereto, and the functions may also be performed in combination in the plurality of patches PA.

For example, a patch PA among the plurality of patches PA may release a substance contained therein to the target region TA. In this case, another patch PA may provide an environment to the target region TA. Here, the providing of an environment may be implemented in the form in which an environmental condition of a substance contained in the other patch PA is provided to the target region TA. More specifically, a reacting substance may be provided to the target region TA by the patch PA, and the other patch PA may come into contact with the target region TA and provide a buffering environment.

As another example, the plurality of patches PA may be in contact with each other. In this case, at least one patch PA may contain a substance and release the substance contained therein to another patch PA configured to provide an environment. In the present embodiment, the patch PA configured to provide an environment may release a substance, come into contact with at least one other patch PA that is not in contact with the patch PA configured to provide an environment, and absorb a substance from the patch PA.

4 Immunoassay 4.1 Meaning

The patch of the present application may be used in an immunoassay. Immunoassay refers to performing diagnosis in accordance with a test result obtained through an immunological technique. As an example of immunoassay, Enzyme-Linked Immunosorbent Assay (hereinafter, "ELISA") is mainly used.

Hereinafter, unless particularly described otherwise, it will be assumed that description herein is about immunoanalysis for the purpose of diagnosis. However, it is obvious that the technical spirit of the disclosure and embodiments described herein may be applied throughout the field of analysis (that is, immunoanalysis) using an antigen-antibody reaction, in addition to being applied to practices for the purpose of diagnosis.

In applying the patch of the present application to immunoassay, the above-described basic substance BS and the additive substance AS may be suitably changed in accordance with a site to which the patch is applied.

Prior to examining specific embodiments, the types of immunoassay and methods of performing the same will be examined.

4.1.1 Classification of Immunoassay

Immunoassay may be classified in accordance with various standards.

Immunoassay may be classified, in accordance with methods of performing the same, into: 1) a direct technique (or direct ELISA) in which an antigen is fixated on a plate PL and an enzyme is directly bound to an antibody which reacts with the antigen so that an amount of antigen is detected; 2) an indirect technique (or indirect ELISA) in which an antigen is fixated on a plate and a primary antibody which reacts with the antigen and a secondary antibody which bind to the primary antibody and has an enzyme bound thereto are used to detect an amount of antigen; 3) a sandwich technique (or sandwich ELISA) in which an antibody related to an antigen is fixated on a plate PL first, the antigen is bound to the antibody, and the direct technique or the indirect technique is used to detect the antigen; and 4) a competitive quantitative technique (or competitive ELISA) in which two antigens that compete for the same binding portion of an antibody are used to measure a concentration of an antigen. Immunoassay may also be classified in accordance with target samples.

Immunoassay may be classified as an immunochemical technique when a target sample is a bodily fluid, an immunocytochemical technique when a sample is cells, and as an immunohistochemical technique when a sample is a tissue. Immunoassay on a bodily fluid may be used in diagnosis through detection of target proteins such as antigens that float Immunoassay on cells may be used in detection of target proteins such as antigens present on surfaces of or inside cells. Immunoassay on a tissue may be performed by detecting target proteins present on surfaces of or inside cells or determining distribution of target proteins in the tissue.

Immunoassay may also be classified in accordance with detection methods. There is a method in which color development due to a product of an enzyme-substrate reaction is observed (colorimetric), a method in which luminescence due to a chemical reaction is detected (chemiluminescence), and a method in which fluorescence is detected (chemifluorescence). When color development is measured, a spectrophotometer is mostly used. When fluorescence is measured, a fluorometer on which a filter is mounted is mostly used, and when luminescence is measured, a luminometer is mostly used.

4.1.2 ELISA

ELISA is an example of immunoassay and refers to a diagnostic method for detecting a substance, in particular, an antigen. More specifically, ELISA refers to a method in which an antibody or an antigen is attached to an enzyme and an activity of the enzyme is measured to quantitatively measure a strength of an antigen-antibody reaction and an amount thereof. Since an antibody or an antigen may be attached onto a solid phase object and free, unbound antigens or antibodies may be removed through washing according to ELISA, ELISA facilitates detection of a desired result. Hereinafter, unless particularly mentioned otherwise, immunoassay is assumed to be referring to immunoassay using ELISA.

4.2 Performance of Immunoassay 4.2.1 Preparation for Sample 4.2.1.1 Types of Sample Samples used in an immunoassay may be mainly classified into bodily fluids, cells, and tissues, each of which may require a process of being appropriately processed for use.

Bodily fluid samples used in an immunoassay may include blood, urine, saliva, and the like. Particularly, for blood, although whole blood may be used, blood may also be separated into serums, plasmas, blood cells and the like, and each of the components of blood may be used for detection.

Cell samples used in an immunoassay may include whole blood, cultured cells, cell suspensions, and the like.

Hereinafter, unless particularly mentioned otherwise, it will be assumed that a sample is a tissue in an immunoassay according to the present application.

4.2.1.2 Preparation of Each Type of Sample

Preparation of a sample used in an immunoassay will be described. A method of preparing a sample used in diagnosis may differ in accordance with a method of performing diagnosis. Hereinafter, a case in which the patch PA of the present application is used and diagnosis is performed on a sample located on a plate PL will be described.

Here, "plate PL" may refer to a general slide glass or a solid plate such as a plate manufactured with polystyrene, polypropylene or the like. A form of a bottom or transparency of the plate PL may be different in accordance with a detection methods. For example, in a case that light is desired to be detected, a white plate or a black plate may be used as the plate PL. Also, for example, in a case that color development is desired to be detected, a transparent plate with a flat bottom may be used as the plate PL. The plate PL may include a reaction region which contact with the patch PA or in which a desired reaction may occur.

When immunoassay is performed on bodily fluid, the bodily fluid may be used in diagnosis in a state in which the bodily fluid is fixated on the plate PL. In other words, the bodily fluid may be used in a state in which the bodily fluid is smeared on the plate PL and fixated thereto. Alternatively, the bodily fluid may be used in a state in which the bodily fluid is smeared on the plate PL. For example, the bodily fluid may be smeared on the plate PL to which an antibody is fixated.

When immunoassay is performed on cells, blood or suspensions of the cells may be smeared on the plate PL and dried to perform diagnosis. Alternatively, blood or suspensions of the cells may be smeared on the plate PL and used. For example, blood or suspensions of the cells may be smeared on the plate PL to which an antibody is fixated, and diagnosis may be performed. When immunoassay is performed on cells, diagnosis may be performed on cells that have gone through cytolysis or cells that have not gone through cytolysis.

When immunoassay is performed on tissues, a section or thin piece of tissue may be placed on the plate PL, and diagnosis may be performed. A section of tissue may be a section of tissue filled with paraffin or a frozen section of tissue.

4.2.2 Preparation for Patch

In performing immunoassay in the present application, the above-described patch PA may be used.

The patch PA may contain an antigen and provide the antigen to the plate PL. The patch PA may also contain a biopsy specimen, i.e., sample, that includes an antigen and provide the biopsy specimen to the plate PL.

The patch PA may contain an antibody AB and deliver the antibody AB to the plate PL. When an indirect technique is used, the antibody AB contained in the patch PA may be a primary antibody AB or a secondary antibody AB. In other words, the patch PA may contain the primary antibody AB or the secondary antibody AB. Further, the patch PA may also simultaneously contain the primary antibody AB and the secondary antibody AB and provide the primary antibody AB and the secondary antibody AB to the plate PL. The antibody AB may also be contained in the patch in a state being attached to a particle.

The patch PA may contain a substrate SU that performs a reaction catalyzed by the enzyme and provide the substrate SU to the plate PL. The substrate SU used may vary in accordance with an enzyme being used and a detection means. The substrate SU may be a 2,2'-Azino-bis (3-ethylbenzothiazoline-6-sulfonic acid (ABTS)), 3,3',5,5'-Tetramethylbenzidine (TMB), or the like.

The patch PA may contain a washing solution and absorb residue from the plate PL. Impurities on the plate PL or an antibody AB that has not bound specifically may be absorbed and removed from the plate PL by the patch PA containing the washing solution being brought into contact with the patch PA and then separated therefrom. The washing solution used above may be a tris buffered saline (TBS) or phosphate buffered saline (PBS) with Tween 20.

The patch PA may contain a buffer solution and provide an environment for the plate PL. In this case, the buffer solution may serve to facilitate each step of the immunoassay. Therefore, a buffer solution used in each step may contain different components. As an example of the buffer solution, a peroxide buffer may be used when detecting chemiluminescence.

The patch PA may contain an interruption solution for interrupting a substrate SU-enzyme reaction. That is, a reaction interruption patch PA may be manufactured, and the interruption solution may be provided to the plate PL using the reaction interruption patch PA to interrupt a substrate SU-enzyme reaction at an appropriate time point.

Performance of immunoassay using the patch PA will be described in detail below.

4.2.3 Methods of Immunoassay

A few typical examples of a methods of performing immunoassay using the patch PA and the plate PL of the present application as described above will be described.

However, the immunoassay method of the present disclosure is not limited to the examples which will be described below, and since a plurality of modified detection methods may be present, any immunoassay method performed using the patch PA may be applied as the immunoassay method of the present disclosure.

4.2.3.1 Direct Case

Immunoassay according to a direct technique may be performed using the patch PA and the plate PL of the present application.

The immunoassay according to a direct technique using the patch PA and the plate PL may be understood as being performed by fixating a sample (antigens) to the plate PL, applying an antibody AB that bind specifically to antigens desired to be detected and have enzymes attached thereto as identification labels, removing antibodies AB that have not bound specifically, and detecting a reaction of a substrate SU catalyzed by the enzymes. In this case, the patch PA according to the present application may be used in the applying of the antibodies AB and removing of the antibodies AB that have not bound specifically.

The above detection method will be described below in detail in "Detection methods of immunoassay" section.

4.2.3.2 Indirect Case

Immunoassay according to an indirect technique may be performed using the patch PA and the plate PL of the present application.

The immunoassay according to an indirect technique using the patch PA and the plate PL may be understood as being performed by fixating a sample (or antigens) to the plate PL, applying an antibody AB (that is, primary antibody AB) that bind specifically to antigens desired to be detected, removing primary antibody AB that have not bound specifically, applying antibodies AB (that is, secondary antibody AB) that bind specifically to the primary antibody AB and have enzymes attached thereto as identification labels, removing secondary antibody AB that have not bound specifically to the primary antibody AB, and detecting a reaction catalyzed by the enzymes on the plate PL. In this case, the patch PA according to the present application may be used in the applying of the antibody AB and removing of the antibody AB that have not bound specifically.

The above detection method will be described below in detail in the "Detection methods of immunoassay" section.

4.2.3.3 Sandwich Case

Immunoassay according to a sandwich technique may be performed using the patch PA and the plate PL of the present application.

The immunoassay according to a sandwich technique using the patch PA and the plate PL may be performed by fixating antibodies AB to the plate PL, applying a sample (or antigens) on the plate PL, applying antibodies AB that bind specifically to antigens desired to be detected, and removing antigens or antibodies AB that have not bound specifically. In this case, the applying of the antibodies AB that bind specifically to the antigens may be performed by the above-described direction technique or indirect technique. In other words, the applying of the antibodies AB that bind specifically to the antigens may be performed by applying antibodies AB that bind specifically to the antigens and have enzymes attached thereto. Alternatively, the applying of the antibodies AB that bind specifically to the antigens may include applying primary antibodies AB that bind specifically to the antigens and applying antibodies AB that react specifically with the primary antibodies AB and have enzymes attached thereto as identification labels. The patch PA according to the present application may be used in the applying of the antibodies AB.

The above detection method will be described below in detail in "Detection methods of immunoassay" section.

4.2.4 Detection Methods of Immunoassay

Detection of a diagnosis result of immunoassay using the patch PA and the plate PL of the present application may be performed using various detection methods.

The detection methods may be selectively used in accordance with a product produced due to a reaction between the enzyme and the substrate SU. In other words, enzymes may have been attached as labels to the antibodies AB in the direct technique or the secondary antibodies AB in the indirect technique, the enzymes attached to the antibodies AB may catalyze a chemical reaction of the substrate SU and generate a product, and a detection method to be used may be determined in accordance with the product generated in this case.

When color development due to the generated product is detected, the color development may be measured to quantitatively measure specific binding. The measuring of the color development may be performed by detecting light that has been emitted from a light source and has passed through the plate PL. In other words, the measuring of the color development may be performed by measuring light absorption. A spectrophotometer may be used when measuring the color development. In this case, preferably, a flat, transparent plate may be used as the plate PL.

In a case that luminescence due to the generated product is desired to be detected, the luminescence may be measured to quantitatively measure specific binding. The measuring of the luminescence may be performed by detecting light emitted from the bottom of the plate PL or a solution thereabove. A luminometer may be used when the luminescence is measured. When the luminescence is measured, an opaque black plate or an opaque white plate may be used as the plate PL.

In a case in which fluorescence due to the generated product is desired to be detected, the fluorescence may be measured to quantitatively measure specific binding. The measuring of the fluorescence may be performed by making light be incident on the plate PL and measuring fluorescence emitted from the plate PL. A fluorometer with a filter attached thereto may be used when the fluorescence is measured. When the fluorescence is measured, an opaque black plate or an opaque white plate may be used as the plate PL.

A color development image, a luminescence image, or a fluorescence image may be acquired. Partial images of an image may be acquired separately, and the acquired partial images may be combined into a single image. Positions at which target antigens/antibodies AB are distributed, shape of cells, distribution of target proteins in a tissue, or the like may be obtained from the acquired images. Also, by analyzing the acquired images, positions of target proteins, target antigens/antibodies AB, or the like and partial images of the targets may be acquired.

Detection of a diagnosis result of the immunoassay may also be performed using an electrochemical method. For example, a change in an electrochemical characteristic that occurs on the plate PL may be measured using the antibodies AB that have bound specifically to a sample fixated on the plate PL. Alternatively, a change in an electrochemical characteristic of the patch PA that occurs due to the patch PA transferring the antibodies AB to the plate PL may also be measured.

4.3 Embodiments of Immunochemistry

Figure 35:
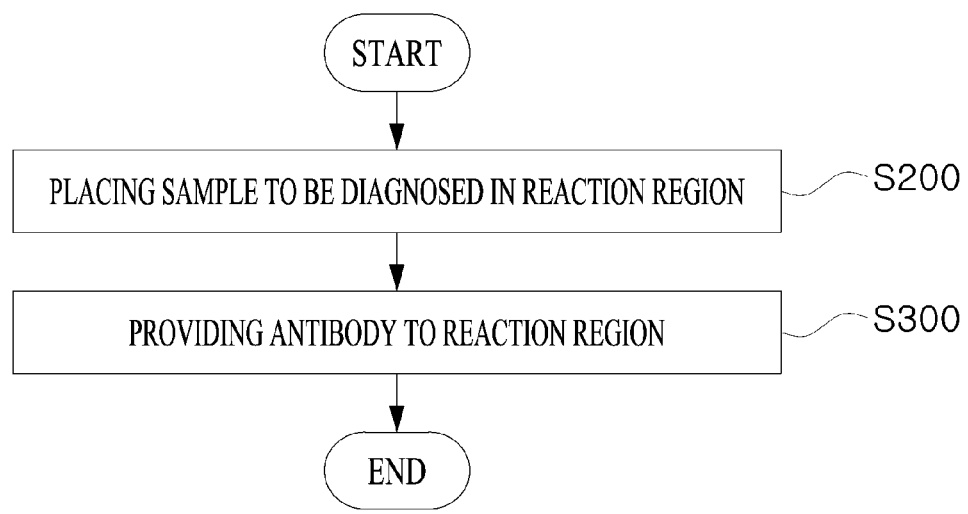
FIG. 35 illustrates a flowchart for describing an example of an immunoassay method according to the present application.

FIG. 35 illustrates a flowchart for describing an example of an immunoassay method according to the present application. An immunoassay method according to an embodiment of the present application may include placing a sample to be diagnosed in a reaction region (S200) and providing an antibody AB to the reaction region using a patch PA that contains antibodies AB that react specifically with target proteins TP(S300).

The placing of the sample to be diagnosed may be performed through any one of a method of fixating the sample to the plate PL, a method of smearing the sample on the plate PL, and a method of smearing the sample on the plate and fixating the sample.

Figure 36:
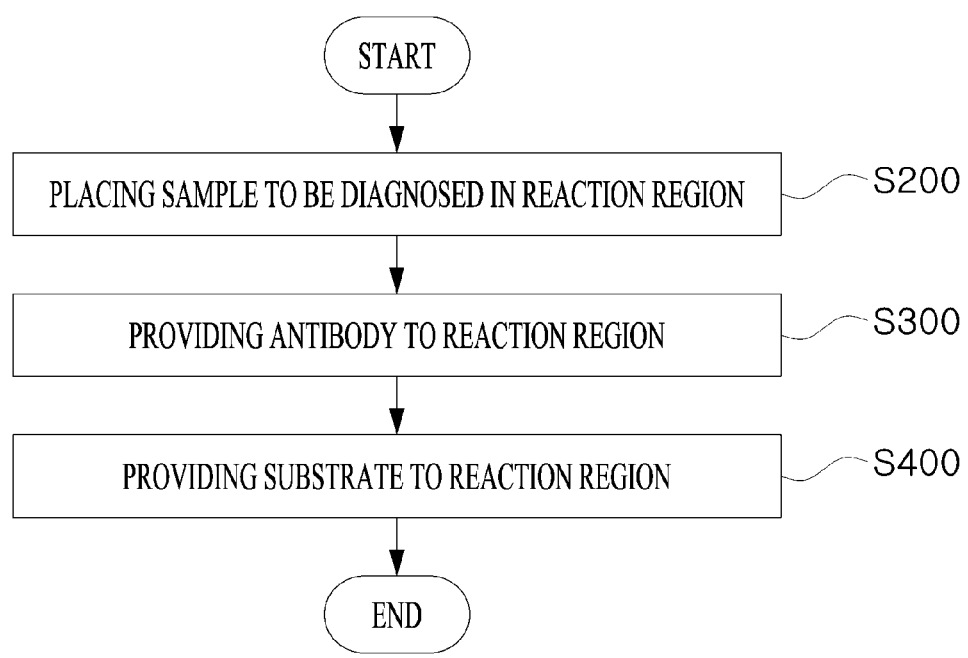
FIG. 36 illustrates a flowchart for describing an example of an immunoassay method according to the present application.

In addition to the placing of the sample (S200) and the providing of the antibodies AB to the reaction region (S300), the immunoassay method may further include providing a substrate SU to the reaction region using a patch PA that contains a substrate SU which generates a product through a chemical reaction catalyzed by enzymes attached to the antibodies AB (S400) (see FIG. 36).

Figure 37:
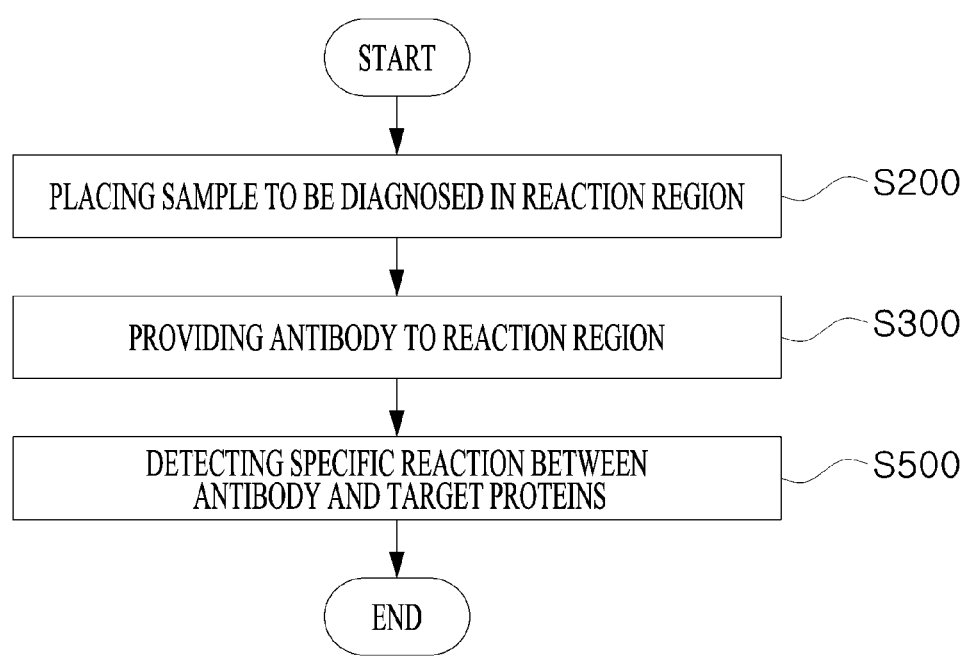
FIG. 37 illustrates a flowchart for describing an example of an immunoassay method according to the present application.

In addition to the placing of the sample (S200) and the providing of the antibodies AB to the reaction region (S300), the immunoassay method may further include detecting a specific reaction between the antibodies AB and the target proteins TP in order to diagnose a target disease (see FIG. 37).

In this case, the detecting of the specific reaction may include measuring a change in an electrical characteristic of the patch PA that occurs due to the specific reaction. Alternatively, the detecting of the specific reaction may be performed by any one of measuring fluorescence that occurs due to a chemical reaction catalyzed by the enzymes attached to the antibodies AB that bind specifically to the target proteins TP, measuring luminescence that occurs due to the chemical reaction, and measuring color that develops due to the chemical reaction.

Figure 38:
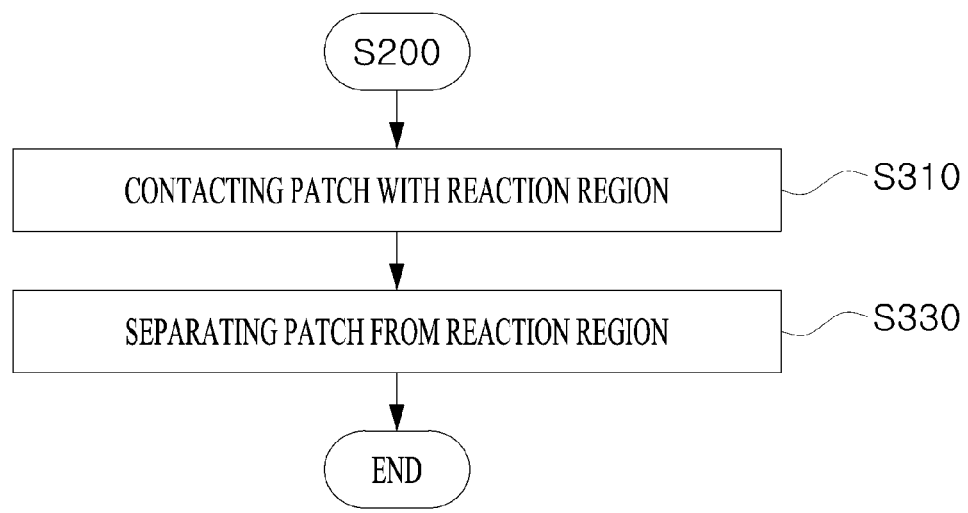
FIG. 38 illustrates a flowchart for describing an example of providing an antibody to a reaction region in an immunoassay method according to an embodiment of the present application.

The providing of the antibodies AB to the reaction region (S300) may include contacting the patch PA with the reaction region so that the antibodies AB are movable to the reaction region (S310) and separating the patch PA from the reaction region (S330), and when the patch PA is separated from the reaction region, antibodies AB that have not reacted specifically with the target proteins TP from among the antibodies AB may be removed from the reaction region (see FIG. 38).

Figure 39:
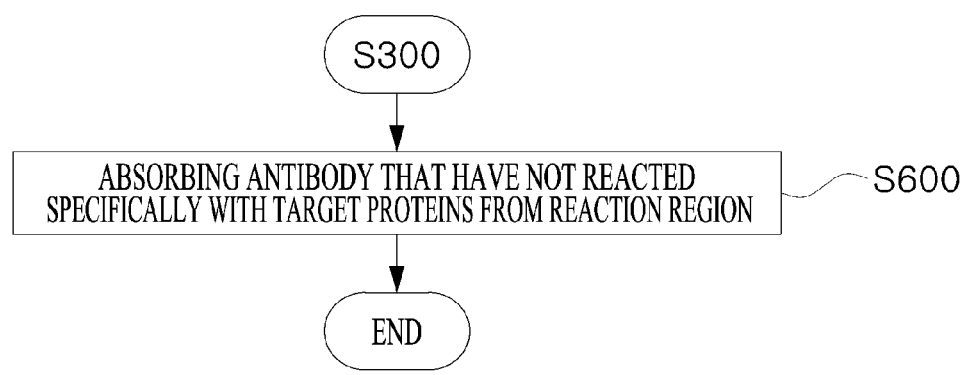
FIG. 39 illustrates a flowchart for describing an example of an immunoassay method according to the present application.

In addition to the placing of the sample (S200) and the providing of the antibodies AB to the reaction region (S300), the immunoassay method may further include absorbing the antibodies AB that have not reacted specifically with the target proteins TP from among the provided antibodies AB from the reaction region by using a washing patch PA (S600) (see FIG. 39).

Figure 40:
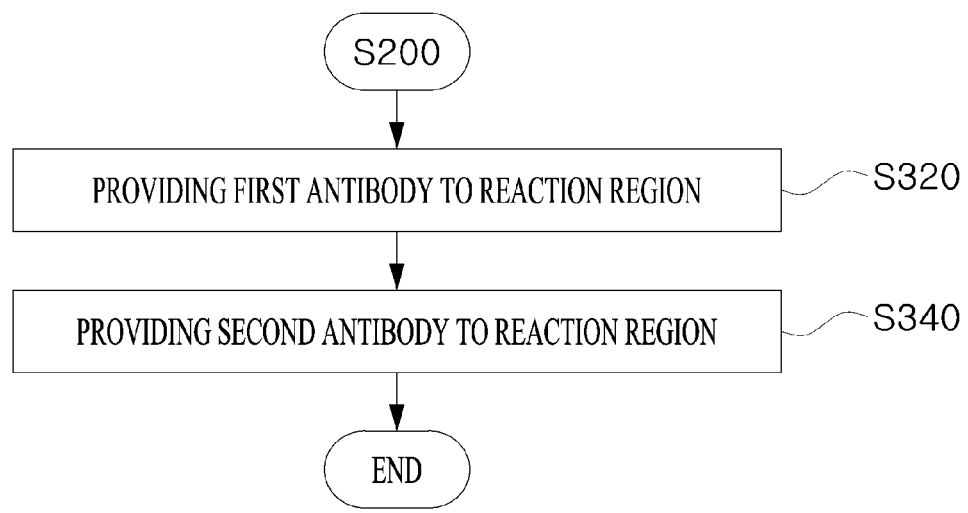
FIG. 40 illustrates a flowchart for describing an example of providing an antibody to a reaction region in an immunoassay method according to an embodiment of the present application.

In the immunoassay method, the providing of the antibodies AB to the reaction region (S300) may include providing first antibodies AB to the reaction region using a first patch PA that contains first antibodies AB that react specifically with the target proteins TP (S320) and providing second antibodies AB to the reaction region using a second patch PA that contains second antibodies AB that react specifically with the first antibodies AB (S340) (see FIG. 40).

Figure 41:
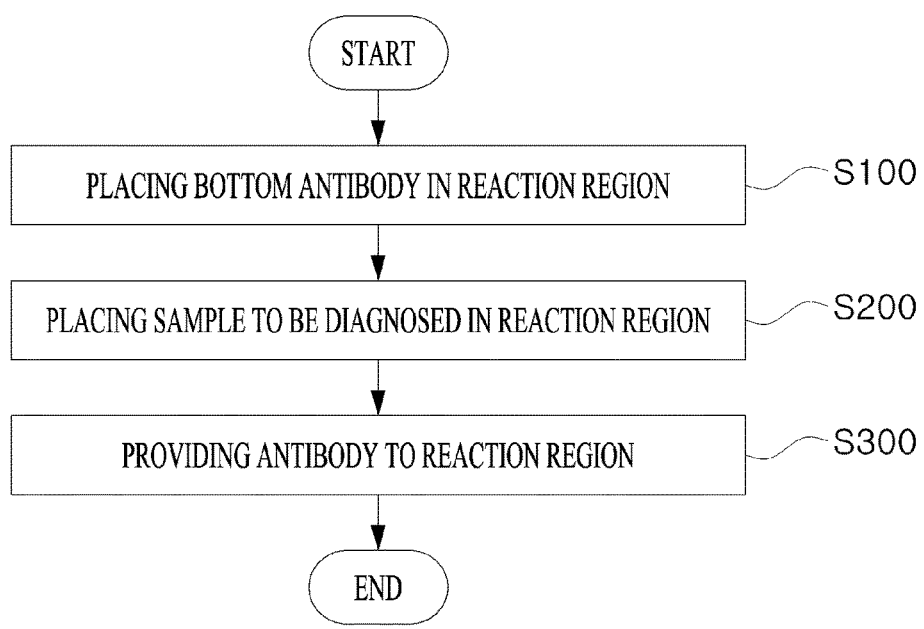
FIG. 41 illustrates a flowchart for describing an immunoassay method using sandwich Enzyme-Linked Immunosorbent Assay (ELISA) as an example of an immunoassay method according to the present application.

Prior to the placing of the sample to be diagnosed in the reaction region (S200), the immunoassay method may further include providing the plate PL on which bottom antibodies BAB, which are antibodies AB that react specifically with the target proteins TP, are fixated in the reaction region (S100), and the placing of the sample to be diagnosed in the reaction region may include placing a sample to be diagnosed in the reaction region in which the bottom antibodies BAB are fixated (see FIG. 41).

Figure 42:
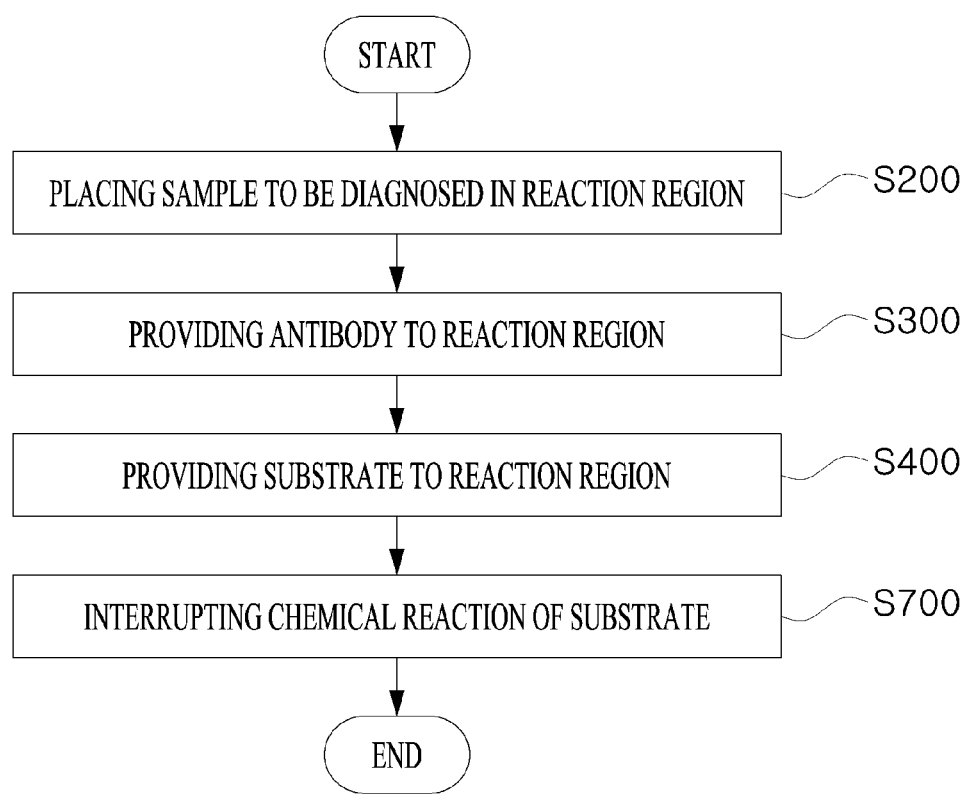
FIG. 42 illustrates a flowchart for describing an example of an immunoassay method according to the present application.

In addition to the placing of the sample (S200), the providing of the antibodies AB to the reaction region (S300), and the providing of the substrate SU to the reaction region (S400), the immunoassay method may further include interrupting a chemical reaction of the substrate SU (S700) (see FIG. 42).

A few embodiments on specific ways for performing immunoassay using the patch PA and the plate PL will be described below.

4.3.1 Reference Embodiment 1—Indirect ELISA

Figure 43:
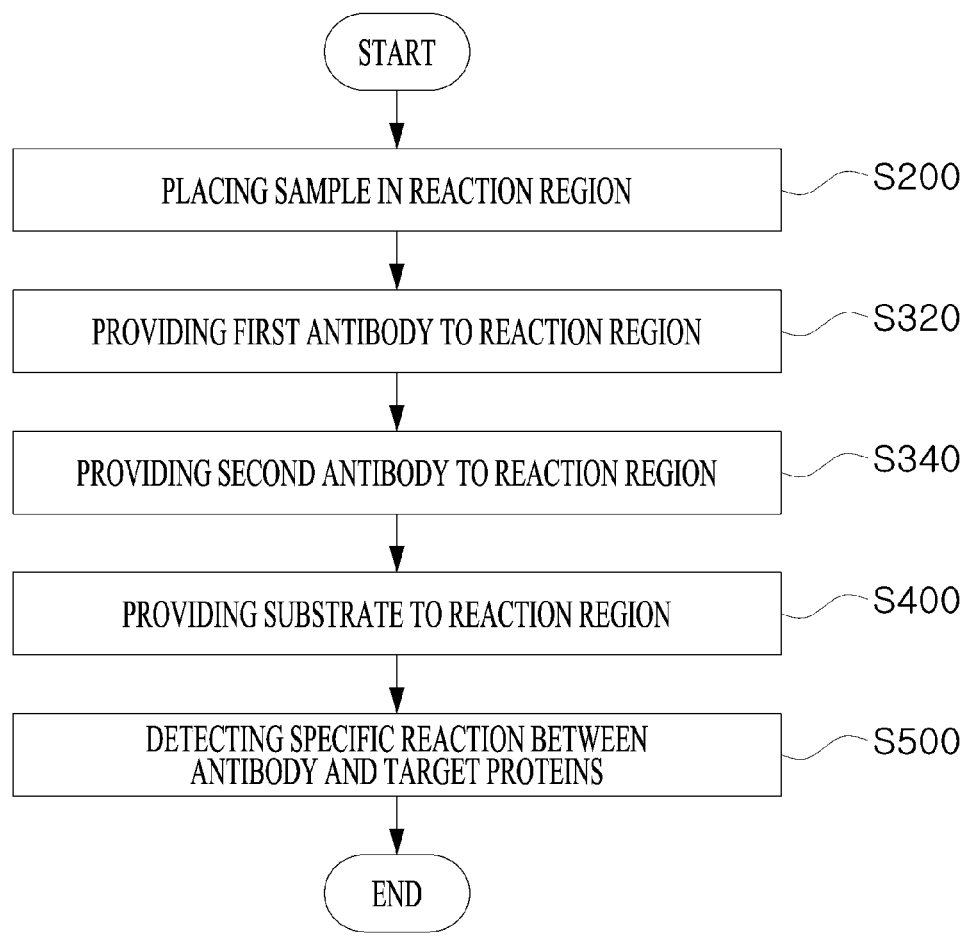
FIG. 43 illustrates a flowchart for describing an immunoassay method using indirect ELISA as an example of an immunoassay method according to the present application.

FIG. 43 illustrates a flowchart for describing an immunoassay method using indirect ELISA as an example of an immunoassay method according to the present application.

An immunoassay method using indirect ELISA according to an embodiment of the present application may include placing a sample SA in a reaction region (S200), providing first antibodies AB to the reaction region (S320), providing second antibodies AB to the reaction region (S340), providing a substrate SU to the reaction region (S400), and detecting a specific reaction between the antibodies AB and target proteins TP (S500).

Figure 44:
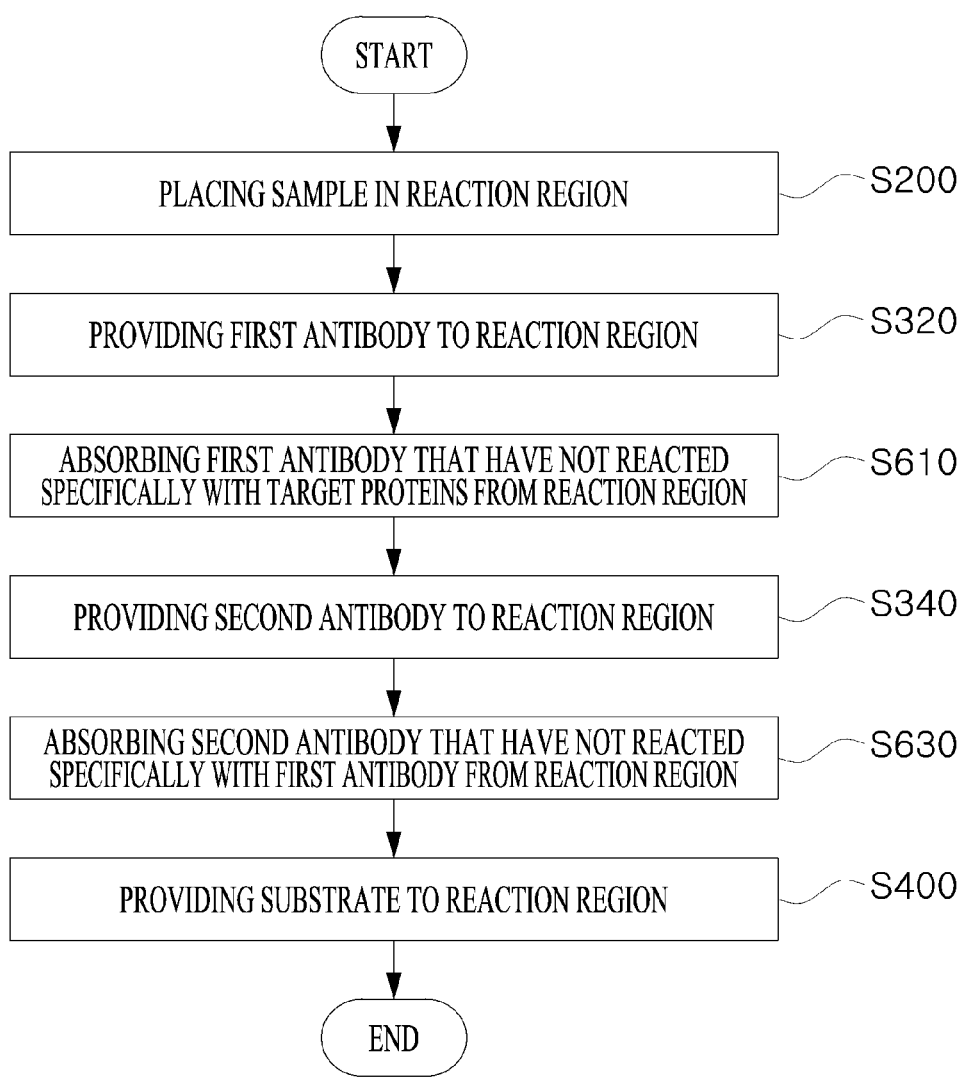
FIG. 44 illustrates a flowchart for describing an example of an immunoassay method according to the present application.

The immunoassay method using indirect ELISA according to an embodiment of the present application may include the placing of the sample SA in the reaction region (S200), the providing of the first antibodies AB to the reaction region (S320), absorbing first antibodies AB that have not reacted specifically with the target proteins TP from the reaction region (S610), the providing of the second antibodies AB to the reaction region (S340), absorbing second antibodies AB that have not reacted specifically with the first antibodies AB from the reaction region (S630), and providing of the substrate SU to the reaction region (S400). (see FIG. 44).

Immunoassay according to an embodiment of the present application may use a plate PL and a patch PA and be performed by indirect ELISA.

An immunoassay method according to an embodiment of the present disclosure may include fixating a sample SA to a plate PL, providing primary antibodies AB to the plate PL by using a first patch PA, and providing secondary antibodies AB to the plate PL by using a second patch PA.

The fixating of the sample SA on the plate PL may include fixating the sample SA to be diagnosed on the plate PL. The fixating of the sample SA on the plate PL may include drying a bodily fluid sample SA to be diagnosed on the plate PL and fixating the bodily fluid sample SA on the plate PL. The fixating of the sample SA to be diagnosed on the plate PL may include fixating the section of tissue.

The providing of the primary antibodies AB to the plate PL by using the patch PA may include contacting the first patch PA, which contains the primary antibodies AB, with the plate PL and providing the primary antibodies AB to the plate PL. The contacting of the first patch PA with the plate PL may include contacting the first patch PA with the sample SA fixated on the plate PL. The contacting of the first patch PA with the plate PL may include contacting the first patch PA with a region of the plate PL on which the sample SA is fixated. The primary antibodies AB may be changed in accordance with antigens desired to be detected. The primary antibodies AB may be antibodies AB that bind specifically with antigens desired to be detected.

The providing of the primary antibodies AB by using the first patch PA may include contacting the first patch PA with the plate PL and separating the first patch PA from the plate PL. The contacting of the first patch PA with the plate PL and then separating the first patch PA from the plate PL may allow the primary antibodies AB to be selectively transferred. In other words, when antigens to which the primary antibodies AB bind specifically are fixated on the plate PL, the primary antibodies AB may be selectively transferred from the first patch PA. Here, primary antibodies AB that have moved to the plate PL but have not bound specifically (hereinafter, "residual primary antibodies") may be absorbed into the first patch PA and removed from the plate PL as the first patch PA is separated from the plate PL.

The absorption of the residual primary antibodies AB into the patch PA may be performed by the residual primary antibodies AB being dissolved in a water film WF, which has been formed due to contact between the first patch PA and the plate PL, and the water film WF being moved along with the first patch PA when the first patch PA is separated from the plate PL. Throughout the present application, a water film which is generated due to contact between a patch and a sample or the like may refer to a thin liquid membrane in the vicinity of a contact region. In this case, the membrane being formed does not necessarily have a flat shape. However, the water film is not limited thereto, and in the present application, a water film may be understood as referring to a region in which movement of substance is possible due to contact between a patch and a sample or the like or a region in which a substance has mobility after a patch is connected to a sample or the like.

Since, as described above, the residual primary antibodies AB are removed from the plate PL just by separation of the first patch PA, a washing process that is essentially required in performing conventional ELISA may be omitted. In other words, through a means of binding primary antibodies AB using primary patch PA of the present application, a process of using a washing solution to remove primary antibodies AB that have not bound specifically from the plate PL may be omitted.

Figure 45:
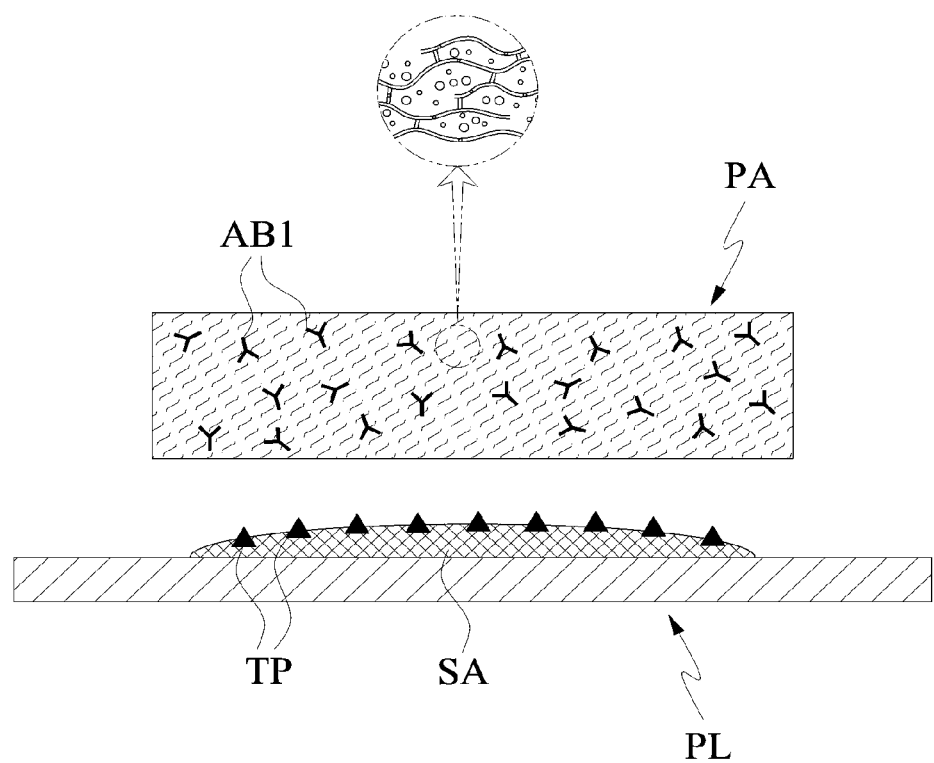
FIG. 45 illustrates a part of an immunoassay method using indirect ELISA as an embodiment of an immunoassay method according to the present application.
Figure 46:
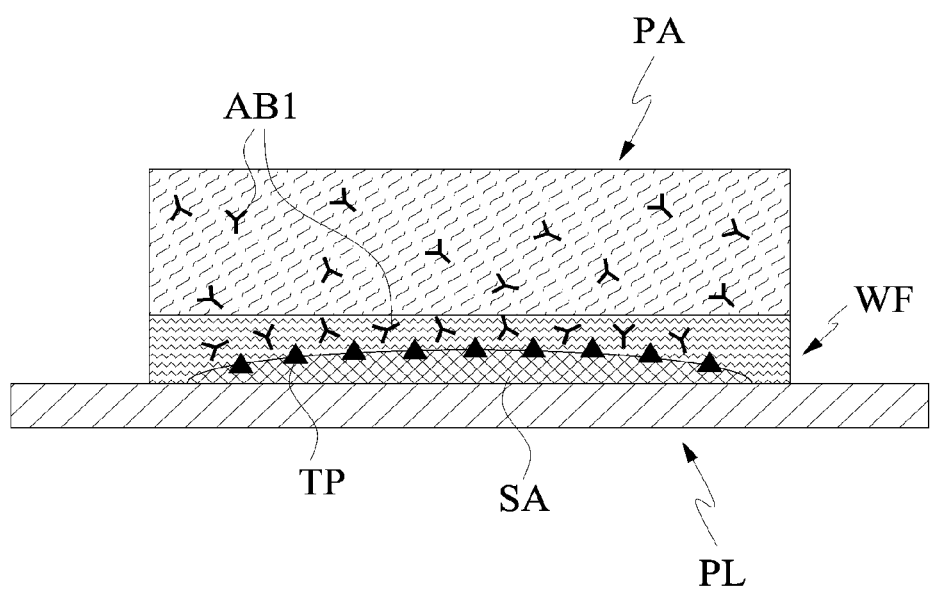
FIG. 46 illustrates a part of an immunoassay method using indirect ELISA as an embodiment of an immunoassay method according to the present application.
Figure 47:
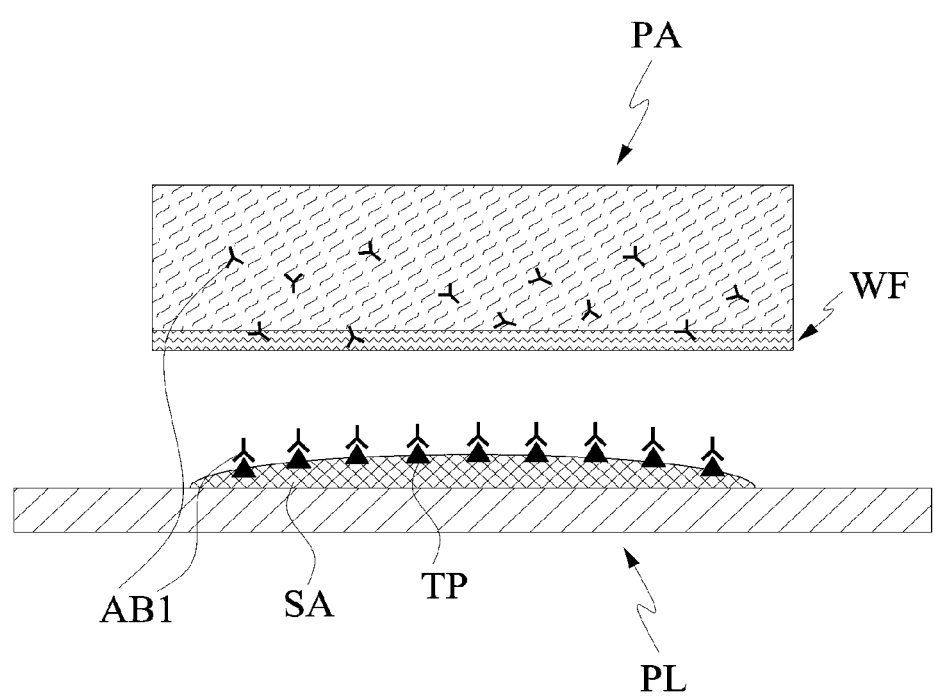
FIG. 47 illustrates a part of an immunoassay method using indirect ELISA as an embodiment of an immunoassay method according to the present application.

FIGS. 45 to 47 illustrate providing primary antibodies AB1 using a patch PA in performing an immunoassay by indirect ELISA. According to FIGS. 45 and 46, the patch PA may contain the primary antibodies AB1 and provide the primary antibodies AB1 to a sample SA located on the plate PL or a reaction region in which the sample SA is located. The providing of the primary antibodies AB1 to the plate PL by the patch PA may be performed by contacting the patch PA with the plate PL so that, through a water film WF formed in the vicinity of a contact region, the primary antibodies AB1 are allowed to move to the plate PL or the reaction region on the plate PL. The providing of the primary antibodies AB1 to the plate PL may be due to specific binding between the primary antibodies AB1 and the sample SA, and in particular, target proteins TP included in the sample SA.

Providing secondary antibodies AB to the plate PL using the patch PA may include contacting a second patch PA which contains the secondary antibodies AB with the plate PL and providing the secondary antibodies AB to the plate PL. The contacting of the second patch PA into contact with the plate PL may include contacting the second patch PA with the sample SA fixated on the plate PL. The contacting of the second patch PA with the plate PL may include contacting the second patch PA with a region of the plate PL on which the sample SA is fixated. The secondary antibodies AB may be antibodies AB that bind specifically with the primary antibodies AB. The secondary antibodies AB may be changed in accordance with the primary antibodies AB used. In this case, the secondary antibodies AB may be antibodies AB to which enzymes are attached. The enzymes attached to the antibodies may be horseradish peroxidase (HRP) or alkaline phosphatase (AP).

The providing of the secondary antibodies AB by using the second patch PA may include contacting the second patch PA with the plate PL and separating the second patch PA from the plate PL. The contacting of the second patch PA with the plate PL and then separating the second patch PA from the plate PL may allow the secondary antibodies AB to be selectively transferred to the plate PL. In other words, when antigens to which the primary antibodies AB bind specifically are fixated on the plate PL and the primary antibodies AB bound to the fixated antigens are present, the secondary antibodies AB that bind specifically with the primary antibodies AB may be selectively delivered to the plate PL. Here, secondary antibodies AB that have moved to the plate PL but have not bound specifically (hereinafter, "residual secondary antibodies") may be adsorbed into the second patch PA and removed from the plate PL as the second patch PA is separated from the plate PL. Accordingly, the process of using a washing solution to remove antibodies AB that have not bound specifically from the plate PL may be omitted. The absorption of the residual secondary antibodies AB into the second patch PA may be performed by the residual secondary antibodies AB being dissolved in a water film WF, which has been formed due to contact between the second patch PA and the plate PL, and the water film WF being moved along with the first patch PA when the second patch PA is separated from the plate PL.

Like the above-described removal of the residual primary antibodies AB using the primary patch PA, the residual secondary antibodies AB may be removed from the plate PL just by separation of the second patch PA. Accordingly, a process of using a washing solution to remove secondary antibodies AB that have not bound specifically from the plate PL, which is the process that is essentially required in performing conventional ELISA, may be omitted.

Figure 48:
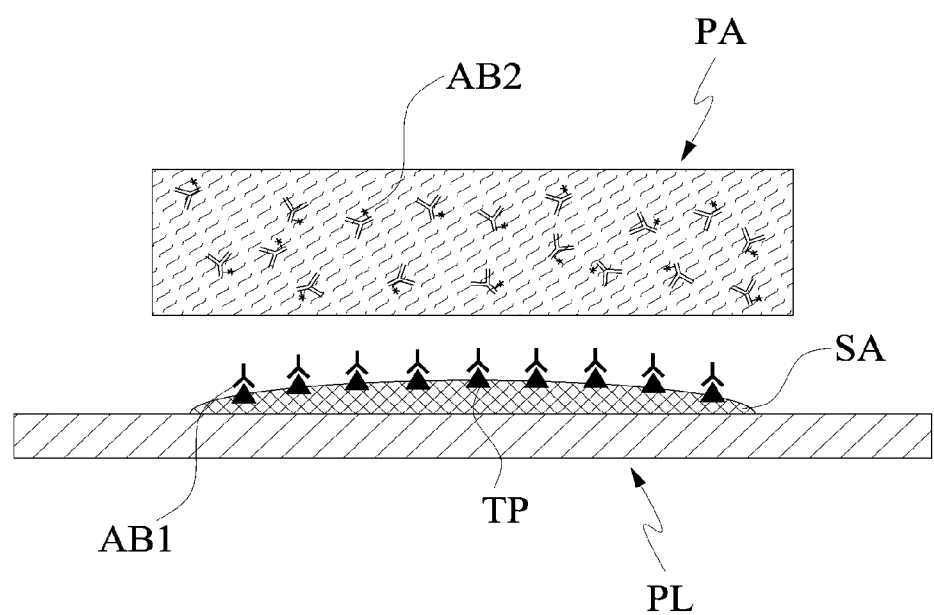
FIG. 48 illustrates a part of an immunoassay method using indirect ELISA as an embodiment of an immunoassay method according to the present application.
Figure 49:
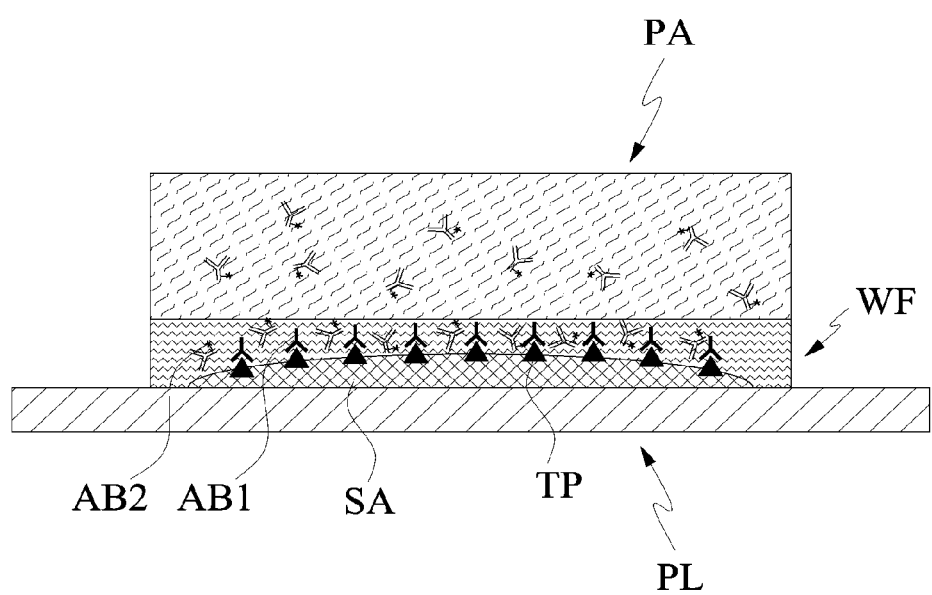
FIG. 49 illustrates a part of an immunoassay method using indirect ELISA as an embodiment of an immunoassay method according to the present application.
Figure 50:
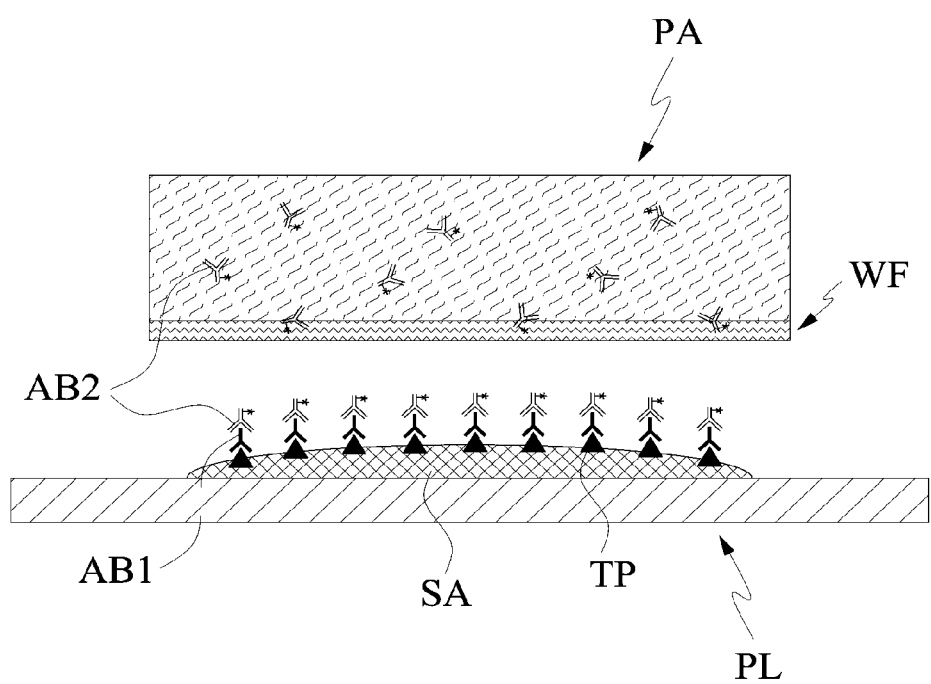
FIG. 50 illustrates a part of an immunoassay method using indirect ELISA as an embodiment of an immunoassay method according to the present application.

FIGS. 48 to 50 illustrate providing secondary antibodies AB2 using a patch PA in performing immunoassay by indirect ELISA. According to FIGS. 48 to 50, the patch PA may contain the secondary antibodies AB2 and provide the secondary antibodies AB2 to a sample SA located on the plate PL or a reaction region in which the sample SA is located. The providing of the secondary antibodies AB2 to the plate PL by the patch PA may be performed by contacting the patch PA contacting with the plate PL so that, through a water film WF formed in the vicinity of a contact region, the secondary antibodies AB2 are allowed to move to the plate PL or the reaction region on the plate PL. The providing of the secondary antibodies AB2 to the plate PL may be due to specific binding between the secondary antibodies AB2 and the sample SA, in particular, the primary antibodies AB1 bound to the target proteins TP included in the sample SA.

The immunoassay method according to the present embodiment may further include providing a substrate SU by using a patch PA. The providing of the substrate SU to the plate PL using the patch PA may include contacting a third patch PA which contains the substrate SU into contact with the plate PL and providing the substrate SU on the plate PL. The substrate SU may be ABTS or TMB. The substrate SU may be catalyzed by the enzymes and generate a product PD, and the product PD may serve as a label of specific binding that is desired to be detected.

Also, the above-described providing of the substrate SU using the third patch PA may include contacting the third patch PA with the plate PL and separating the third patch PA from the plate PL. The contacting of the third patch PA with the plate PL and then separating the third patch PA from the plate PL may allow control of duration for maintaining a contact between the third patch PA and the plate PL. In other words, the third patch PA may be separated from the plate PL at an optimal time point.

The immunoassay may be performed by detecting the product PD that is generated by a chemical reaction of the substrate SU which is catalyzed by the enzymes. In this case, when the reaction is not terminated at an optimal time point, an excessive amount of product PD may be produced, and it may be difficult to perform quantitative measurement of the product PD. In this case, according to an embodiment of the present application, since the reaction may be stopped at an optimal time point as a substrate SU patch PA is separated as described above, the above-described measurement error problem due to an excessive reaction may be solved. When, as described above, the substrate SU patch PA is removed at an optimal time point, the specific binding may be detected by measuring the product PD until the time point at which the substrate SU patch PA is removed.

Figure 51:
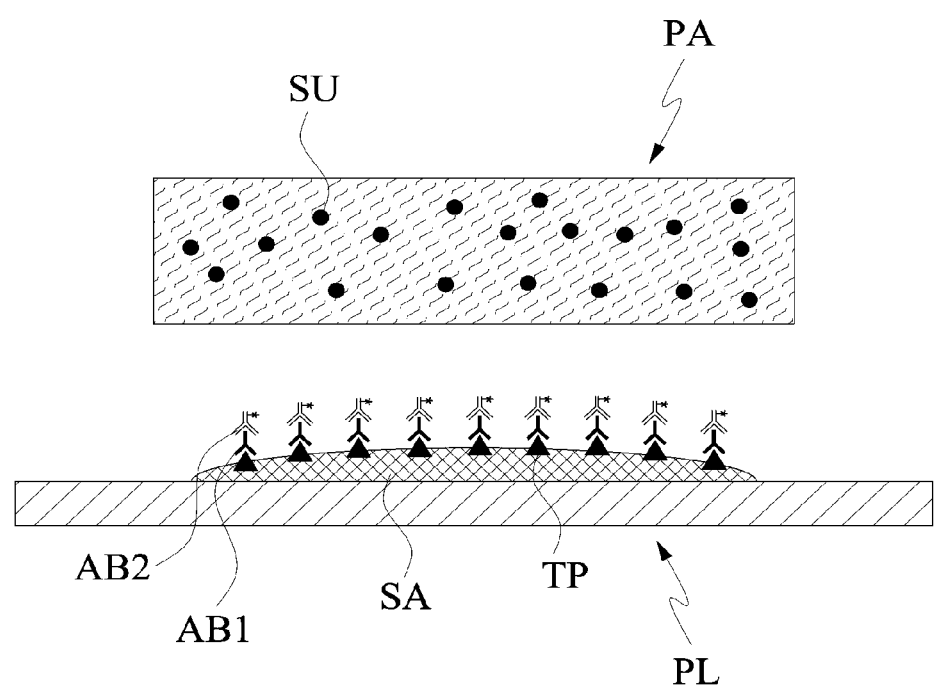
FIG. 51 illustrates a part of an immunoassay method using indirect ELISA as an embodiment of an immunoassay method according to the present application.
Figure 52:
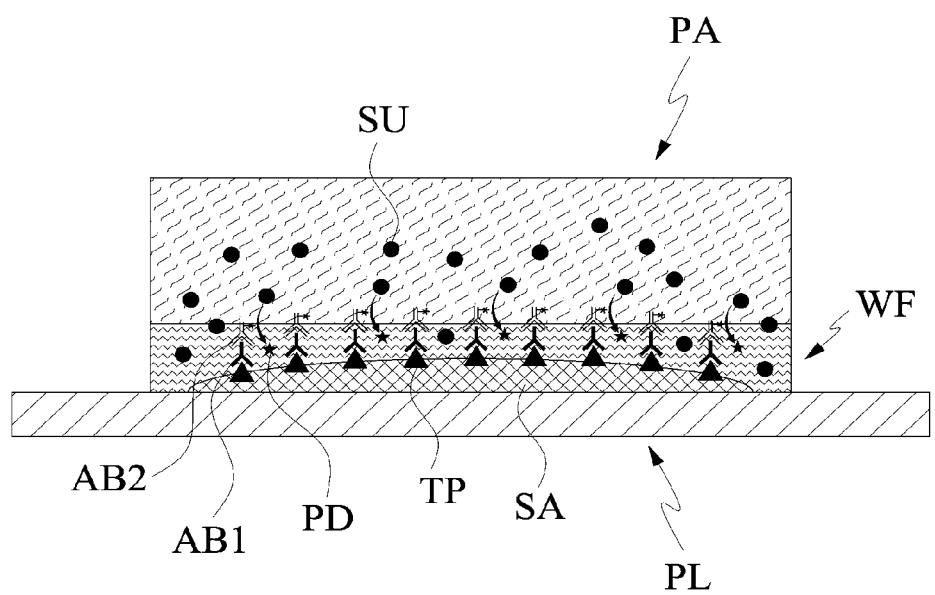
FIG. 52 illustrates a part of an immunoassay method using indirect ELISA as an embodiment of an immunoassay method according to the present application.
Figure 53:
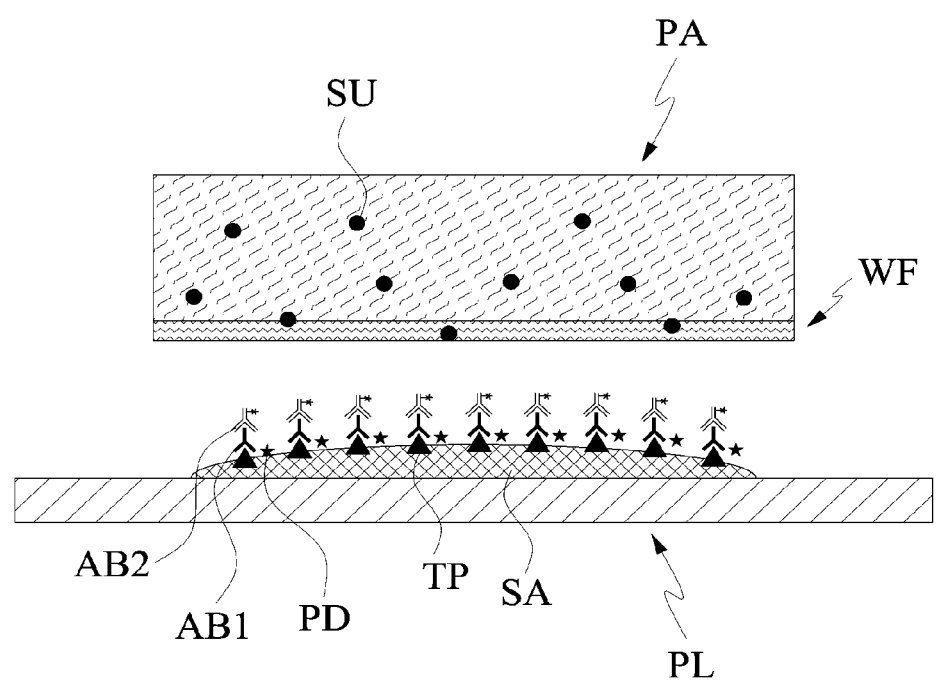
FIG. 53 illustrates a part of an immunoassay method using indirect ELISA as an embodiment of an immunoassay method according to the present application.

FIGS. 51 to 53 illustrate providing a substrate SU using a patch PA in performing immunoassay by indirect ELISA. According to FIGS. 51 to 53, the patch PA may contain the substrate SU and provide the substrate SU to a sample SA located on the plate PL or a reaction region in which the sample SA is located. The providing of the substrate SU to the plate PL by the patch PA may be performed by contacting the patch PA with the plate PL so that, through a water film WF formed in the vicinity of a contact region, the substrate SU is allowed to move to the plate PL or the reaction region on the plate PL. The substrate SU may produce a product PD or be converted into the product PD due to a chemical reaction catalyzed by enzymes attached to secondary antibodies AB located on the plate PL.

The immunoassay method according to the present embodiment may further include absorbing a residue using a washing patch PA. The absorbing of the residue using the washing patch PA may include contacting the washing patch PA with the plate PL to absorb the residue. The absorbing of the residue using the washing patch PA may include contacting the washing patch PA into contact with the plate PL to absorb first antibodies AB that have not bound specifically to at least a portion of the fixated sample SA. The absorbing of the residue using the washing patch PA may include contacting the washing patch PA into contact with the plate PL to absorb second antibodies AB that have not bound specifically to at least some of the first antibodies AB.

The absorbing of the residue using the washing patch PA may be performed after the providing of the primary antibodies AB to the plate PL by using the first patch PA and before the providing of the secondary antibodies AB to the plate PL by using the second patch PA. Alternatively, the absorbing of the residue using the washing patch PA may be performed after the providing of the secondary antibodies AB to the plate PL by using the second patch PA and before the providing of the substrate SU to the plate PL by using the patch PA.

The absorbing of the residue using the washing patch PA may substitute for performing washing using a washing solution in a conventional immunoassay method. Since a conventional washing method is mostly performed by pouring a washing solution onto a plate PL to rinse the plate PL so as to remove a substance, which is located on the plate PL without binding specifically, an excessive amount of solution is consumed in the conventional washing method. However, when the patch PA is used to absorb a residue from the plate PL as in the present application, the amount of washing solution consumed is significantly reduced in comparison to the conventional method, and thus economic feasibility is improved.

Figure 54:
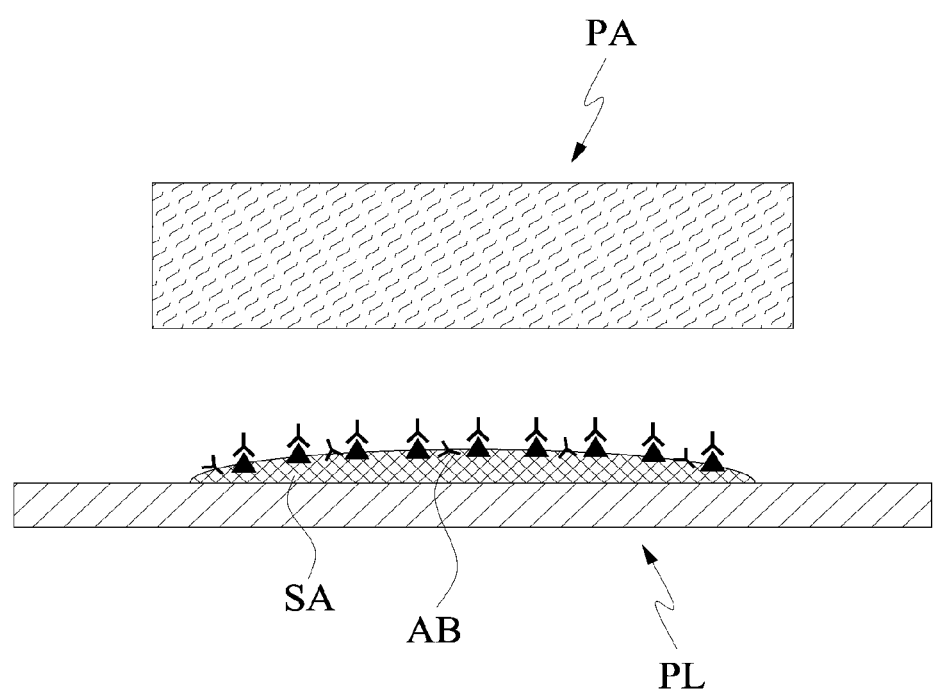
FIG. 54 illustrates performance of washing using a washing patch according to an embodiment of the present application.
Figure 55:
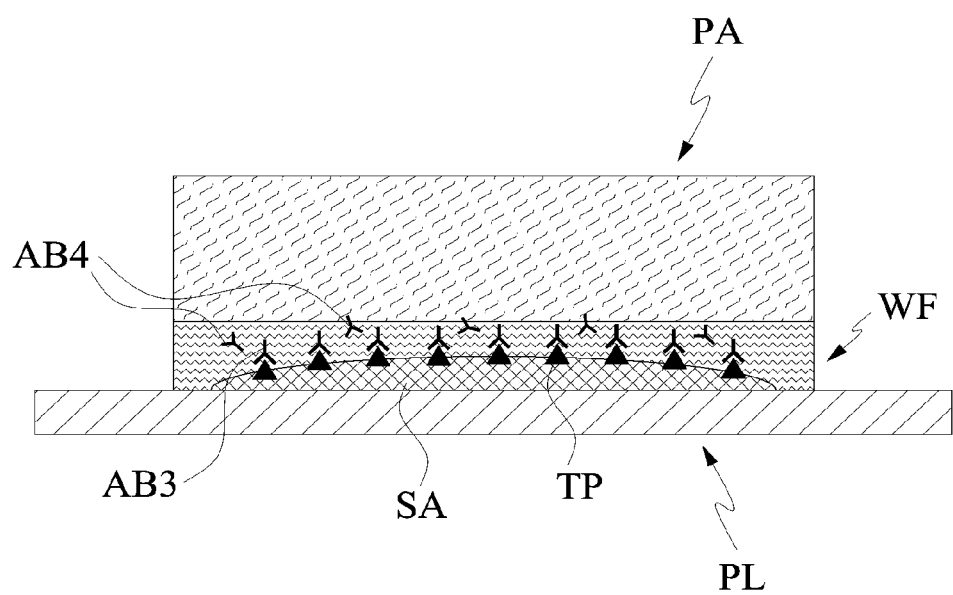
FIG. 55 illustrates performing washing using a washing patch according to an embodiment of the present application.
Figure 56:
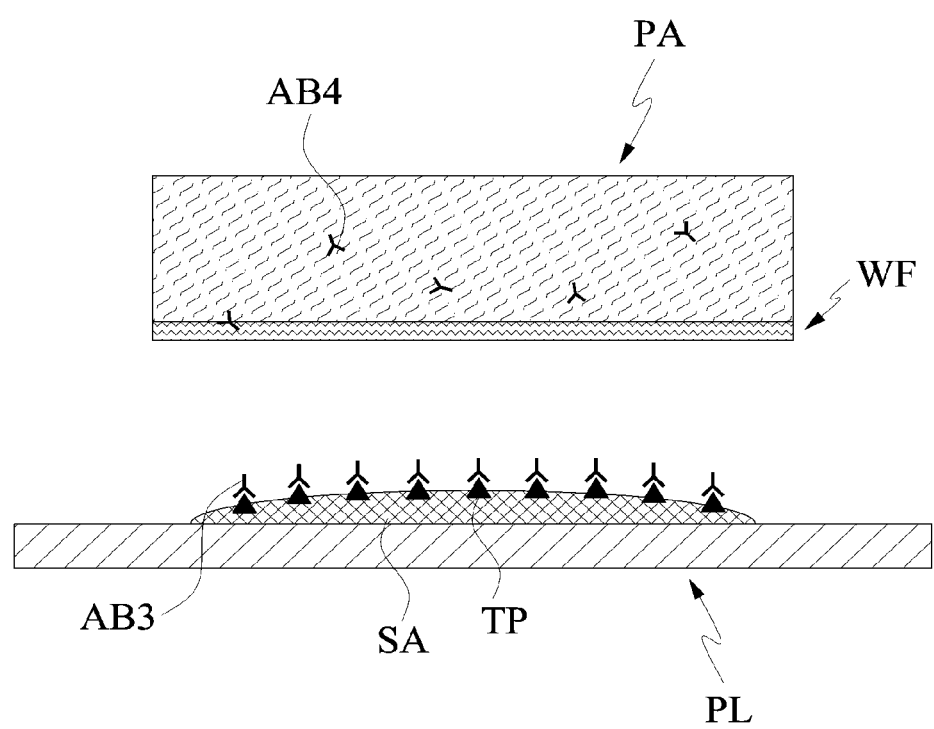
FIG. 56 illustrates performing washing using a washing patch according to an embodiment of the present application.

FIGS. 54 to 56 illustrate performing washing in an embodiment of immunoassay according to the present application. According to FIGS. 54 to 56, a patch PA may absorb residual substance from a plate PL. The residual substance may be antibodies AB4 that have not bound specifically to the target proteins TP. In this case, antibodies AB3 to which the target proteins TP have bound specifically may not be absorbed into the patch. The patch PA may be a washing patch PA that contains a washing solution.

The immunoassay method according to the present embodiment may include deterging substances that interfere with detection of the specific binding. Specifically, in performing the immunoassay method of the present application, a detergent patch PA for easily removing substances, which interfere with detection of the specific binding, from the plate PL may be used.

The immunoassay method according to the present embodiment may further include providing a predetermined environment to the plate PL. The providing of the predetermined environment may be performed using a buffer patch PA. The providing of the predetermined environment may include providing an environment by using a buffer patch PA that contains a buffer solution that facilitates each step of the immunoassay. For example, a buffer patch PA that contains a peroxide buffer may be used when detecting chemiluminescence.

The immunoassay method according to the present embodiment may include interrupting a reaction on the plate PL. The interrupting of the reaction may be performed using an interruption patch PA. The interrupting of the reaction may include interrupting a chemical reaction, that is, a reaction of producing a product PD, of the substrate SU catalyzed by the enzymes. The interrupting of the reaction may include terminating the reaction.

The immunoassay method according to the present embodiment may further include detecting a specific reaction, and this may include detecting a reaction of producing a product PD of the substrate SU. The detecting of the producing reaction may include detecting antigens to which the primary antibodies AB have bound specifically. The detecting of the antigens to which the primary antibodies AB have bound specifically may include detecting a product PD that is generated due to a reaction of the substrate SU catalyzed by enzymes attached to the secondary antibodies AB bound to the primary antibodies AB. In this case, the detecting of the product PD may be implemented by measuring color development due to the reaction, measuring luminescence due to the reaction, or measuring fluorescence due to the reaction.

The detecting of the producing reaction may be performed by contacting a patch PA that contains the substrate SU with the plate PL and detecting a chemical reaction of the substrate SU in real time. The detecting of the producing reaction may be performed by contacting patch PA that contains the substrate SU with the plate PL and detecting a result of reaction after a predetermined amount of time. In this case, the patch PA which contains the substrate SU may be separated and a result of reaction may be detected after a predetermined time point.

The detecting of the producing reaction may include contacting a patch PA that contains an interruption solution into contact with the plate PL and detecting a result of reaction while the patch PA which contains the interruption solution is in contact with the plate PL, or detecting a result of reaction after the patch PA which contains the interruption solution is separated from the plate PL.

In the present embodiment, the providing of the substrate SU or the providing of the primary antibodies AB or the secondary antibodies AB may not necessarily be performed using a patch PA. One of the providing of the substrate SU or the providing of the primary antibodies AB or the secondary antibodies AB may be substituted by providing the substrate SU, the primary antibodies AB or the secondary antibodies AB which are in a liquid or solution state to the plate PL.

Embodiments of a patch PA that may be used in an immunoassay according to the present embodiment will be described below. Each patch PA will be described as containing a few components, and each component may be understood as the above-described basic substance BS or additive substance AS. However, the components described below as being able to be contained in each patch PA may not be all components contained in each patch PA, and each patch PA may also contain other unspecified components.

4.3.1.1 Primary Antibody Patch

Immunoassay of the present application may be performed using a patch PA that contains primary antibodies. In other words, the patch PA may contain the primary antibodies and provide the primary antibodies AB to the plate PL.

The primary antibodies AB may be the additive substance AS contained in the patch PA. In other words, the patch PA may contain a solution including the primary antibodies AB. Also, in addition to the primary antibodies AB or a solution of the primary antibodies AB, the patch PA which contains the primary antibodies AB may also contain another basic substance SB or additive substance AS that allows the primary antibodies AB to easily bind to antigens to be detected.

The primary antibodies AB may be antibodies AB that bind specifically to target proteins TP. In other words, the primary antibodies AB may be antibodies AB that bind specifically to target antigens desired to be detected.

The patch PA which contains the primary antibodies AB may contain the primary antibodies AB, which bind specifically to the antigens desired to be detected, in a form of a solution. The primary antibodies AB may be evenly distributed throughout the patch PA. The primary antibodies AB may be absorbed into the patch PA from a separate medium and contained in the patch PA. The primary antibodies AB may be contained in the patch PA in a state in which the primary antibodies AB being attached to fine particles.

When, as in the present embodiment, the primary antibodies AB are contained in the patch PA and provided to the plate PL, primary antibodies AB that have not bound specifically to a portion of a substance fixated on the plate PL may be re-absorbed into the patch PA. Accordingly, a process of washing the primary antibodies AB may be omitted, the patch PA may be reusable in some cases, and prompt and efficient diagnosis may be implemented.

The patch PA according to an embodiment of the present application may be an antibody AB-containing patch PA that includes antibodies AB that react specifically with target proteins TP and a mesh structural body NS which is provided in a mesh structure forming micro-cavities in which the antibodies AB are contained, and is configured to contact with a reaction region in which the target proteins TP are located so as to provide some of the contained antibodies AB to the reaction region. In this case, the antibodies AB that react specifically with the target proteins TP may be primary antibodies AB which specifically bind to target antigens.

4.3.1.2 Secondary Antibody Patch

Immunoassay of the present application may be performed using a patch PA that contains secondary antibodies AB. In other words, the patch PA may contain the secondary antibodies and provide the secondary antibodies AB to the plate PL.

The secondary antibodies AB may be the additive substance AS contained in the patch PA. The patch PA may contain a solution including the secondary antibodies AB. Also, in addition to the secondary antibodies AB or a solution of the secondary antibodies AB, the patch PA which contains the secondary antibodies AB may also contain a separate basic substance SB or additive substance AS that allows the secondary antibodies AB to easily bind to target primary antibodies AB. The secondary antibodies AB may be antibodies AB that bind specifically to primary antibodies AB. In this case, the specific binding between the primary antibodies AB and the secondary antibodies AB may be species-specific binding instead of epitope-specific binding. When secondary antibodies AB which species-specifically bind to primary antibodies AB are used, even when primary antibodies AB that aim to detect different proteins are used, the secondary antibodies AB having identification labels attached thereto may be commonly used as long as the primary antibodies AB originate from the same species.

Enzymes may be attached to the secondary antibodies AB. The enzymes attached to the secondary antibodies AB may serve as identifiers for detecting the specific binding. Specifically, the enzymes may be attached to the antibodies AB and serve as labels or reporters that detect antigens that bind specifically to the antibodies AB or antigens that bind specifically to antibodies AB binding specifically to the antibodies AB (in the case of indirect technique). The enzymes may be used by being bound so that the antibodies AB bind to fragment-crystallizable (FC) regions of molecules.

Generally, AP or HRP are mainly used as the enzymes.

Even when the patch PA that contains the secondary antibodies AB is used as described above, since secondary antibodies AB that have not bound specifically to a portion of substance fixated on the plate PL may be re-absorbed into the patch PA, prompt and efficient immunoassay may be performed.

The patch PA according to an embodiment of the present application may be an antibody-containing patch PA that includes antibodies AB that react specifically with target proteins TP and a mesh structural body NS which is provided in a mesh structure forming micro-cavities in which the antibodies AB are contained, and is configured to contact with a reaction region in which the target proteins TP are located so as to provide some of the contained antibodies AB to the reaction region. In this case, the antibodies AB that react specifically with the target proteins TP may be secondary antibodies AB which specifically bind to target antigens.

4.3.1.3 Substrate Patch

Immunoassay of the present application may be performed using a patch PA that contains a substrate SU. In other words, the patch PA may contain the substrate SU and provide the substrate SU to the plate PL.

The substrate SU may be the additive substance AS contained in the patch PA. The patch PA may contain a solution including the substrate SU. Also, the patch PA which contains the substrate SU may also contain the basic substance BS or additive substance AS that assists a reaction of producing a product PD of the substrate SU.

Specifically, the enzymes attached to the secondary antibodies AB may catalyze a chemical reaction of the substrate SU. The above-described specific binding may be detected from a product PD generated due to the reaction catalyzed by the enzymes. In other words, the substrate SU may be catalyzed by the enzymes and generate a product PD, and the product PD may be detected to detect the specific binding.

The substrate SU may be ABTS, TMB, or the like. The substrate SU used may be changed in accordance with enzymes being used and detection means. For example, when enzymes being used are AP, color development may be detected by using para-Nitrophenylphosphate (pNPP) as the substrate SU. As another example, when enzymes being used are HRP, color development may be detected by using TMB or the like as the substrate SU.

When the substrate SU is provided to the plate PL by using the above-described substrate SU patch PA, the amount of substrate SU solution consumed is significantly reduced in comparison to the conventional ELISA method in which a substrate SU solution is poured into a reaction solution of a plate PL to detect a reaction. Therefore, diagnosis may be performed economically. Also, since the substrate SU patch PA may be separated at an appropriate time point to prevent an excessive reaction, a more precise detection result may be acquired.

4.3.1.4 Washing Patch

An immunoassay method according to the present embodiment may be performed using a washing patch PA that absorbs a residue. In other words, in the immunoassay method according to the present embodiment, the residue may be absorbed by contacting the washing patch PA with the plate PL and then separating the washing patch PA from the plate PL. The residue may refer to a residue that has not been absorbed into each patch PA and not removed, when the above-described primary antibody AB patch PA, secondary antibody AB patch PA, or substrate SU patch PA is brought into contact with the plate PL and then separated therefrom.

The washing patch PA may contain a washing solution. The washing solution may include a TBS or PBS with Tween 20 added to a portion thereof. The washing solution may be provided as a solution in which the residue may be dissolved in accordance with a residue to be absorbed. The patch PA containing the washing solution may further contain the basic substance BS or additive substance AS that assists in the washing.

By the patch PA containing the washing solution and being brought into contact with the plate PL and then separated therefrom, impurities or residue on the plate PL, for example, unbound antibodies AB or the like, may be absorbed into the patch PA and removed. The residue may include first antibodies AB that have not bound specifically to the antigens to be detected included in the sample SA or second antibodies AB that have not bound specifically to the first antibodies AB.

In the absorption of the residue into the washing patch PA, the washing patch PA may come into contact with the plate PL, that is, the plate PL region on which the sample SA is located, so that the water film WF may be formed, and the residue may be dissolved in the water film WF. The residue dissolved in the water film WF may be absorbed into the washing patch PA by the water film WF being moved along with the washing patch PA when the washing patch PA is separated from the plate PL.

When a residue on the plate PL is removed by using the above-described washing patch PA, the amount of washing solution consumed is significantly reduced in comparison to the conventional ELISA method. Therefore, diagnosis may be performed economically. Also, since the substrate SU patch PA may be separated at an appropriate time point to prevent an excessive reaction, a more precise detection result may be acquired.

4.3.1.5 Detergent Patch

An immunoassay method according to the present embodiment may be performed using a detergent patch PA that performs deterging. In other words, the detergent patch PA may contain a detergent solution and provide the detergent solution to the patch PA.

Specifically, in performing an immunoassay method of the present application, the detergent patch PA for simply removing substances that interfere with detection of the specific binding from the plate PL may be used. Specifically, the detergent patch PA may contain a detergent substance that allows substances interfering with detection of the specific binding, such as first antibodies AB that have not bound specifically to antigens to be detected included in the sample SA or second antibodies AB that have not bound specifically to the first antibodies AB, to be easily removed, and may be used in removing the substances.

In this case, the detergent patch PA may contain at least some of detergent substances for easily removing the interfering substances. The detergent substance may be at least one of Tween 20, Triton X-100, and CHAPS.

4.3.1.6 Buffer Patch

An immunoassay method according to the present embodiment may be performed using a buffer patch PA. In other words, the buffer patch PA may contain a buffer solution and provide a predetermined environment to the plate PL. The buffer patch PA may contain a buffer solution that facilitates each step of the immunoassay. As an example of the buffer solution, a peroxide buffer solution may be used when detecting chemiluminescence.

4.3.1.7 Interruption Patch

An immunoassay method according to the present embodiment may be performed using a reaction interruption patch PA. In other words, the reaction interruption patch PA may contain an interruption solution, which interrupts a reaction of the substrate SU catalyzed by the enzymes, and provide the interruption solution to the plate PL.

The patch PA may contain an interruption solution for interrupting a reaction of the substrate SU. That is, the reaction interruption patch PA may be manufactured, and the reaction interruption patch PA may be used to provide the interruption solution to the plate PL and interrupt the reaction of the substrate SU at an appropriate time point.

The interruption solution may contain at least a portion of an interruption substance for interrupting a reaction of the substrate SU. The interruption substance may be a sulfuric acid.

In performing the immunoassay method according to the present embodiment, any one chosen from using the interruption patch PA and separating the above-described substrate SU patch PA from the plate PL may be performed. For example, to interrupt a reaction of the substrate SU, any one chosen from contacting the stop patch PA into contact with the plate PL, contacting the stop patch PA into contact with the substrate SU patch PA which is in contact with the plate PL (for example, contacting the stop patch PA into contact with an upper surface of the substrate SU patch in contact with the plate PL) and separating the substrate SU patch from the plate PL may be performed.

4.3.1.8 AB Pair Patch

Figure 63:
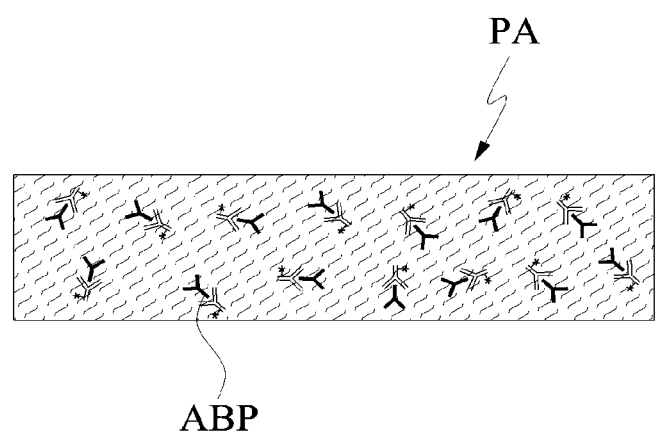
FIG. 63 illustrates a patch that contains a pair of antibodies as an embodiment of a patch according to the present application.

FIG. 63 illustrates a patch PA that contains a pair of antibodies AB as an embodiment of a patch PA according to the present application. According to FIG. 63, the patch PA may contain pairs of antibodies AB each formed by binding between a primary antibody AB and a secondary antibody AB or antibody AB complexes.

Figure 64:
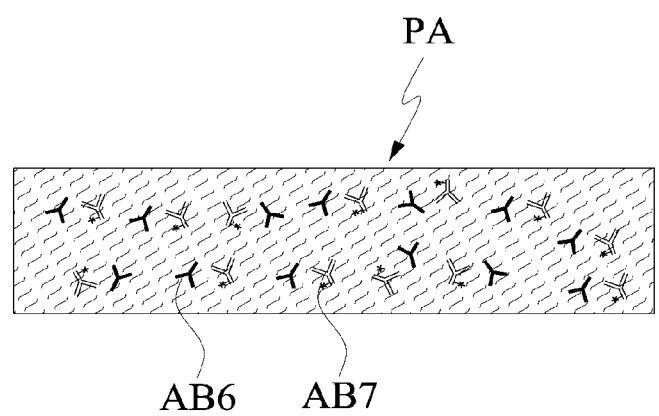
FIG. 64 illustrates a patch that contains a primary antibody and a secondary antibody as an embodiment of a patch according to the present application.

In the immunoassay method according to the present embodiment, primary antibodies AB6 and secondary antibodies AB7 may be provided to the plate PL together. In other words, the patch PA may simultaneously contain and provide the primary antibodies AB6 and the secondary antibodies AB7 (see FIG. 64). Due to the primary antibodies AB6 and the secondary antibodies AB7 being contained in a single patch PA and being provided to the plate PL together, a procedure for performing diagnosis may become more prompt and convenient.

The patch PA that contains the primary antibodies AB and the secondary antibodies AB may be manufactured to include the primary antibodies AB and the secondary antibodies AB. Alternatively, the patch PA that contains the primary antibodies AB and the secondary antibodies AB may be manufactured by contacting a patch PA that contains the primary antibodies AB with a patch PA that contains the secondary antibodies AB.

In this case, in the immunoassay method according to the present embodiment, providing primary antibodies AB to the plate PL by using a first patch PA and providing secondary antibodies AB to the plate PL by using a second patch may be substituted by providing the primary antibodies AB and the secondary antibodies AB to the plate by using the first patch PA.

In other words, the immunoassay method according to an embodiment of the present application may be implemented by including fixating a sample SA on a plate PL and providing the primary antibodies AB and the secondary antibodies AB to the plate PL by using a patch PA. In this case, the secondary antibodies AB may bind specifically to the primary antibodies AB. The secondary antibodies AB and the primary antibodies AB may be contained in the patch PA and provided to the plate PL in a state of being bound to each other.

According to the above embodiment, a substance absorbed by the above-described washing patch PA may be a complex of the primary antibodies AB and the secondary antibodies AB that have not bound to the proteins or antigens to be detected. Also, according to the above embodiment, a substance of which removal is facilitated by the detergent patch PA may be a complex of the primary antibodies AB and the secondary antibodies AB that have not bound to the proteins or antigens to be detected. Also, according to the above embodiment, a substance removed from the plate PL when the patch PA is separated from the plate PL may be a complex of the primary antibodies AB and the secondary antibodies AB that have not bound to the proteins or antigens to be detected.

Figure 65:
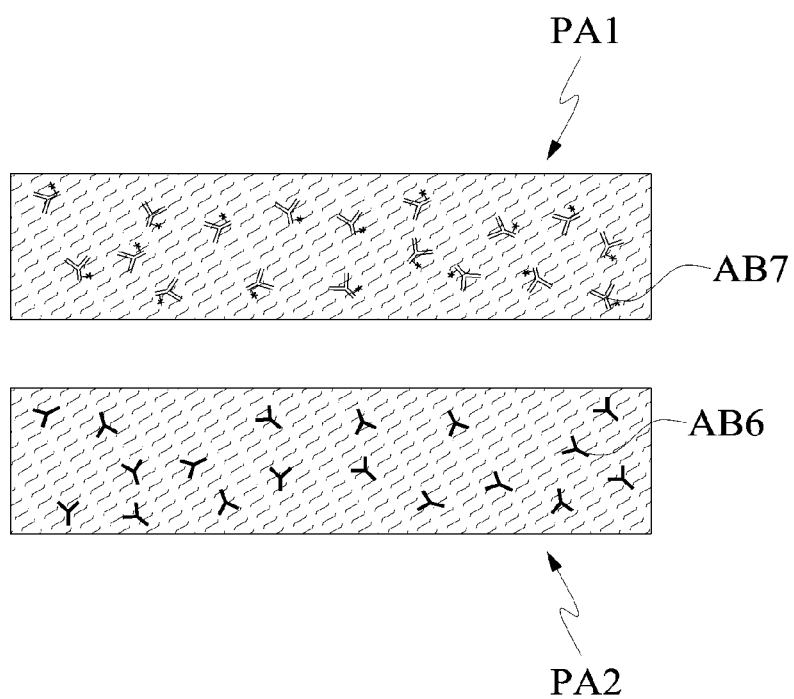
FIG. 65 illustrates a part of an example of a process of manufacturing a patch that contains a pair of antibodies as an embodiment of a patch according to the present application.
Figure 66:
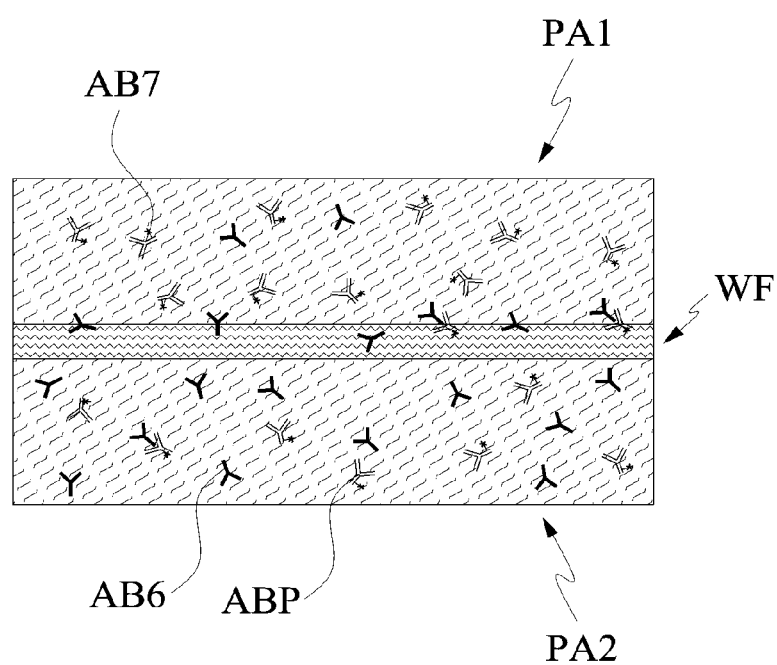
FIG. 66 illustrates a part of an example of a process of manufacturing a patch that contains a pair of antibodies as an embodiment of a patch according to the present application.

FIGS. 65 and 66 illustrate an example of manufacturing a patch PA that contains a pair of antibodies as an embodiment of a patch PA according to the present application. According to FIGS. 65 and 66, a patch PA that contains pairs of antibodies AB may be acquired by contacting a patch PA that contains primary antibodies AB6 and a patch PA that contains secondary antibodies AB7 and then separating the two. The acquisition of the patch PA that contains the pairs of antibodies AB may be performed by contacting the patch PA that contains the primary antibodies AB6 and the patch PA that contains the secondary antibodies AB7 so that the contained substances may be exchanged, causing diffusion to occur so that the primary antibodies AB6 and the secondary antibodies AB7 are located in each patch PA, and making the primary antibodies AB6 and the secondary antibodies AB7 bind to each other.

The patch PA according to an embodiment of the present application may be an antibody AB-containing patch PA that includes antibodies AB that react specifically with target proteins TP and a mesh structural body NS which contains the antibodies AB and comes into contact with a reaction region in which the target proteins TP are located so as to provide some of the contained antibodies AB to the reaction region. In this case, the target proteins TP may be antigens, the antibodies AB may be pairs of antibodies AB formed by binding between primary antibodies AB which specifically bind to the antigens and secondary antibodies AB which specifically bind to the primary antibodies AB, and the pairs of antibodies AB may react specifically with the antigens.

4.3.1.9 Absorbing and Containing Patch

A patch PA according to the present application may contain antibodies AB, a substrate SU, a washing solution, and other substances required for immunoassay such as a basic substance BS and an additive substance AS, as described above. The above-described substances, in particular, the additive substance AS, may be contained in the patch PA from the step of manufacturing the patch PA or may be kept in a different medium and then absorbed into the patch PA and contained therein when diagnosis is performed. In other words, the patch PA may absorb substances such as antibodies AB and a substrate SU from a separate medium and contain the substances therein.

In this case, a different medium may be a plate PL or paper. Being kept in the different medium may refer to being applied on a surface of a plate PL, being applied on a surface of the plate PL and dried, being absorbed into paper, or being absorbed into the paper and dried.

This may be particularly usefully applied to a patch PA that contains antibodies AB. When the antibodies AB are kept in a different medium as described above, the ability to contain antibodies AB is significantly improved, and quality of a predetermined level or higher may be guaranteed for antibodies AB used when performing diagnosis.

Figure 74:
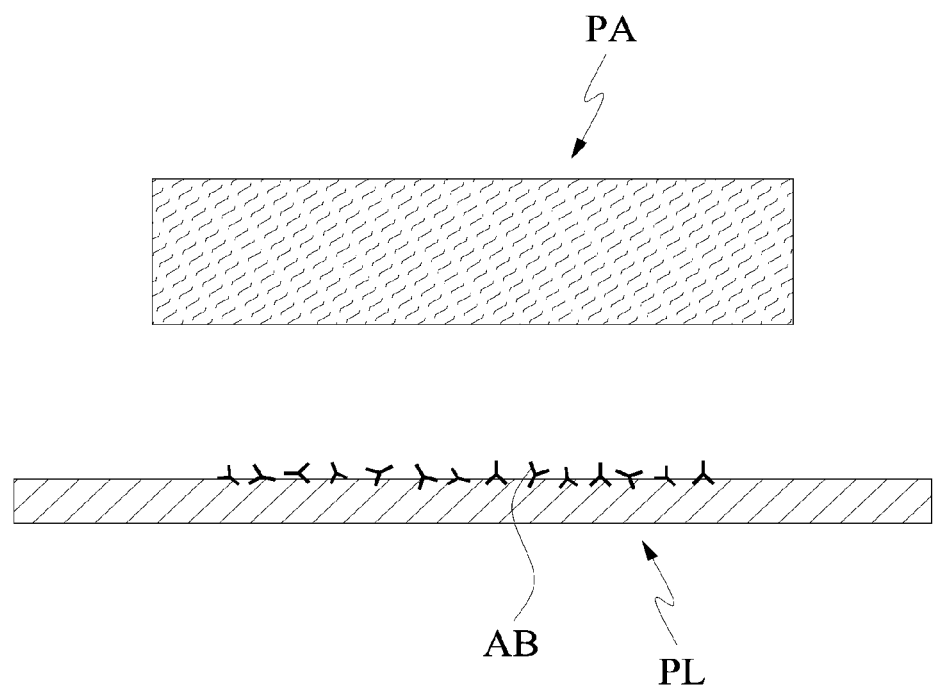
FIG. 74 illustrates a patch that absorbs and contains an antibody as an example of a patch in an immunoassay method according to the present application.
Figure 75:
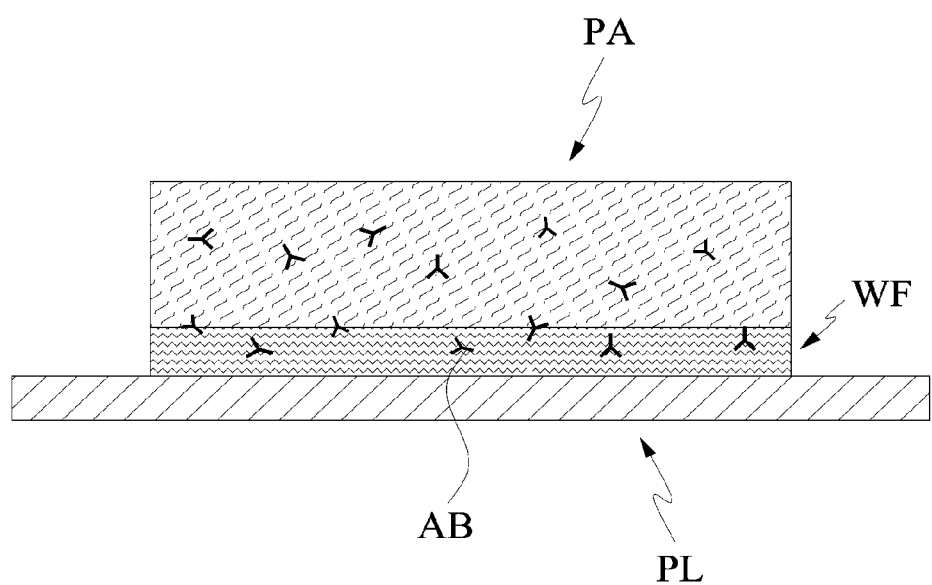
FIG. 75 illustrates a patch that absorbs and contains an antibody as an example of a patch according to the present application.
Figure 76:
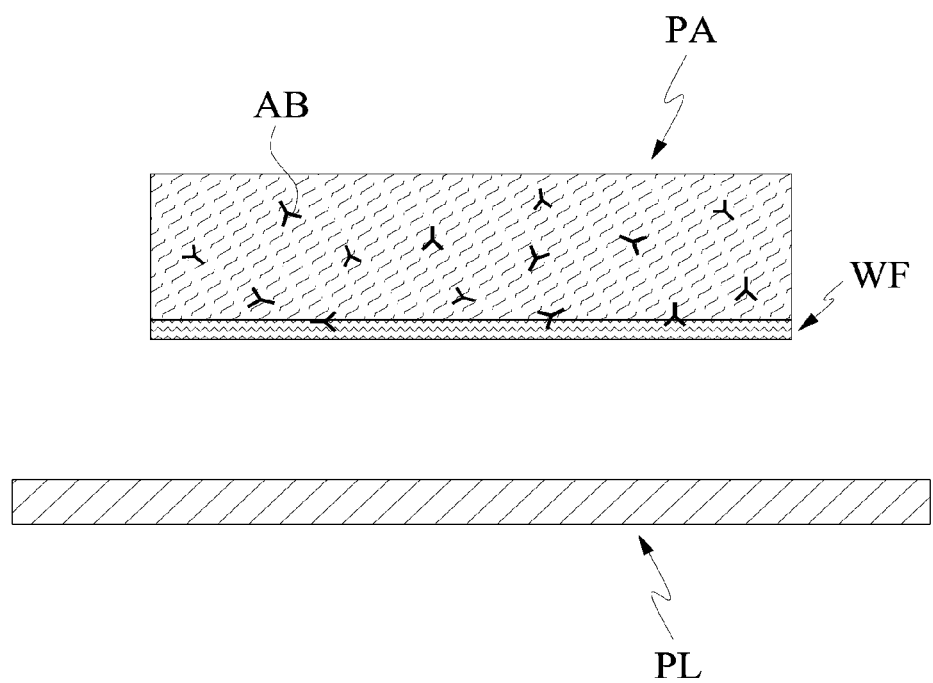
FIG. 76 illustrates a patch that absorbs and contains an antibody as an example of a patch according to the present application.

FIGS. 74 to 76 illustrate an example of a patch PA that absorbs a substance from a medium and contains the substance therein as an embodiment of a patch PA according to the present application. According to FIGS. 74 to 76, the patch PA according to the present application may absorb antibodies AB applied on a plate PL and contain the antibodies AB therein. The absorption of the antibodies AB applied on the plate PL may be performed by the antibodies AB being captured in a water film WF, which is formed due to contact between the patch PA and the plate PL, and the patch PA being separated from the plate PL such that the water film WF is moved along with the patch PA.

Figure 77:
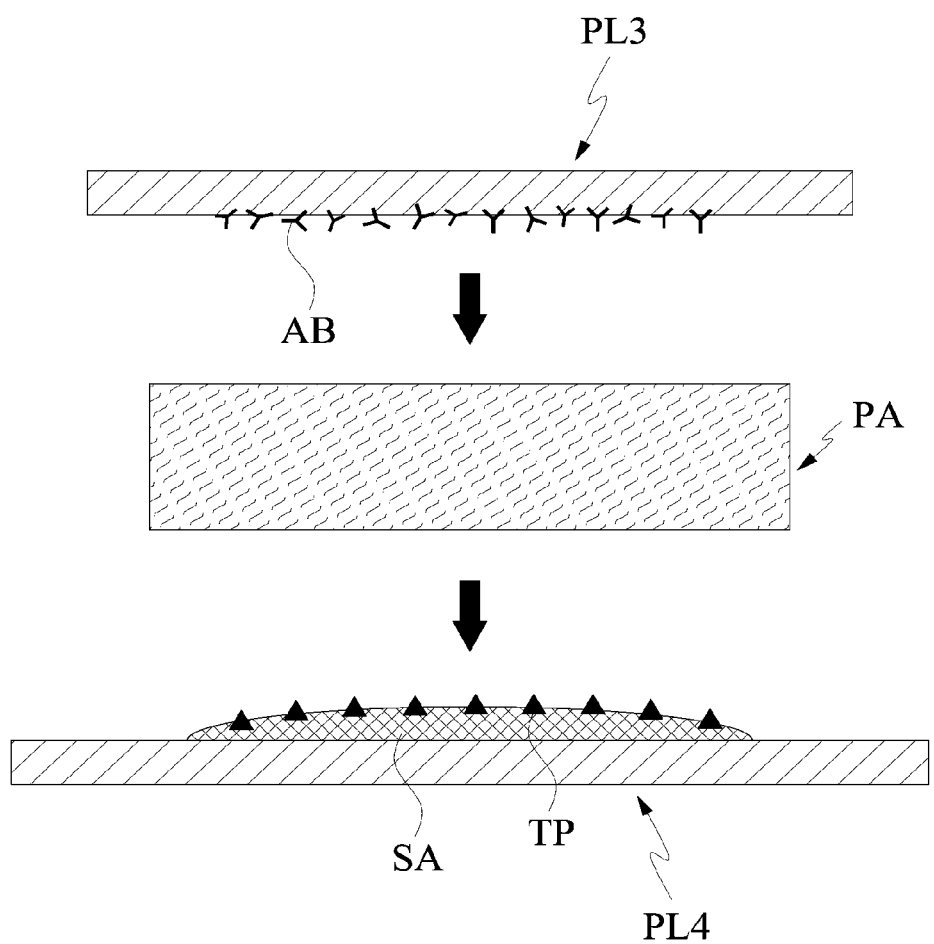
FIG. 77 illustrates a patch that absorbs, contains, and provides an antibody as an example of a patch according to the present application.

As an embodiment of a patch PA according to the present application, FIG. 77 illustrates a case in which a patch PA, which absorbs antibodies AB from a separate medium and contains the antibodies AB therein, provides the antibodies AB to the plate PL. According to FIG. 77, a patch PA according to the present application may absorb antibodies AB from a plate PL3 on which the antibodies AB are applied and provide the absorbed antibodies AB to a plate PL4 on which a sample SA is applied. This may be performed by bringing a lower surface of the patch PA into contact with the plate PL4, on which the sample SA is applied, in a state in which the plate PL3, on which the antibodies AB are applied, is brought into contact with an upper surface of the patch PA.

4.3.1.10 Transfer Patch

A patch PA according to the present application may provide a substance (that is, a substance to be transferred) contained in a medium (that is, medium) to a plate or another external region. For example, the patch PA may provide substances such as antibodies AB and a substrate SU kept in a medium to a separately-provided plate.

The patch may contain a liquid substance which may dissolve a substance to be transferred, which is contained in the medium. For example, when a substance to be transferred is water-soluble, the patch may contain water or an aqueous solution. In this case, the patch may provide the water or aqueous solution to the medium. As the aqueous solution or the like is provided, substances contained in the medium may be provided to the plate. It may be understood that, by such a mechanism, a moist environment is provided by the patch to the medium and the plate.

In the present embodiment, a surface of the patch PA may be brought into contact with an external medium in which the substances are contained. A surface of the medium opposite the surface coming into contact with the patch may be brought into contact with a plate or another external region. In this case, the patch may transfer a substance contained in the medium to the plate.

In the present embodiment, the medium may be a substance having an ability to absorb or an ability to transmit. The medium may be paper. The medium may be a substance-containing medium in a mesh form.

As an embodiment of the present application, an immunoassay method using the transfer patch may be provided. Specifically, there may be provided an immunoassay method for performing diagnosis by detecting a target protein from a sample to be diagnosed by using a patch which includes a mesh structural body forming micro-cavities and is configured to contain a liquid substance in the micro-cavities, the immunoassay method including contacting a medium, which contains antibodies that reacts specifically with the target protein, into contact with the patch, and contacting the patch into contact with a reaction region in which the target protein is placed, wherein, when the medium is brought into contact with the patch, at least a portion of the antibodies contained in the medium is absorbed into the patch. In this case, when the patch is brought into contact with the reaction region, at least a portion of the antibodies absorbed into the patch may be movable to the reaction region.

In the above embodiment, the bringing of the medium into contact with the patch may include contacting a surface of the medium with the patch, and the contacting of the patch with the reaction region may include contacting a surface of the patch, which is not in contact with the medium, into contact with the reaction region.

According to an embodiment of the present application, an antibody providing kit using the transfer patch may be provided. Specifically, there may be provided an antibody providing kit that includes a medium which contains antibodies that reacts specifically with a target protein, and antibodies delivery patch which includes a mesh structural body forming micro-cavities and is configured to come into contact with the medium to absorb a portion of the antibodies contained in the medium and come into contact with a reaction region in which the target protein is placed to provide at least a portion of the absorbed antibodies to the reaction region.

4.3.2 Reference Embodiment 2—Direct ELISA

Figure 57:
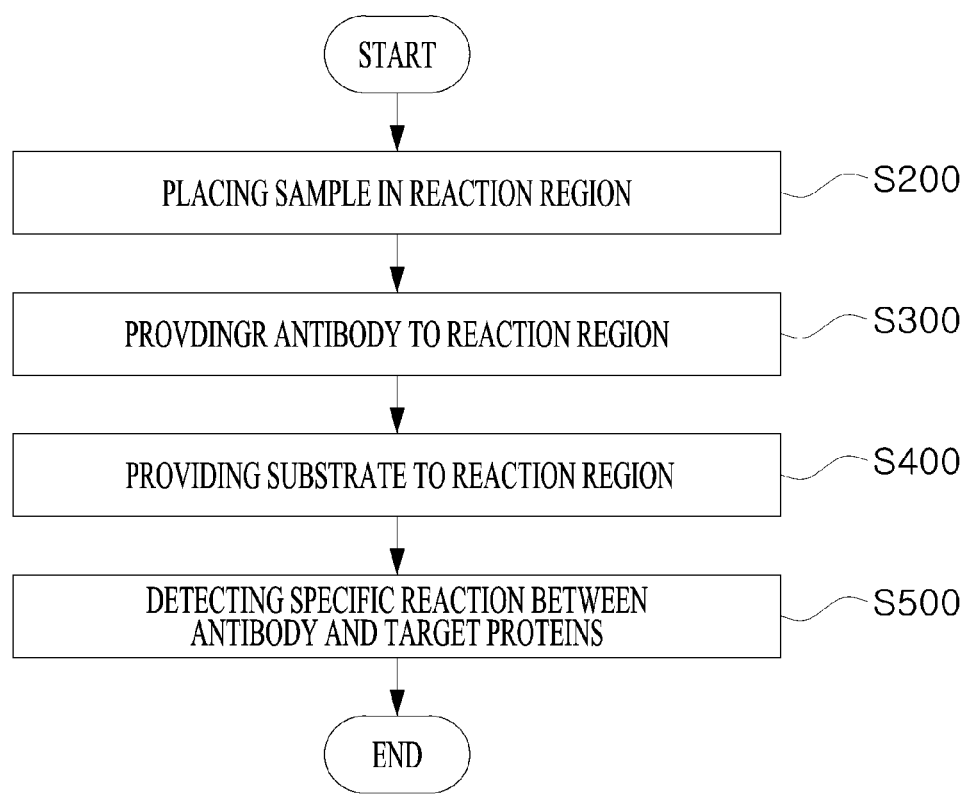
FIG. 57 illustrates a flowchart for describing an immunoassay method using direct ELISA as an example of an immunoassay method according to the present application.

FIG. 57 illustrates a flowchart for describing an immunoassay method using direct ELISA as an example of an immunoassay method according to the present application.

An immunoassay method using direct ELISA according to an embodiment of the present application may include placing a sample SA in a reaction region (S200), providing antibodies AB to the reaction region (S300), providing a substrate SU to the reaction region (S400), and detecting a specific reaction between the antibodies AB and target proteins TP (S500).

The immunoassay according to the present embodiment may use a plate PL and a patch PA and be performed by direct ELISA.

The immunoassay method according to the present embodiment may include fixating a sample SA on the plate PL and providing antibodies AB to the plate PL by using the patch PA.

The fixating of the sample SA on the plate PL may include drying the sample SA to be diagnosed on the plate PL and fixating the sample SA on the plate PL. The fixating of the sample SA to be diagnosed on the plate PL may include fixating a bodily fluid sample SA or a section of tissue to be diagnosed on the plate PL.

The providing of the antibodies AB to the plate PL by using the patch PA may include contacting the patch PA which contains the antibodies AB with the plate PL to provide the antibodies AB to the plate PL. The contacting of the patch PA into contact with the plate PL and details related to antigens and antibodies AB have been described above in relation to indirect ELISA. Since the present embodiment is performed by direct ELISA, enzymes may be attached to the antibodies AB. The enzymes attached to the antibodies AB may be a HRP or AP.

The providing of the antibodies AB by using the patch PA may include providing the patch PA into contact with the plate PL and separating the patch PA from the plate PL. The providing of the patch PA into contact with the plate PL and then separating the patch PA from the plate PL may allow the antibodies AB to be selectively provided. In other words, when antigens to which the antibodies bind specifically are fixated on the plate PL, the antibodies AB may be selectively provided from the patch PA to the plate PL. Here, antibodies AB that have moved to the plate PL but have not bound specifically (hereinafter, "residual antibodies") may be absorbed into the patch PA and removed from the plate PL as the patch PA is separated from the plate PL. The absorption of the residual antibodies AB into the patch PA may be performed by the residual antibodies AB being dissolved in a water film WF, which is formed by contact between the patch PA and the plate PL, and the water film WF being moved along with the patch PA when the patch PA is separated from the plate PL.

Since, as described above, the residual antibodies AB may be removed from the plate PL just by separation of the patch PA, a washing process for residual substance (e.g., the residual antibodies AB) which is essentially required in performing conventional ELISA may be omitted. In a conventionally-performed washing process for residual substance, a large amount of washing solution has to be poured onto a plate PL to rinse the plate PL to remove residual substance, which has not participated in specific binding, from the plate PL. However, since the patch PA of the present application may capture and separate the residual substance just by being brought into contact with the plate PL and then separated therefrom, the washing process is unnecessary. Consequently, reagents may be more efficiently used, and ELISA may be simply performed.

Figure 58:
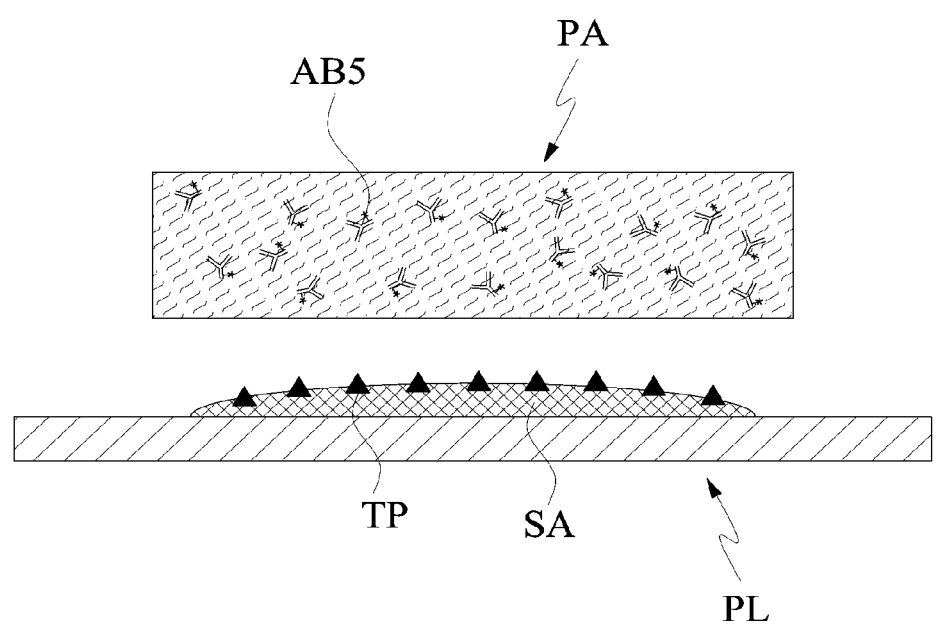
FIG. 58 illustrates a part of an immunoassay method using direct ELISA as an embodiment of an immunoassay method according to the present application.
Figure 59:
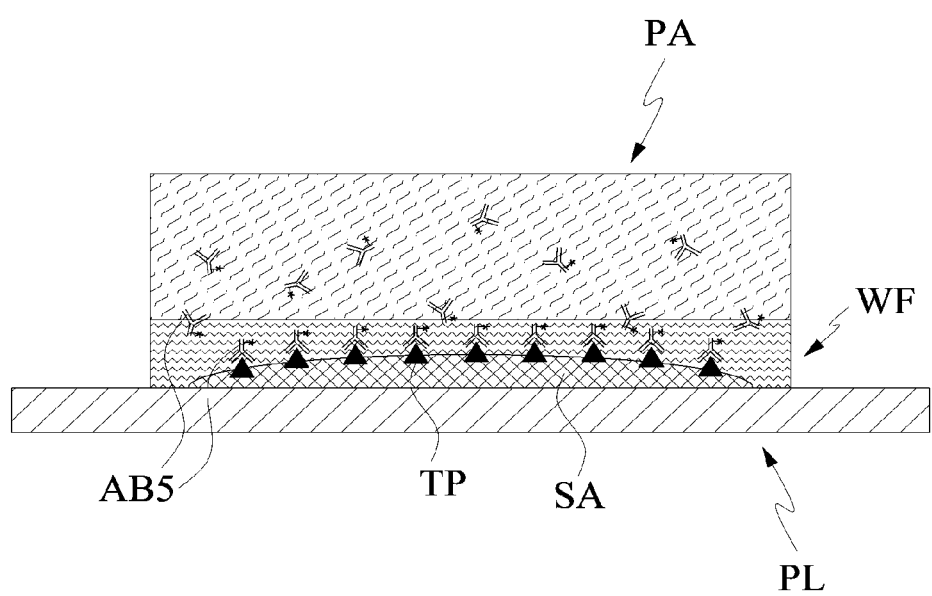
FIG. 59 illustrates a part of an immunoassay method using direct ELISA as an embodiment of an immunoassay method according to the present application.
Figure 60:
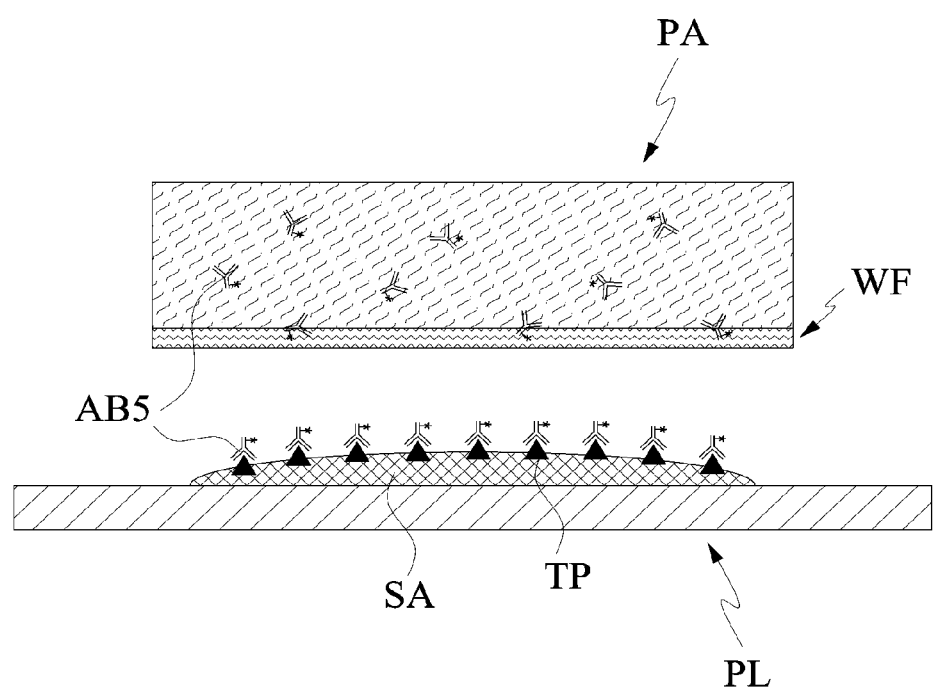
FIG. 60 illustrates a part of an immunoassay method using direct ELISA as an embodiment of an immunoassay method according to the present application.

FIGS. 58 to 60 illustrate a part of an immunoassay method using direct ELISA in an embodiment of immunoassay according to the present application. According to FIGS. 58 to 60, a patch PA may provide antibodies AB5 to a reaction region. Identification labels such as enzymes may have been attached to the antibodies AB5. The providing of the antibodies AB5 to the plate PL by the patch PA may be performed by the patch PA coming into contact with the plate PL so that the antibodies AB5 are movable to the plate PL or the reaction region on the plate PL through a water film WF formed in the vicinity of a contact region. The providing of the antibodies AB5 to the plate PL may be due to specific binding between the antibodies AB5 and the sample SA, in particular, target proteins TP included in the sample SA.

The immunoassay method according to the present embodiment may further include providing a substrate SU to the plate PL by using the patch PA. The providing of the substrate SU by using the patch PA may include contacting the patch PA which contains the substrate SU with the plate PL to provide the substrate SU to the plate PL. The substrate SU may be ABTS or TMB. The substrate SU may be catalyzed by the enzymes and generate a product PD, and the product PD may serve as a label of specific binding that is desired to be detected.

Also, the providing of the substrate SU to the plate PL by using the patch PA which contains the substrate SU may include contacting the patch PA which contains the substrate SU into contact with the plate PL and separating the patch PA which contains the substrate SU from the plate PL. The contacting of the patch PA which contains the substrate SU into contact with the plate PL and then separating the patch PA which contains the substrate SU from the plate PL may allow control of duration for maintain a contact between the patch PA which contains the substrate SU and the plate PL are in contact. In other words, the patch PA which contains the substrate SU may be separated from the plate PL at an optimal time point.

The immunoassay method according to the present embodiment may further include absorbing a residue using a washing patch PA. The absorbing of the residue using the washing patch PA may include contacting the washing patch PA into contact with the plate PL to absorb the residue. The absorbing of the residue using the washing patch PA may include contacting the washing patch PA into contact with the plate PL to absorb antibodies AB that have not bound specifically to at least a portion of the fixated sample SA. In other words, in detecting target specific binding, the washing patch PA may absorb residual substance that has not participated in the specific binding.

Figure 61:
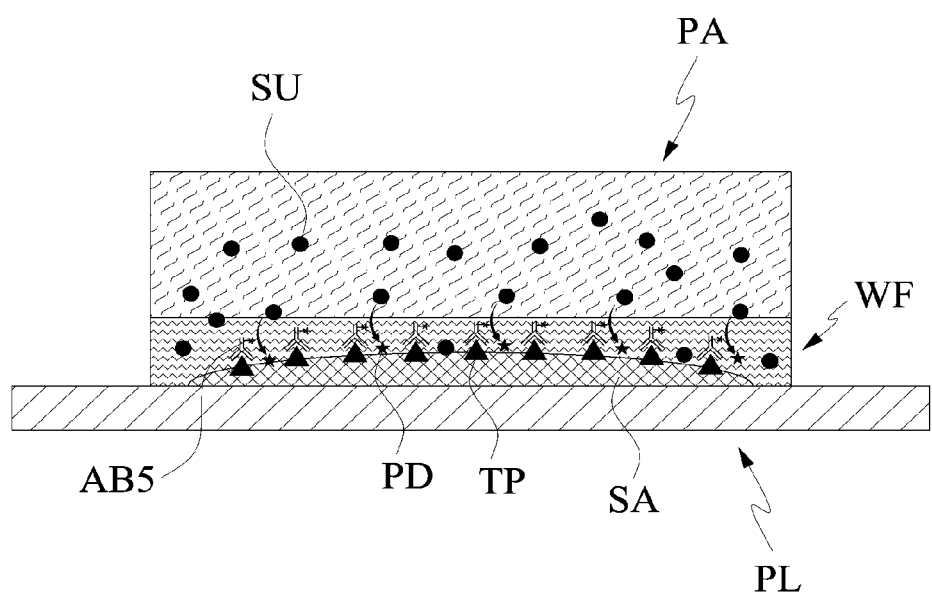
FIG. 61 illustrates a part of an immunoassay method using direct ELISA as an embodiment of an immunoassay method according to the present application.
Figure 62:
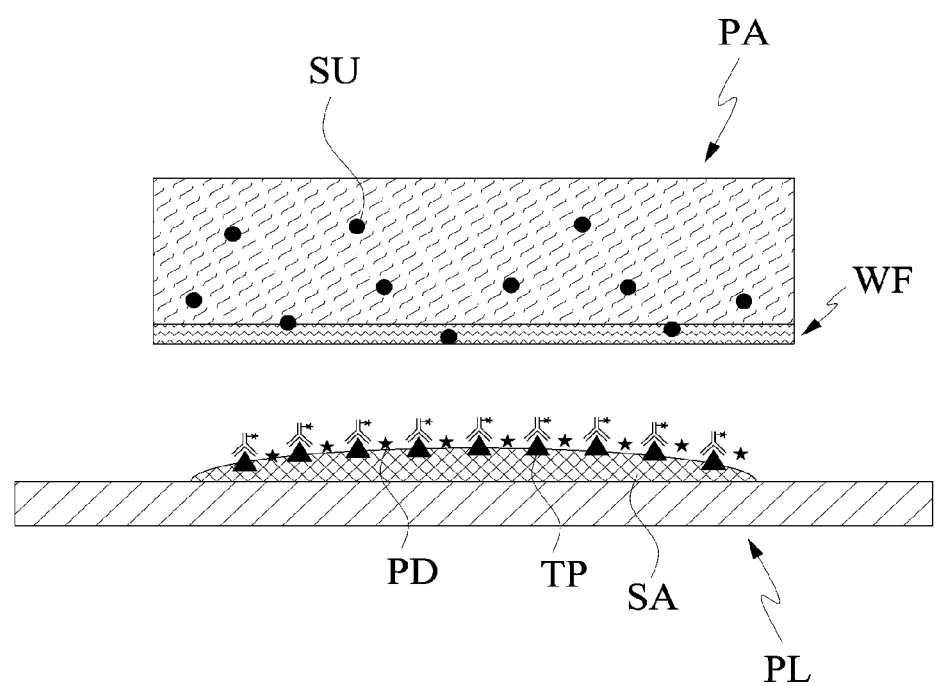
FIG. 62 illustrates a part of an immunoassay method using direct ELISA as an embodiment of an immunoassay method according to the present application.

FIGS. 61 and 62 illustrate providing a substrate SU using a patch PA in performing immunoassay by direct ELISA. According to FIGS. 61 and 62, the patch PA may contain the substrate SU and provide the substrate SU to a sample SA located on the plate PL or a reaction region in which the sample SA is located. The providing of the substrate SU to the plate PL by the patch PA may be performed by the patch PA coming into contact with the plate PL so that, through a water film WF formed in the vicinity of a contact region, the substrate SU is allowed to move to the plate PL or the reaction region on the plate PL. The substrate SU may produce a product PD or be converted into the product PD due to a chemical reaction catalyzed by enzymes attached to antibodies AB located on the plate PL.

The immunoassay method according to the present embodiment may further include absorbing a residue using a washing patch PA. The absorbing of the residue using the washing patch PA may include contacting the washing patch PA into contact with the plate PL to absorb the residue. The absorbing of the residue using the washing patch PA may include contacting the absorbing patch PA into contact with the plate PL to absorb antibodies AB that have not bound specifically to at least a portion of the fixated sample SA. In other words, in detecting target specific binding, the washing patch PA may absorb residual substance that has not participated in the specific binding.

The absorbing of the residue using the washing patch PA may be performed after the providing of the antibodies AB to the plate PL by using the patch PA and before the providing of the substrate SU to the plate PL by using the patch PA.

The absorbing of the residue using the washing patch PA may substitute for performing washing using a washing solution in a conventional immunoassay process. The conventional washing process is performed by a person directly using a large amount of washing solution to remove residual substance, and thus has problems in that a solution is wasted, manpower is required, and specific binding that has been formed may also be affected. However, when washing is performed using the patch PA as in the present application, since washing is not performed by flowing solution, there are advantages in that specific binding that has been formed is less affected, and consumption of a washing solution is significantly reduced.

The immunoassay method according to the present embodiment may include deterging substances that interfere with detection of the specific binding.

The immunoassay method according to the present embodiment may further include providing a predetermined environment to the plate PL.

The immunoassay method according to the present embodiment may include interrupting a reaction on the plate PL.

Details of the deterging, the providing of the environment, and the interrupting of the reaction may be similar to those described above with reference to indirect ELISA.

The immunoassay method according to the present embodiment may further include detecting antigens that have bound specifically to the provided antibodies AB. The detecting of the antigens that have bound specifically to the antibodies AB may include detecting a product PD generated due to a reaction between the substrate SU and enzymes bound to the antibodies AB. In this case, the detecting of the product PD may be implemented by measuring color development due to the reaction, measuring luminescence due to the reaction, or measuring fluorescence due to the reaction.

In addition, unless particularly mentioned otherwise, the above-described patches PA, methods of performing diagnosis, and the like used in indirect ELISA may also be applied similarly to performing immunoassay by direct ELISA.

In the present embodiment, the providing of the substrate SU or the providing of the primary antibodies AB or the secondary antibodies AB may not necessarily be performed using a patch PA. One of the providing of the substrate SU or the providing of the primary antibodies AB or the secondary antibodies AB may be substituted with providing the substrate SU, the primary antibodies AB or the secondary antibodies AB which are in a liquid or solution state to the plate PL.

4.3.3 Reference Embodiment 3—Sandwich ELISA

Figure 67:
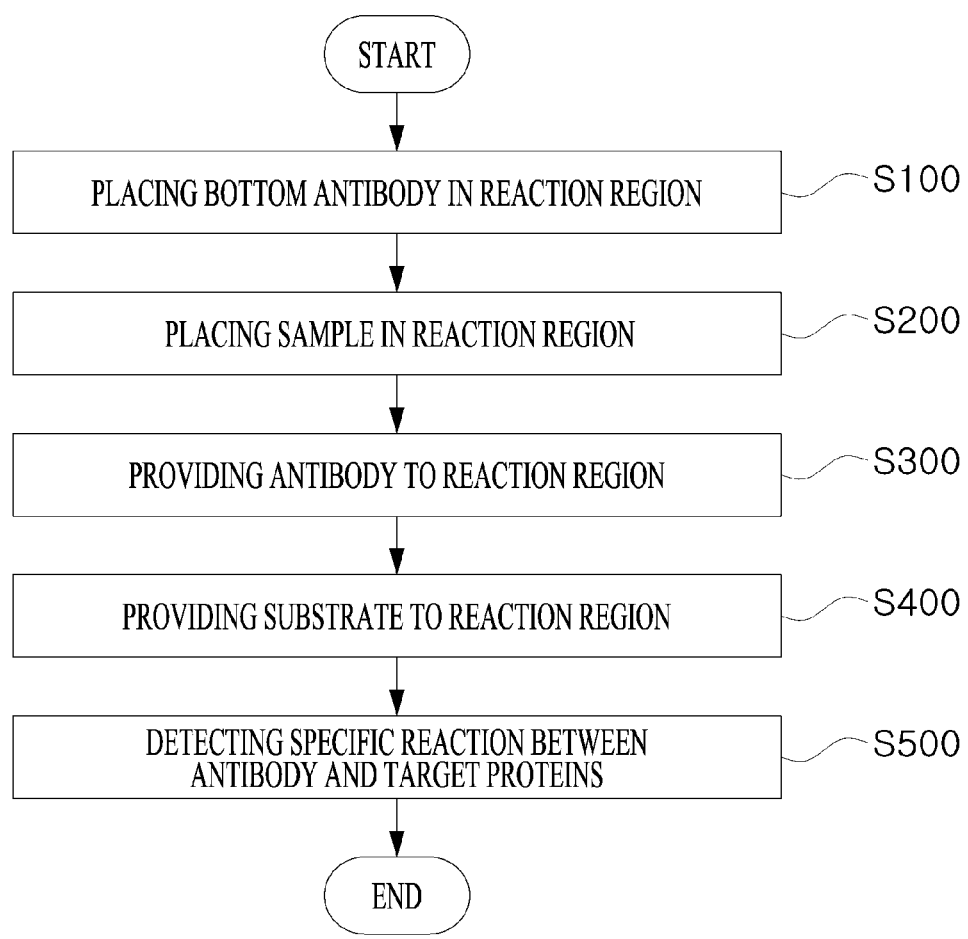
FIG. 67 illustrates a flowchart for describing an immunoassay method using sandwich ELISA as an example of an immunoassay method according to the present application.

FIG. 67 illustrates a flowchart for describing an immunoassay method using sandwich ELISA as an example of an immunoassay method according to the present application.

The immunoassay method using sandwich ELISA according to an embodiment of the present application may include placing bottom antibodies BAB in a reaction region (S100), placing a sample SA in the reaction region (S200), providing antibodies AB to the reaction region (S300), providing a substrate SU to the reaction region (S400), and detecting a specific reaction between the antibodies AB and target proteins TP (S500).

The immunoassay according to the present embodiment may use a plate PL and a patch PA and be performed by sandwich ELISA.

The immunoassay method according to the present embodiment may include fixating antibodies AB on the plate PL, applying a sample SA on the plate PL, and providing the antibodies AB to the plate PL by using the patch PA.

The fixating of the antibodies AB on the plate PL may include fixating the antibodies AB which are dried. The fixating of the antibodies AB on the plate PL may be performed using a coating buffer solution. The fixating of the antibodies AB on the plate PL may include forming a thin film on the plate PL. The thin film may be pre-manufactured and fixated by being attached to the plate PL. The fixating of the antibodies AB may include fixating the antibodies AB so that FC regions of the antibodies AB are in contact with the plate PL. The fixated antibodies AB may be antibodies AB that bind specifically to target antigens to be detected.

The applying of the sample SA on the plate PL may include applying a liquid-phase bodily fluid. For example, the applying of the sample SA on the plate PL may include applying any one of the blood, urine, and suspensions of cells.

Figure 68:
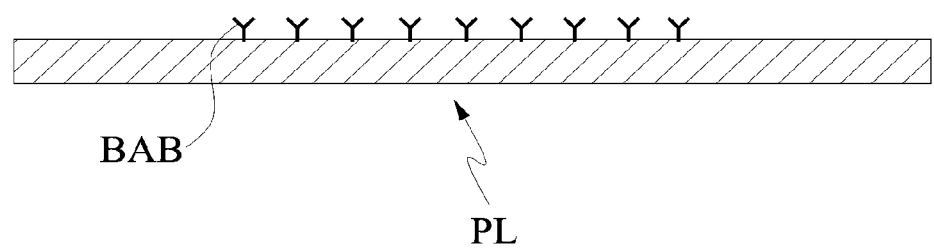
FIG. 68 illustrates a part of an immunoassay method using sandwich ELISA as an example of an immunoassay method according to the present application.
Figure 69:
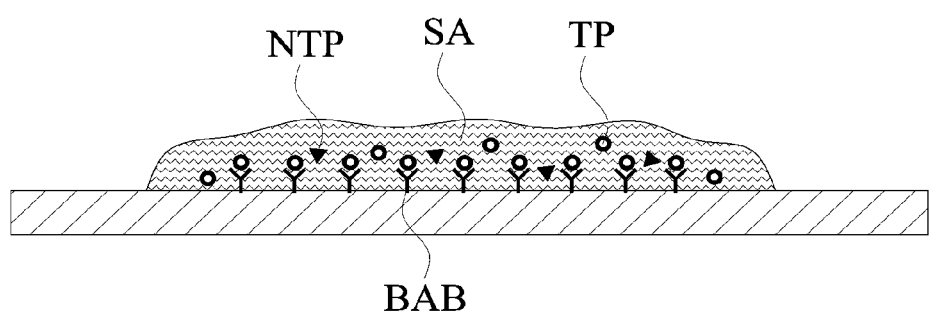
FIG. 69 illustrates a part of an immunoassay method using sandwich ELISA as an example of an immunoassay method according to the present application.

FIGS. 68 and 69 illustrate a part of an immunoassay method using sandwich ELISA according to an embodiment of the present application. According to FIGS. 68 and 69, immunoassay by sandwich ELISA may include fixating antibodies (that is, bottom antibodies BAB) that bind specifically to target proteins TP on a plate PL, and applying a sample SA. The fixating of the bottom antibodies BAB may include fixating the bottom antibodies BAB so that FC regions of the antibodies AB are in contact with the plate PL. By applying the sample SA on the plate PL, the target proteins TP included in the sample SA may bind to the bottom antibodies BAB. In each drawing of the present application, the shapes that represent target proteins or the like do not imply certain properties of the target proteins or the like.

The providing of the antibodies AB to the plate PL by using the patch PA may be performed using the direct technique or the indirect technique. In other words, the providing of the antibodies AB to the plate PL by using the patch PA may include providing antibodies AB that bind specifically to antigens desired to be detected and have enzymes attached thereto. The providing of the antibodies AB to the plate PL by using the patch PA may include providing primary antibodies AB to the plate PL by using the patch PA and providing secondary antibodies AB to the plate PL by using the patch PA.

Therefore, in the providing of the antibodies AB to the plate PL of the present embodiment, the providing of the primary antibodies AB to the plate PL by using the first patch PA and the providing of the secondary antibodies AB to the plate PL by using the second patch PA which have been described above with reference to indirect ELISA or the providing of the antibodies AB by using the patch PA which has been described above with reference to direct ELISA may be applied.

Figure 70:
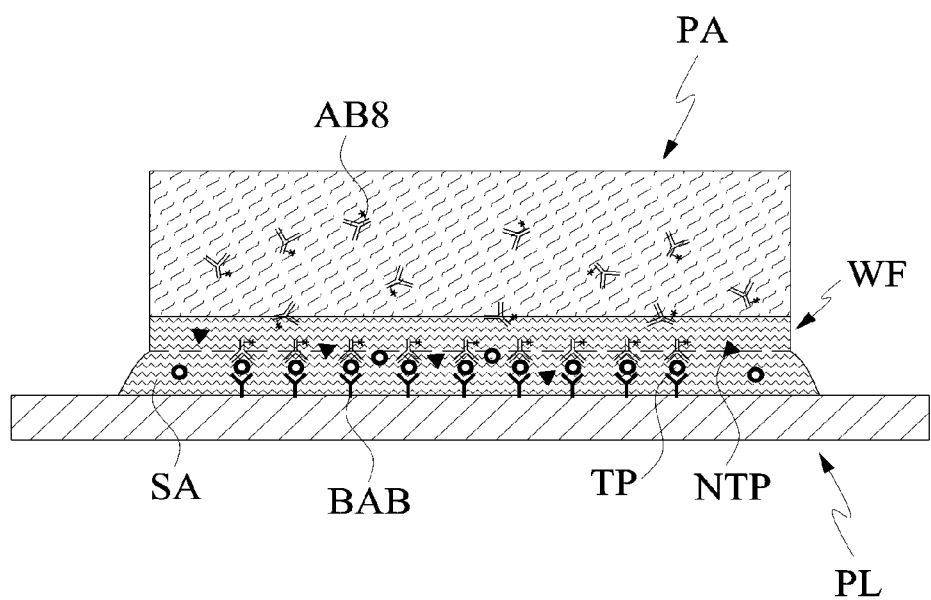
FIG. 70 illustrates a part of an immunoassay method using sandwich ELISA as an example of an immunoassay method according to the present application.
Figure 71:
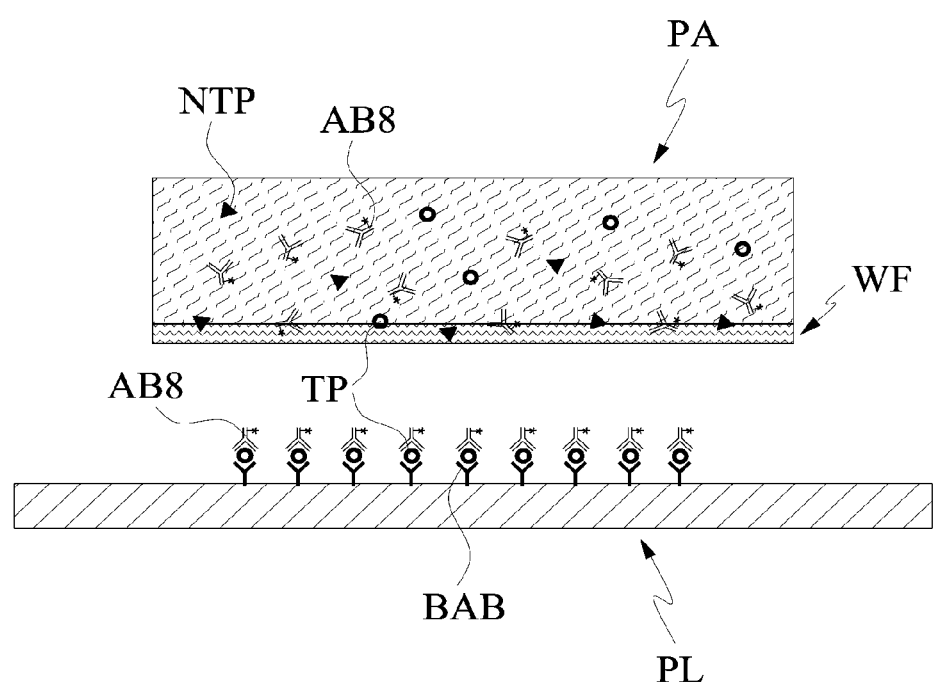
FIG. 71 illustrates a part of an immunoassay method using sandwich ELISA as an example of an immunoassay method according to the present application.

FIGS. 70 and 71 illustrate a part of an immunoassay method using sandwich ELISA according to an embodiment of the present application. According to FIGS. 70 and 71, immunoassay by sandwich ELISA may include providing antibodies AB8 to the plate PL by using a patch PA which contains the antibodies AB8 to which identification labels such as enzymes are attached. The providing of the antibodies AB8 to the plate PL may be performed by contacting the patch PA with the plate PL and then separating the patch PA from the plate PL. In this case, by contacting the patch PA with the plate PL and then separating the patch PA from the plate PL, non-target proteins (NTP) included in the sample SA may be absorbed into the patch PA. The absorption of the non-target proteins NTP into the patch PA may be performed by contacting the patch PA with the plate PL or the sample SA so that a water film WF is formed in the vicinity of a contact region, and causing the non-target proteins NTP to be captured in the water film WF.

The immunoassay method according to the present embodiment may include at least some among providing a substrate SU to the plate PL by using the patch PA, absorbing a residue using a washing patch PA, deterging substances that interfere with detection of the specific binding, providing a predetermined environment to the plate PL, interrupting a reaction on the plate PL, and detecting antigens that have bound specifically to the provided antibodies AB. The details of each step may be similar to those described above with reference to indirect ELISA.

Figure 72:
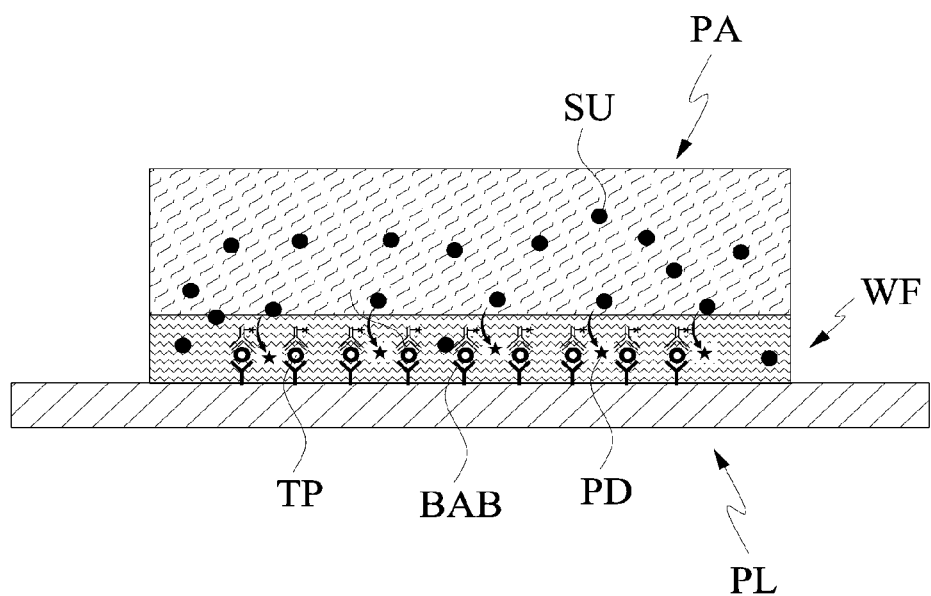
FIG. 72 illustrates a part of an immunoassay method using sandwich ELISA as an example of an immunoassay method according to the present application.
Figure 73:
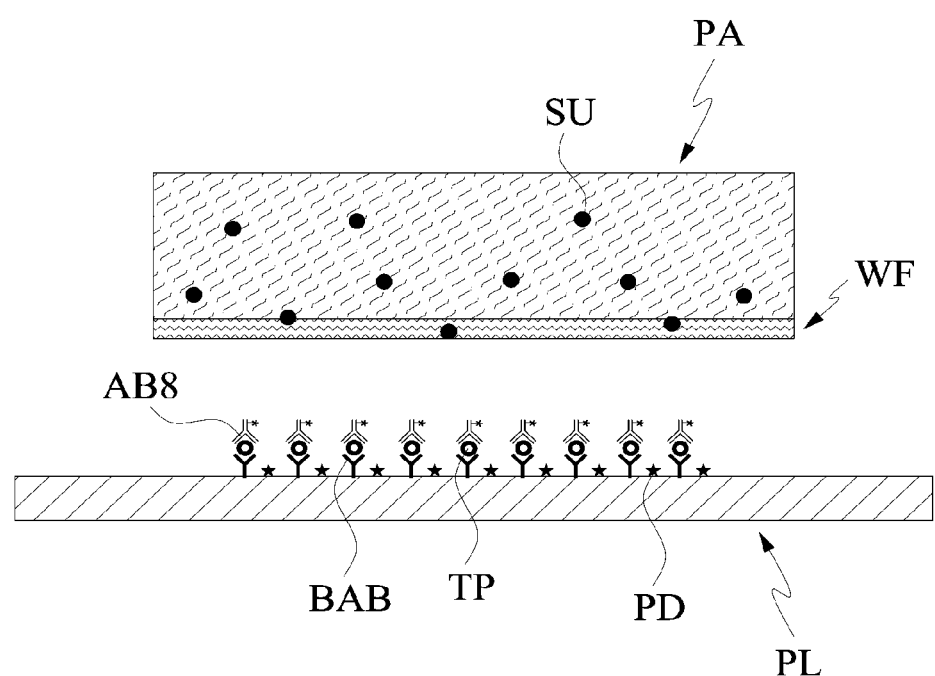
FIG. 73 illustrates a part of an immunoassay method using sandwich ELISA as an example of an immunoassay method according to the present application.

FIGS. 72 and 73 illustrate a part of an immunoassay method using sandwich ELISA according to an embodiment of the present application. According to FIGS. 72 and 73, immunoassay by sandwich ELISA may include providing a substrate SU to the plate PL by using a substrate SU patch PA. The providing of the substrate SU may be performed by contacting the patch PA which contains the substrate SU with the plate PL so that, through a water film WF formed in the vicinity of a contact region, the substrate SU is allowed to move to the plate PL. The substrate SU may produce a product PD or be converted into the product PD through a chemical reaction catalyzed by enzymes attached to antibodies AB located on the plate PL.

4.3.4 Multi-Target

Immunoassay of the present application may be performed to simultaneously detect a plurality of targets. In other words, a plurality of targets that cause a single disease may be simultaneously detected, or a plurality of targets that cause multiple diseases may be simultaneously detected. For example, in diagnosis of leukemia, a plurality of antigens that are involved in leukemia may be simultaneously detected. Also, for example, target proteins TP that cause multiple different diseases such as leukemia and Zika virus may be simultaneously detected.

Here, the simultaneous detection may refer to detection of a plurality of targets from a single plate PL, as well as detection of each target in partially overlapping time sections.

The simultaneous detection of the plurality of targets may be differently performed in accordance with means of performing the above-described immunoassay method. Methods of detecting a plurality of targets in accordance with means of performing the above-described immunoassay method will be described below. Description of content which has been described above with reference to the above embodiments will be omitted.

4.3.4.1 Indirect+Multi-Target

An immunoassay method according to an embodiment of the present application may include placing a sample SA in a reaction region (S200) and providing antibodies AB to the reaction region (S300). In this case, multiple target proteins TP may be present, the multiple target proteins TP may include first target proteins TP and second target proteins TP, and the patch PA may contain first antibodies AB that react specifically with the first target proteins TP and first antibodies AB that react specifically with the second target proteins TP.

Alternatively, type of target proteins TP may be one or more, patch PA that contain antibodies AB may be one or more, the target proteins TP may include first target proteins TP and second target proteins TP, and the plurality of patches PA may include a first patch PA that contains first antibodies AB that react specifically with the first target proteins TP and a second patch PA that contains second antibodies AB that react specifically with the second target proteins TP.

According to an embodiment of the present application, an immunoassay method for detecting a plurality of targets using indirect ELISA as described above may include fixating a sample SA on the plate PL, providing multiple types of primary antibodies AB to the plate PL, and providing secondary antibodies AB to the plate PL by using a patch PA.

The fixating of the sample SA on the plate PL may be similar to that in the above-described embodiment of the immunoassay method using indirect ELISA. However, when immunoassay for detecting a plurality of targets is performed by indirect ELISA as in the present embodiment, the sample SA may be distributed throughout a single region on the plate PL or distributed throughout a plurality of divided regions.

The providing of the multiple types of primary antibodies AB to the plate PL may include providing multiple types of primary antibodies AB, which specifically bind to multiple different types of antigens, to the plate PL.

The providing of the multiple types of primary antibodies AB to the plate PL may include providing multiple types of primary antibodies AB contained in a single patch PA to the plate PL. The providing of the multiple types of primary antibodies AB to the plate PL may include providing multiple types of primary antibodies AB to the plate PL by using a plurality of patches PA. The providing of the multiple types of primary antibodies AB may include using a first patch PA that contains first primary antibodies AB and a second patch PA that contains second primary antibodies AB to provide the first primary antibodies AB and the second primary antibodies AB to the plate PL. In other words, the providing of the multiple types of primary antibodies AB may include using the plurality of patches PA that contain the multiple types of primary antibodies AB to provide the primary antibodies AB.

The providing of the primary antibodies AB to the plate PL by using a patch PA may include providing the primary antibodies AB to a plurality of divided regions of the plate PL with a single patch PA. The plurality of regions may include a first region and a second region, and the providing of the primary antibodies AB to the plurality of regions may include providing the first primary antibodies AB to the first region and providing the second primary antibodies AB to the second region. In other words, the providing of the primary antibodies AB to the plurality of regions may include providing different primary antibodies AB to each of the plurality of regions by the plurality of patches PA.

The providing of the multiple types of primary antibodies AB to the plate PL by using the plurality of patches PA may include simultaneously contacting the plurality of patches PA with the plate PL for at least a certain amount of time so that the primary antibodies AB contained in each of the patches PA are provided to the plate PL. The providing of the multiple types of primary antibodies AB to the plate PL by using the plurality of patches PA may include sequentially bringing the plurality of patches PA into contact with the plate PL such that regions of the plate PL that sequentially come into contact with the plurality of patches PA at least partially overlap, and the primary antibodies AB contained in each of the patches PA are provided to the plate PL.

The providing of the secondary antibodies AB to the plate PL by using the patch PA may include providing first secondary antibodies AB, which specifically bind specifically to a first type of primary antibodies AB, and second secondary antibodies AB, which specifically bind specifically to a second type of primary antibodies AB, to the plate PL by using a patch PA. For example, the providing of the secondary antibodies AB to the plate PL by using the patch PA may include providing multiple types of secondary antibodies AB, which have properties of binding specifically to multiple different types of primary antibodies AB, to the plate PL. The providing of the secondary antibodies AB to the plate PL by using the patch PA may include providing a single type of secondary antibodies AB, which have a property of commonly binding specifically to multiple types of primary antibodies AB, to the plate PL. In other words, the secondary antibodies AB may be multiple types of secondary antibodies AB which have a property of binding specifically to each of multiple types of primary antibodies AB used in diagnosis, or may be a single type of secondary antibodies AB which have a property of commonly binding species-specifically to multiple types of primary antibodies AB used in the diagnosis.

The providing of the secondary antibodies AB to the plate PL by using the patch PA may include providing multiple types of secondary antibodies AB or a single type of secondary antibodies AB, which are contained in a single patch PA, to the plate PL. The providing of the secondary antibodies AB to the plate PL by using the patch PA may include providing multiple types of secondary antibodies AB or a single type of secondary antibodies AB, which are contained in a plurality of patches PA, to the plate PL.

The providing of the secondary antibodies AB to the plate PL by using the patch PA may include providing the secondary antibodies AB to a plurality of divided regions of the plate PL with a single patch PA. The providing of the secondary antibodies AB to the plurality of regions may include providing multiple types of secondary antibodies AB to each of the plurality of regions.

The providing of the secondary antibodies AB to the plate PL by using a plurality of patches PA may include simultaneously contacting the plurality of patches PA with the plate PL for at least a predetermined amount of time so that the secondary antibodies AB contained in each of the patches PA are provided to the plate PL. The providing of the secondary antibodies AB to the plate PL by using the plurality of patches PA may include sequentially bringing the plurality of patches PA into contact with the plate PL such that regions of the plate PL that sequentially come into contact with the plurality of patches PA at least partially overlap, and the secondary antibodies AB contained in each of the patches PA are provided to the plate PL.

The method of performing immunoassay for detecting a plurality of targets according to the present embodiment may include providing a substrate SU by using a patch PA. The details of the providing of the substrate SU by using the patch PA are the same as those described above with reference to the embodiment of the immunoassay method using indirect ELISA. However, more than one types of substrates SU may be used. In other words, a single type of substrate SU may be used when a single type of secondary antibodies AB are used, and a single type of substrate SU or multiple types of substrate SU may be used when multiple types of secondary antibodies AB are used.

The method of performing immunoassay for detecting a plurality of targets according to the present embodiment may include determining the presence of each of a plurality of targets from the plate PL. The details are the same as those described above with reference to the embodiment of the immunoassay method using indirect ELISA.

A few embodiments of performing immunoassay for detecting a plurality of targets according to the present embodiment will be described below.

As a specific example of a method of performing immunoassay for detecting a plurality of targets, when different primary antibodies AB are provided to each region of the plate PL by the plurality of patches PA, the providing of the secondary antibodies AB may include simultaneously providing the secondary antibodies AB to each of the regions by a single patch PA. When multiple types of primary antibodies AB are provided to a plurality of divided regions of the plate PL, a single type of secondary antibodies AB may be provided to the plurality of regions. In this case, the providing of the secondary antibodies AB to the plurality of regions may be performed using a single patch PA or a plurality of small patches PA that correspond to the respective regions. Although performance of diagnosis is simplified when the single patch PA is used, when the plurality of small patches PA are used, since there is no risk of undesired transferring of substance through the patches PA and it is sufficient that detection be performed for each region, more accurate detection may be possible.

As another specific example, when regions of a single plate PL that sequentially come into contact with the plurality of patches PA at least partially overlap such that multiple types of primary antibodies AB contained in the patches PA are provided to the plate PL, the providing of the secondary antibodies AB may include providing multiple types of secondary antibodies AB, which have properties of binding specifically to the multiple types of primary antibodies AB, to the plate PL through a single patch PA. In this case, the multiple types of secondary antibodies AB having the properties of binding specifically to the multiple types of primary antibodies AB may be detected in accordance with different identification labels.

Alternatively, the providing of the secondary antibodies AB may include providing a single type of secondary antibodies AB, which have properties of binding specifically to the multiple types of primary antibodies AB, to the plate PL through a single patch PA. Such a method may be used in determining a presence of a disease when an antigen with which multiple types of primary antibodies AB react specifically is a cause of the corresponding disease.

Alternatively, the secondary antibodies AB may include first secondary antibodies AB, which have a property of binding specifically to a first type of primary antibodies AB, and second secondary antibodies AB, which have a property of binding specifically to a second type of primary antibodies AB, and the providing of the secondary antibodies AB may include providing the first secondary antibodies AB to a first region located on the plate PL and providing the second secondary antibodies AB to a second region located on the plate PL. For example, the providing of the secondary antibodies AB may include providing multiple types of secondary antibodies AB, which have properties of respectively binding specifically to the multiple types of primary antibodies AB, to a plurality of divided regions located on the plate PL. In this case, targets to be detected may be changed in accordance with the divided regions, and result acquisition may be facilitated.

4.3.4.2 Direct+Multi-Target

According to an embodiment of the present application, an immunoassay method for detecting a plurality of targets using direct ELISA described above may include fixating a sample SA on the plate PL and providing multiple types of antibodies AB to the plate PL by using the patch PA.

The fixating of the sample SA on the plate PL may be similar to that in the above-described method of performing immunoassay by direct ELISA. However, when immunoassay for detecting a plurality of targets is performed by direct ELISA as in the present embodiment, the sample SA may be distributed throughout a single region on the plate PL or distributed throughout a plurality of divided regions.

When multiple types of antibodies AB are provided to the plate PL by using the patch PA, the multiple types of antibodies AB may include first antibodies AB, which have a property of binding specifically to first antigens, and second antibodies AB, which have a property of binding specifically to second antigens. First enzymes attached to the first antibodies AB and second enzymes attached to the second antibodies AB may be different types of enzymes.

The providing of the multiple types of antibodies AB to the plate PL by using the patch PA may include providing multiple types of antibodies AB to the plate PL by using the patch PA. The providing of the multiple types of antibodies AB may include providing first antibodies AB which have a property of binding specifically to first antigens and second antibodies AB which have a property of binding specifically to second antigens. Also, the providing of the multiple types of antibodies AB may include providing multiple types of antibodies AB which have properties of respectively binding specifically to a plurality of different antigens (that is, a plurality of targets to be detected). Different types of identification elements may be attached to the multiple types of antibodies AB. Multiple types of enzymes may be attached to the multiple types of antibodies AB respectively.

The providing of the multiple types of antibodies AB may include providing multiple types of antibodies AB contained in a single patch PA to the plate PL. The providing of the multiple types of antibodies AB may include providing multiple types of antibodies AB to the plate PL by using a plurality of patches PA. The plurality of patches PA may include a first patch PA and a second patch PA, and the providing of the multiple types of antibodies AB by using the plurality of patches PA may include providing first antibodies AB by using the first patch PA and providing second antibodies AB by using the second patch PA. In this case, the first antibodies AB and the second antibodies AB may be different from each other. The providing of the multiple types of antibodies AB by using the plurality of patches PA may be performed using a plurality of patches PA which respectively contain the multiple types of antibodies AB.

The providing of the antibodies AB to the plate PL by using the patch PA may include providing the antibodies AB to a plurality of divided regions of the plate PL with a single patch PA. The plurality of regions may include a first region and a second region, and the providing of the antibodies AB to the plurality of regions may include providing first antibodies AB to the first region by using a first patch PA that contains the first antibodies AB and providing second antibodies AB to the second region by using a second patch PA that contains the second antibodies AB. The providing of the antibodies AB to the plurality of regions may include providing different antibodies AB to the plurality of regions with the plurality of patches PA.

The providing of the multiple types of antibodies AB to the plate PL by using the plurality of patches PA may include simultaneously contacting the plurality of patches PA with the plate PL for at least a certain amount of time so that the antibodies AB contained in each of the patches PA are provided to the plate PL. The providing of the multiple types of antibodies AB to the plate PL by using the plurality of patches PA may include sequentially contacting the plurality of patches PA with the plate PL such that regions of the plate PL that sequentially come into contact with the plurality of patches PA at least partially overlap, and the antibodies AB contained in each of the patches PA are provided to the plate PL.

The method of performing immunoassay for detecting a plurality of targets by direct ELISA may include providing a substrate SU by using a patch PA or determining a presence of each of a plurality of targets from the plate PL. Details of each step may be similar to those described above with reference to the embodiment of the immunoassay method using direct ELISA.

4.3.4.3 Sandwich+Multi-Target

According to an embodiment of the present application, an immunoassay method for detecting a plurality of targets using sandwich ELISA described above may include fixating antibodies AB on the plate PL, applying a sample SA on the plate PL, and providing the antibodies AB to the plate PL by using a patch PA.

The fixating of the antibodies AB on the plate PL may include fixating multiple types of antibodies AB on the plate PL. The multiple types of antibodies AB may include first antibodies AB which have a property of binding specifically to first antigens to be detected and second antibodies AB which have a property of binding specifically to second antigens to be detected. The multiple types of antibodies AB may be multiple types of antibodies AB that have properties of respectively binding specifically to multiple types of antigens to be detected.

The first antibodies AB may be fixated on a first region located on the plate PL, and the second antibodies AB may be fixated on a second region located on the plate PL. The multiple types of antibodies AB may be respectively fixated on a plurality of divided regions located on the plate PL. The multiple types of antibodies AB may be fixated on a single region located on the plate PL.

The applying of the sample SA on the plate PL may include applying the sample SA on a region of the plate PL on which the antibodies AB are fixated. The applying of the sample SA may include applying a liquid-phase sample SA. In this case, the immunoassay may be performed while the liquid-phase sample SA is applied or performed after the liquid-phase sample SA is applied and fixated.

The applying of the sample SA on the plate PL may include applying the sample SA on a single region located on the plate PL or applying the sample SA on a first region and a second region located on the plate PL. The applying of the sample SA on the plate PL may include applying the sample SA on a single region located on the plate PL or applying the sample SA on each of a plurality of divided regions located on the plate PL.

The applying of the antibodies AB on the plate PL by using the patch may be similar to those in the above-described immunoassay method for detecting a plurality of targets by using direct ELISA and immunoassay method for detecting a plurality of targets by using indirect ELISA. In other words, the applying of the antibodies AB on the plate PL by using the patch PA may be similar to the providing of the multiple types of antibodies AB to the plate PL by using the patch PA in the above-described immunoassay method for detecting a plurality of targets using direct ELISA. Alternatively, the applying of the antibodies AB to the plate PL by using the patch PA may be similar to the providing of the multiple types of primary antibodies AB to the plate PL and the providing of the secondary antibodies AB to the plate PL by using the patch PA in the above-described immunoassay method for detecting a plurality of targets using indirect ELISA.

The method of performing immunoassay for detecting a plurality of targets by sandwich ELISA may further include providing a substrate SU by using a patch PA or determining a presence of each of a plurality of targets from the plate PL. Details of each step may be similar to those described above with reference to the embodiment of the immunoassay method using sandwich ELISA or the immunoassay method for detecting a plurality of targets by indirect ELISA or direct ELISA.

As described above, according to a method of performing immunoassay according to the present application, a plurality of targets may be detected at once. In this case, a plurality of targets to be detected may constitute a predetermined target set or may be selectively configured every time diagnosis is performed. When the plurality of targets constitute a predetermined set, diagnosis may become prompt, and various control groups may be acquired. When the plurality of targets are selectively configured every time diagnosis is performed, it is expected that patient-specific diagnosis would be possible, and the range of diseases that may be examined with one diagnosis would be widened further.

4.3.4.4 Plate: Plurality of Regions

A method of performing immunoassay according to the present embodiment may be performed using a plate PL having a plurality of unit regions. In other words, the plate PL may have a plurality of unit regions and receive a substance from the patch PA through each of the unit regions.

The plate PL may include a plurality of divided regions, that is, a plurality of unit regions. The unit regions may be arranged in a checkerboard form on the plate PL. The unit regions may be disposed in parallel in one direction on the plate PL. The unit regions may be disposed in the form that corresponds to the plurality of patches PA or the patch PA cluster.

The plurality of unit regions may be partitioned. The unit regions may include a first region and a second region. In this case, the first region and the second region may have similar polarities, and the polarity of the first region may be different from a polarity of a third region other than the first region or the second region. Accordingly, the first region and the second region may be partitioned from each other. Heights of the first region and the second region from an undersurface of the plate PL may be different from a height of the third region from the undersurface of the plate PL, and accordingly, the first region and the second region may be partitioned from each other.

Different substances may be applied or fixated on different unit regions. The unit regions may include a first unit region and a second unit region, antibodies AB that bind specifically to first antigens may be fixated on the first unit region, and antibodies AB that bind specifically to second antigens may be fixated on the second unit region. The first antigens and the second antigens may be different from each other. Antibodies AB that bind specifically to different antigens may be fixated on the unit regions. The unit regions to which different antibodies AB are bound may be used in detecting different antigens with sandwich ELISA.

When immunoassay is performed using the plurality of patches PA or the patch PA cluster, the unit regions may include a first unit region and a second unit region, a first patch may be brought into contact with the first unit region, and a second patch PA may be brought into contact with the second unit region. The first patch PA and the second patch PA may be different from each other. Different patches PA may come into contact with the unit regions. In other words, the arrangements, forms, and the like of unit patches PA that constitute the patch PA cluster and the unit regions located on the plate PL may correspond to each other. The patches PA and the unit regions may be suitably matched in order to acquire a desired result.

4.3.4.5 Patch: Cluster

A method of performing immunoassay according to the present embodiment may be performed using a plurality of patches PA. The plurality of patches PA may contain a substance and provide the substance to the plate PL.

The plurality of patches PA may contain different substances and provide the substances contained therein to the plate PL. For example, the plurality of patches PA may contain antibodies AB that bind specifically to different antigens. As another example, the plurality of patches PA may contain secondary antibodies AB that bind specifically to different primary antibodies AB. As yet another example, the plurality of patches PA may contain substrates SU, reactions of which are induced by different enzymes.

The plurality of patches PA may form a patch PA cluster. For example, the plurality of patches PA may be a cluster of unit patches PA which contain different substances. The cluster may be used to simultaneously provide substances to the plate PL. The plurality of unit patches PA which constitute the patch PA cluster may be manufactured in a standardized form.

The patch PA cluster may be manufactured in a form of a cartridge. In other words, the configuration of the plurality of unit patches PA which constitute the patch PA cluster may be changed according to purposes. The patch cartridge may be particularly useful when it is desired to implement personalized diagnosis in which a target disease to be diagnosed is changed for each individual.

The unit patches PA which constitute the patch PA cluster may be arranged in a checkerboard form. The unit patches PA which constitute the patch PA cluster may be disposed in parallel in one direction.

According to an embodiment of the present application, a patch PA cluster that includes a plurality of patches PA may be provided. Particularly, a patch PA cluster that includes a plurality of antibody AB-containing patches PA may be provided.

In the patch PA cluster including the plurality of antibody AB-containing patches PA, the antibody AB-containing patch PA may include antibodies AB that react specifically with target proteins TP and a mesh structural body NS forming micro-cavities in which the antibodies AB are contained.

In this case, the plurality of antibody AB-containing patches PA may include a first antibody AB-containing patch PA and a second antibody AB-containing patch PA, and target proteins TP with which first antibodies AB, which are contained in the first antibody AB-containing patch PA, react specifically may be different from target proteins TP with which second antibodies AB, which are contained in the second antibody AB-containing patch PA, react specifically.

4.3.4.6 Patch: Blend Patch

A method of performing immunoassay according to the present embodiment may be performed using a patch PA that contains multiple types of substances. The patch PA may contain multiple types of substances and provide the multiple types of substances to the plate PL.

The patch PA may contain first antibodies AB that bind specifically to first antigens and second antibodies AB that bind specifically to second antigens. Also, the patch PA may include first antibodies AB that bind specifically to first primary antibodies AB and second antibodies AB that bind specifically to second primary antibodies AB. For example, the patch PA may contain multiple types of antibodies AB that respectively bind specifically to multiple types of antigens. Also, for example, the patch PA may contain multiple types of antibodies AB that respectively bind specifically to multiple types of primary antibodies AB.

An antibody AB-containing patch PA according to an embodiment of the present application may include antibodies AB that react specifically with target proteins TP and a mesh structural body NS provided as a mesh structural body NS which is configured to come into contact with a reaction region in which the target proteins TP are located so as to provide some of the contained antibodies AB to the reaction region. In this case, multiple target proteins TP may be present, the multiple target proteins TP may include first target proteins TP and second target proteins TP, and the antibodies AB may include first antibodies AB which react specifically with the first target proteins TP and second antibodies AB which react specifically with the second target proteins TP.

4.3.5 Smearing

A method of performing immunoassay of the present application may include applying a sample SA on a plate PL or applying and fixating the sample SA on the plate PL.

The applying of the sample SA on the plate PL may include smearing the sample SA in a monolayer or in a form of a thin film that similar to the monolayer. The applying and fixating of the sample SA on the plate PL may include smearing the sample SA in a monolayer or in a form of a thin film that corresponds to the monolayer and fixating the sample SA.

When diagnosis is performed with a sample SA being smeared in a form corresponding to a monolayer as described above, an effective surface area between the sample SA smeared on the plate PL and patches PA which are brought into contact with the plate PL may be maximized. In other words, by smearing the sample SA and contacting the patch PA with the sample SA to perform target detection, an effective result may be acquired even with a small amount of sample SA. A reaction region may be very simply implemented in comparison to conventional immunoassay methods in which a region in which a sample SA is distributed is complexly designed to expand an effective surface area.

4.3.6 Reaction Detection

An immunoassay method according to the present application may include detecting a presence of target proteins TP from a sample SA. The immunoassay method according to the present application may include detecting a presence of target antigens from the sample SA. The detecting of the presence of the target proteins TP or the target antigens may refer to quantitatively measuring the amount of target proteins TP or target antigens included in the sample SA.

The immunoassay method according to the present application may include detecting antigens (that is, target antigens) to which antibodies AB have bound specifically, and the detecting of the antigens may include detecting a chemical reaction of a substrate SU catalyzed by enzymes attached to the antibodies AB or other antibodies AB, which bind specifically to the antibodies AB, or a product PD due to the chemical reaction.

4.3.6.1 Colorimetric Measurement

In the immunoassay method of the present application, the detecting of the chemical reaction of the substrate SU catalyzed by the enzymes attached to the antibodies AB may be performed by a method of performing colorimetric measurement.

Specifically, the detecting of the product PD by a colorimetric technique may be understood as below. The enzymes attached to the antibodies AB (in the indirect technique, the enzymes attached to the secondary antibodies AB) may convert the substrate SU into a precipitation that exhibits color. When the precipitation is accumulated, a stain may be formed, and color of the formed stain may be measured to detect the product PD.

When the enzymes are HRPs and 3,3'-Diaminobenzidine (DAB) is used as the substrate SU, the DAB may generate a brown precipitation due to the HRPs. Also, when the enzymes are HRPs and the substrate SU is 4-chloro-1-naphthol (4CN), the 4CN may generate a violet precipitation due to the HCNs. When the enzymes are APs and the substrate SU is 5-Bromo-4-chloro-3-indolyl phosphate (BCIP), the BCIP may generate a violet precipitation due to the APs. In this case, the detecting of the product PD may be performed by detecting the brown or violet precipitation.

The measuring of the color may be performed by using a spectrophotometer and quantitatively measuring the color development. The measuring of the color may be performed by detecting light that has been emitted from a light source and has passed through the plate PL. The measuring of the color may be performed by measuring light absorption. In this case, preferably, a plate PL which is transparent and has a flat bottom may be used.

4.3.6.2 Luminescence Detection

In the immunoassay method of the present application, the detecting of the chemical reaction of the substrate SU catalyzed by the enzymes attached to the antibodies AB may be performed by detecting luminescence.

The detecting of the luminescence may include detecting luminescence due to the chemical reaction of the substrate SU. When the enzymes are HRPs, the detecting of the luminescence may include using luminol as the substrate SU to detect light generated.

The detecting of the luminescence may be performed using an X-ray film, a complementary metal-oxide semiconductor (CMOS) camera, or a charge coupled device (CCD) camera. The measuring of the luminescence may be performed by detecting light emitted from the bottom of the plate PL or a solution above the bottom of the plate PL. The measuring of the luminescence may be performed using a luminometer. When the luminescence is measured, preferably, an opaque black plate or an opaque white plate may be used as the plate PL.

4.3.6.3 Fluorescence Detection

In the immunoassay method of the present application, the detecting of the product PD due to the chemical reaction of the substrate SU catalyzed by the enzymes attached to the antibodies AB may be performed by detecting fluorescence.

The detecting of the fluorescence may include detecting fluorescence emitted from fluorophores attached to the antibodies AB (in the indirect technique, the secondary antibodies AB). The detecting of the fluorescence may include detecting fluorescence emitted from the product PD which is produced due to the chemical reaction of the substrate SU catalyzed by the enzymes. More specifically, the enzymes may cut phosphate groups from the substrate SU and catalyze the substrate SU to generate a fluorescent product PD, and the immunoassay may be performed by detecting the generated fluorescence.

The detecting of the fluorescence may be performed by making light be incident on the plate PL and measuring fluorescence emitted from the plate PL. The measuring of the fluorescence may be performed using a fluorometer to which a filter is attached. When the fluorescence is measured, preferably, an opaque black plate or an opaque white plate may be used as the plate PL.

4.3.6.4 Electrochemical (EC) Sensor

Result detection in an immunoassay of the present application may also be performed using an electrochemical method. For example, a change in an electrochemical characteristic that occurs on the plate PL due to the antibodies AB that have bound specifically to the sample SA fixated on the plate PL may be measured. Alternatively, a change in an electrochemical characteristic of the patch PA that occurs due to the patch PA providing the antibodies AB to the plate PL may also be measured. When a result is detected using an electrochemical method as described above, the substrate SU may be selectively provided on the plate PL.

4.3.6.5 Image Analysis

Result detection in an immunoassay according to the present application may be performed using image acquisition. In other words, a colorimetric (or color development) image, a luminescence image, or a fluorescence image may be acquired and used in diagnosis. For the images, a single image of an entire region may be acquired, or partial images of the entire region may be acquired separately and the acquired images of the partial images may be combined into a single image. Positions at which target antigens/antibodies AB are distributed, shape of cells, distribution of target proteins TP in a tissue, or the like may be checked from the acquired images. Also, by analyzing the acquired images, positions of target proteins TP, target antigens/antibodies AB, or the like and partial images of the targets may be acquired.

4.3.7 Cell Counting

Result detection in an immunoassay according to the present application may be performed by measuring an amount of specific proteins included in a sample SA. In other words, immunoassay of the present application may include measuring an amount of target proteins TP, which are included in a sample SA to be diagnosed, by using an antigen-antibody reaction. For example, result detection in an immunoassay according to the present application may include counting the number of specific cells (that is, target cells) included in a sample SA to be diagnosed.

Immunoassay according to an embodiment of the present application may be performed to detect multiple target proteins TP by using a patch of the present application. In this case, an immunoassay method according to an embodiment of the present application may include placing a sample SA to be diagnosed in a reaction region (S20), providing first antibodies to the reaction region (S30), and providing second antibodies to the reaction region (S40) (see FIG. 46).

The placing of the sample SA to be diagnosed in the reaction region (S20) may be similar to that in other embodiments described above. Also, details of the providing of the first antibodies or the second antibodies to the reaction region may be similar to those in the above-described other embodiments of the present application.

The providing of the first antibodies to the reaction region (S30) may include using a patch that contains the first antibodies which react specifically with first target proteins so as to provide the first antibodies to the reaction region.

The providing of the second antibodies to the reaction region (S40) may include using a patch that contains the second antibodies which react specifically with second target proteins so as to provide the second antibodies to the reaction region.

Figure 81:
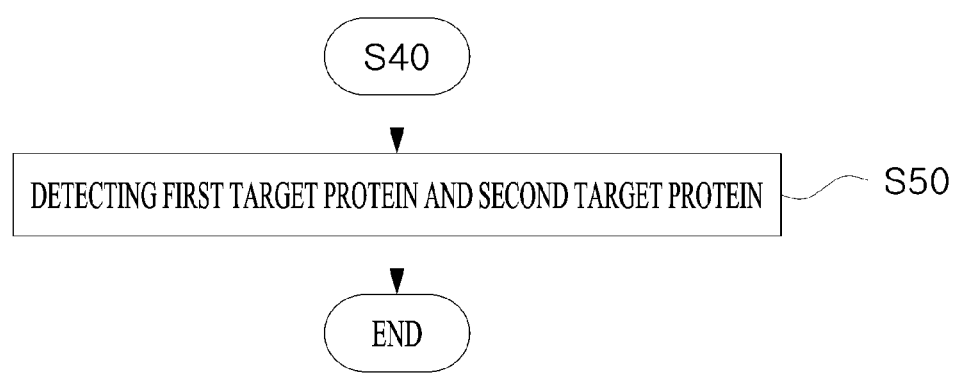
FIG. 81 illustrates a flowchart for describing an embodiment of an immunoassay method according to the present application.

The immunoassay method according to the present embodiment may further include detecting first target proteins TP and second target proteins TP (S50) (see FIG. 81).

In the detecting of the first target proteins TP and the second target proteins TP (S50), the detecting of the first target proteins may include detecting first fluorescence that is detected from fluorescence labels attached to the first antibodies bound specifically to the first target proteins TP, and the detecting of the second target proteins TP may include detecting second fluorescence that is detected from fluorescence labels attached to the second antibodies bound specifically to the second target proteins TP.

In this case, a wavelength band from which the first fluorescence is detected may be different from a wavelength band from which the second fluorescence is detected.

Figure 82:
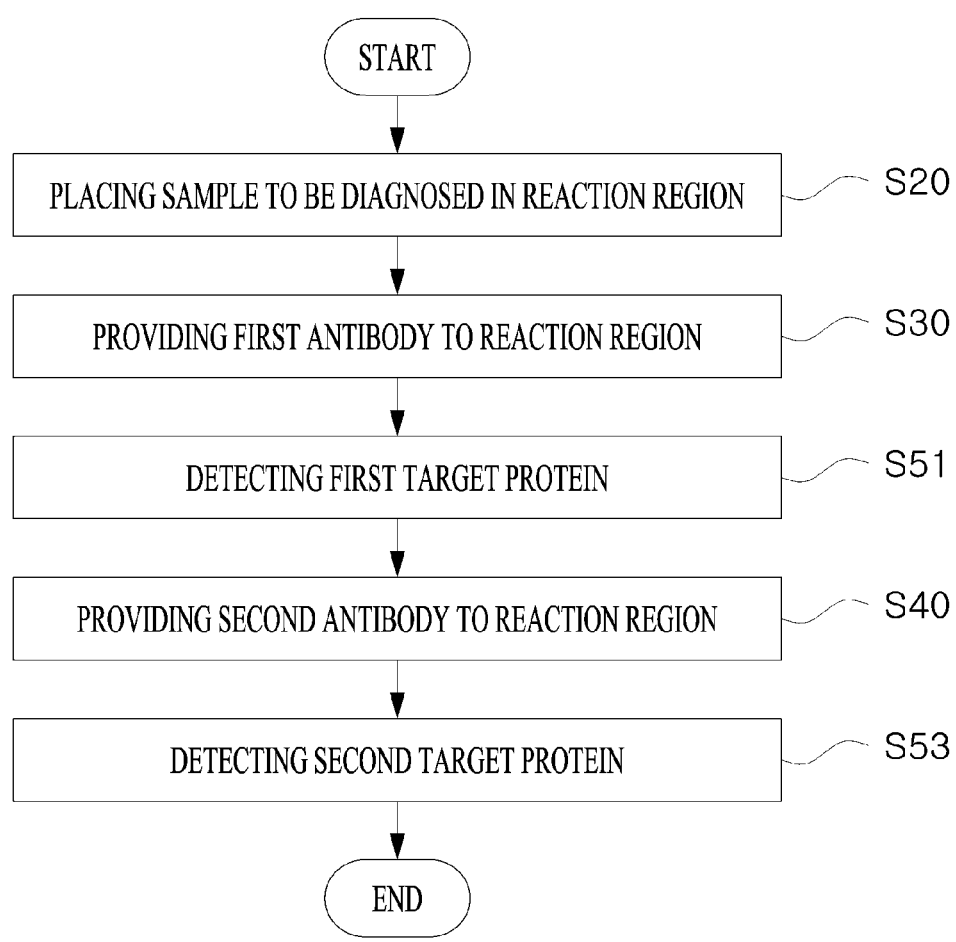
FIG. 82 illustrates a flowchart for describing an embodiment of an immunoassay method according to the present application.

An immunoassay method according to the present embodiment may include placing a sample SA to be diagnosed in a reaction region (S20), providing first antibodies to the reaction region (S30), detecting first target proteins TP (SM), providing second antibodies to the reaction region (S40), and detecting second target proteins TP (S52) (see FIG. 82).

In other words, the immunoassay method according to the present application may further include, after the providing of the first antibodies to the reaction region (S30), the detecting of the first target proteins (S51), and also include, after the providing of the second antibodies to the reaction region (S40), the detecting of the second target proteins (S53).

In this case, the detecting of the first target proteins TP may include detecting first fluorescence that is detected from fluorescence labels attached to the first antibodies bound specifically to the first target proteins TP, and the detecting of the second target proteins TP may include detecting second fluorescence that is detected from fluorescence labels attached to the second antibodies bound specifically to the second target proteins TP.

Here, a wavelength band from which the first fluorescence is detected may at least partially overlap a wavelength band from which the second fluorescence is detected, and the detecting of the fluorescence may be performed by comparing fluorescence that is detected from the sample SA after the second antibodies are provided to the reaction region and fluorescence that is detected from the sample SA before the second antibodies are provided to the reaction region.

Figure 83:
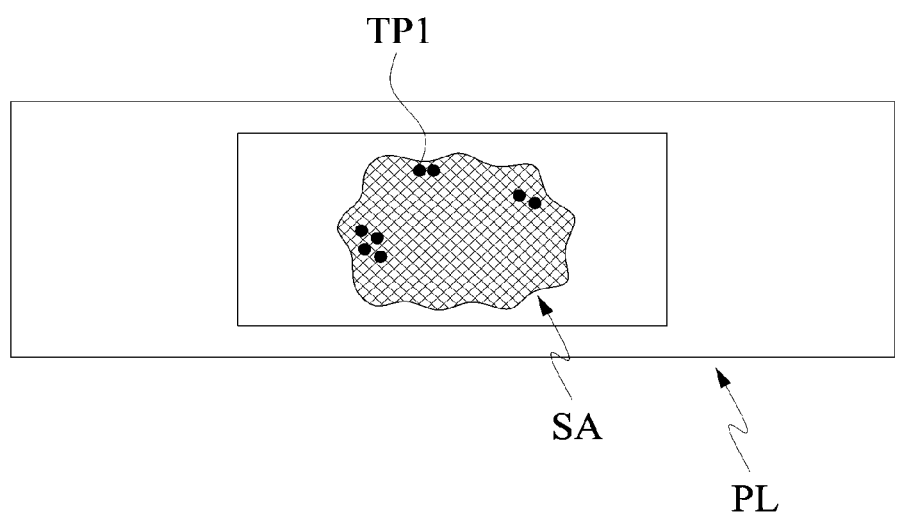
FIG. 83 illustrates a part of a case in which a plurality of target proteins are detected in an immunoassay method according to the present application.
Figure 84:
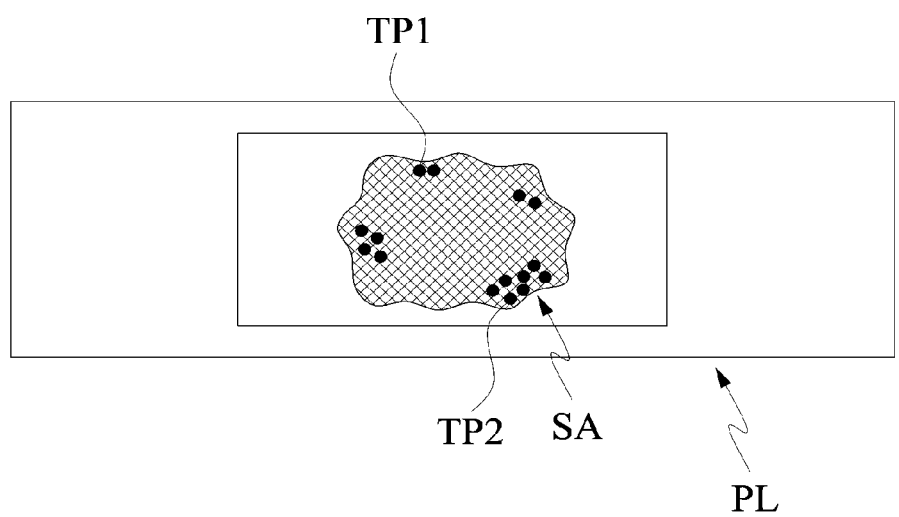
FIG. 84 illustrates a part of a case in which a plurality of target proteins are detected in an immunoassay method according to the present application.

FIGS. 83 and 84 schematically illustrate a part of a case in which multiple target proteins TP are detected in an immunoassay method according to the present application. Description with reference to the flowchart in FIG. 81 will be given below.

In immunoassay according to an embodiment of the present application, target proteins TP included in a sample may include first target proteins TP1 and second target proteins TP2. In this case, as described above with reference to FIG. 82, after the first antibodies are provided to the reaction region (S30), and the first target proteins TP1 are detected (S51), first fluorescence may be detected from fluorescence labels attached to the first antibodies bound to the first target proteins TP1 (see FIG. 83).

Also, when, as illustrated in FIG. 82, the second antibodies are provided (S40) and the second target proteins TP2 are detected (S52), second fluorescence may be detected from fluorescence labels attached to the second antibodies bound to the second target proteins TP2. In this case, when a wavelength band from which the first fluorescence is detected and a wavelength band from which the second fluorescence is detected partially overlap, the first fluorescence may be detected in an overlapping manner during detection of the second fluorescence, and this may cause detection of the second target proteins TP2 to be difficult. In such a case, the detecting of the second fluorescence may include comparing fluorescence detected from the sample after the second antibodies are provided to the reaction region and fluorescence detected from the sample before the second antibodies are provided to the reaction region, and performing detection of the second target proteins TP2.

The sequential detection of multiple target proteins TP by using fluorescent substances which are detected from overlapping wavelength bands as described above (that is, the same type of fluorescent substances) and simultaneous detection of multiple target proteins TP by using fluorescent substances which are detected from different wavelength bands (that is, different types of fluorescent substances) may not necessarily be performed independently. Therefore, the above-described embodiments may be combined and multiple target proteins TP may be detected in a single process, and this may be usefully applied in promptly diagnosing various diseases.

Hereinafter, as an embodiment of result detection in an immunoassay according to the present application, a method of counting the number of target cells included in a sample SA to be diagnosed will be described.

According to a method of counting cells according to the present embodiment, cell counting may be performed for a sample SA applied on an object having a surface-type reaction region, such as a plate PL, or for a sample SA applied and fixated on the object. According to the present embodiment, cell counting, which has been conventionally performed depending on high-performance equipment which is mostly hydrodynamically designed, may also be performed using a simplified apparatus with a reduced size.

4.3.7.1 Fundamental Embodiment

As an example of immunoassay according to the present application, a cell counting method may include fixating a sample SA on a plate PL, providing antibodies AB to the plate PL by using a patch PA that contains the antibodies AB which react specifically with target cells, and acquiring the number of target cells included in the sample SA.

The fixating of the sample SA on the plate PL may be similar to that in the above-described immunoassay methods.

The providing of the antibodies AB to the plate PL by using the patch PA that contains the antibodies AB which react specifically with the target cells may include providing the antibodies AB to the plate PL by using a patch PA that contains the antibodies AB that have a property of binding specifically to some proteins included in the target cells. In other words, the antibodies AB which specifically bind to some proteins that form the target cells may be provided to the plate PL through the patch PA.

The acquiring of the number of target cells included in the sample SA may be performed by a method of detecting fluorescence labeled on the antibodies AB. The acquiring of the number of target cells may be performed by a method of detecting a chemical reaction of a substrate SU catalyzed by enzymes attached to the antibodies AB or a product PD produced due to the chemical reaction.

The acquiring of the number of target cells included in the sample SA may be performed by acquiring an image of a region on the plate PL in which the target cells are distributed. The acquiring of the number of target cells may be performed by acquiring an image of the region in which the sample SA is distributed and detecting the target cells from the image. In other words, the acquiring of the number of target cells included in the sample SA may include acquiring only numerical information on the cells from a measured signal strength or the like or acquiring an image of a region in which the target cells are distributed or an image of the target cells.

4.3.7.2 Detection of a Plurality of Targets

In the cell counting method according to the embodiment, the counting of the number of cells may be simultaneously performed for a plurality of target cells. Here, the simultaneous performance may refer that the number of plurality of target cells may be counted using a single plate PL. Alternatively, the simultaneous performance may refer that it may be performed on a sample SA located in a single reaction region.

A patch PA may contain first antibodies AB which react specifically with first target cells and second antibodies AB which react specifically with second target cells. A first fluorescent substance may be labeled on the first antibodies AB, and a second fluorescent substance may be labeled on the second antibodies AB. In this case, fluorescence emitted from the first fluorescent substance and fluorescence emitted from the second fluorescent substance may be detected from different wavelength bands.

4.3.7.3 Method of Using a Plurality of Patches

The above-described cell counting method may be performed on a plurality of target cells by using a plurality of patches PA.

The cell counting method using the plurality of patches PA may include fixating a sample SA on a plate PL, using a first patch PA that contains first antibodies AB which react specifically with first target cells to provide the first antibodies AB to the plate PL, and using a second patch PA that contains first antibodies AB which react specifically with second target cells to provide the second antibodies AB to the plate PL The cell counting method may include, after the providing of the first antibodies AB to the plate PL and before the providing of the second antibodies AB to the plate PL, obtaining the number of the first target cells included in the sample SA.

The cell counting method may include, after the providing of the second antibodies AB to the plate PL, obtaining the number of the second target cells included in the sample SA. In other words, after the first antibodies AB are provided to the plate PL, the number of the first target cells may be obtained, and after the second antibodies AB are provided to the plate PL, the number of second target cells may be obtained.

The cell counting method may include, after the providing of the second antibodies AB to the plate PL, obtaining the number of the first target cells and the number of the second target cells included in the sample SA. In other words, the number of the first target cells and the second target cells may be obtained after the first antibodies AB and the second antibodies AB are provided to the plate PL.

The obtaining of the number of the first target cells or the number of the second target cells may be similar to the obtaining of the number of target cells included in the sample SA in the above-described embodiment of the cell counting method.

However, when cell counting is performed for a plurality of target cells by using a plurality of patches PA as in the present embodiment, a fluorescent substance labeled to the first target cells and a fluorescent substance labeled to the second target cells may be of the same type. In other words, a wavelength band from which a fluorescent substance labeled to the first target cells is detected and a wavelength band from which a fluorescent substance labeled to the second target cells is detected may partially overlap. In this case, while the number of the first target cells is obtained after the first antibodies AB are provided to the plate PL and the number of the second target cells is obtained after the second antibodies AB are provided to the plate PL, the obtaining of the number of the second target cells may be performed by comparing fluorescence detected for obtaining the number of the first target cells and fluorescence detected for obtaining the number of the second target cells.

4.3.7.4 Plurality of Patches

The cell counting method for a plurality of target cells according to the embodiment may be performed using a plurality of patches PA.

In other words, the plurality of target cells may include first target cells and second target cells, and the plurality of patches PA may include a first patch PA that contains first antibodies AB and a second patch PA that contains second antibodies AB. In this case, the first antibodies AB may bind specifically to proteins expressed specifically in first target cells, and the second antibodies AB may bind specifically to proteins expressed specifically in second target cells.

4.3.8 Immunoassay Device

Immunoassay of the present application may be performed using an immunoassay method.

Figure 78:
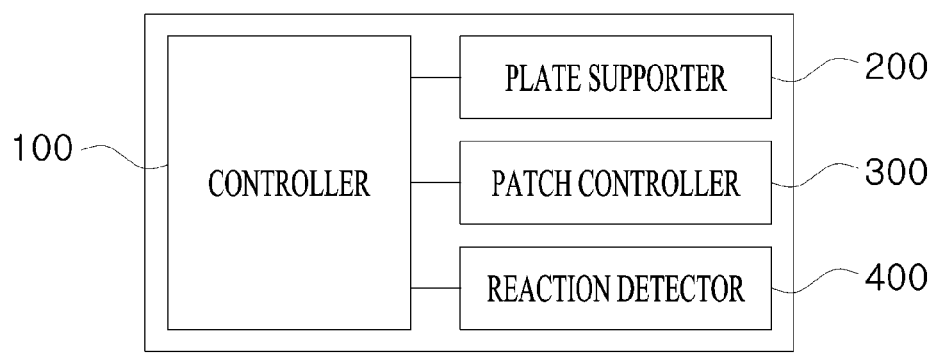
FIG. 78 illustrates an embodiment of an immunoassay device according to the present application.

FIG. 78 illustrates an immunoassay device 10 according to an embodiment of the present application The immunoassay device according to an embodiment of the present application may include a plate PL supporter 200, a patch controller 300, and a reaction detector 400. The immunoassay device according to the present embodiment may perform diagnosis by detecting target proteins TP from a sample SA to be diagnosed by using a patch which includes a mesh structural body NS forming micro-cavities and is configured to contain a liquid substance SB in the micro-cavities.

The plate PL supporter 200 of the immunoassay device may support a plate on which a reaction region is located and a sample SA to be diagnosed is located in the reaction region.

The patch controller 300 may use a patch PA that contains antibodies AB which react specifically with the target proteins TP and control a position of the patch PA relative to the reaction region so that antibodies AB are provided to the reaction region.

The reaction detector 400 may detect a specific reaction between the antibodies AB and the target proteins TP to diagnose a target disease.

Also, the immunoassay device may further include a controller 100.

The immunoassay device may include a mesh structural body NA forming micro-cavities and use a patch PA capable of containing a liquid substance SB in the micro-cavities to detect target proteins TP from a sample SA to be diagnosed and perform diagnosis.

The immunoassay device may include a plate PL supporter configured to support a plate PL on which a reaction region is located and a sample SA to be diagnosed is located in the reaction region, a patch controller configured to use a patch PA, which contains antibodies AB which react specifically with target proteins TP and control a position of the patch PA relative to the reaction region so that the antibodies AB are provided to the reaction region, and a reaction detector configured to detect a specific reaction between the antibodies AB and the target proteins TP to diagnose a target disease.

Figure 79:
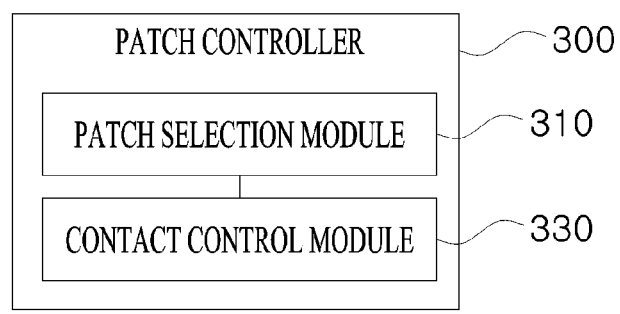
FIG. 79 illustrates an example of a patch controller in an embodiment of an immunoassay device according to the present application.
Figure 80:
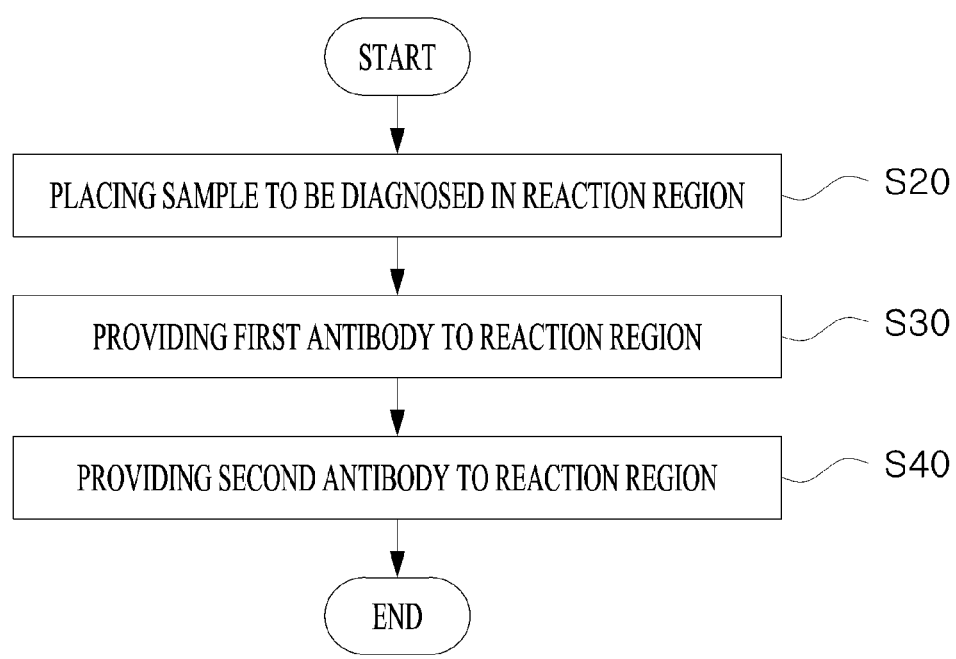
FIG. 80 illustrates a flowchart for describing an example of an immunoassay method according to the present application.

FIG. 79 illustrates an example of the patch controller 300 in an embodiment of the immunoassay device 10 according to the present application.

In the immunoassay device 10 according to an embodiment of the present application, the patch controller 300 may include a patch selection module 310 and a contact control module 330.

The patch selection module 310 may select a patch PA to be controlled. The selection of the patch PA to be controlled by the patch selector may include selecting at least one of a patch PA that contains primary antibodies AB, a patch PA that contains secondary antibodies AB, a patch PA that contains a substrate SU, a washing patch PA, or a patch cluster.

The contact control module 330 may control a state of contact between a selected patch PA and a reaction region. The controlling of the contact state may include controlling a position of the patch PA relative to the reaction region.

The reaction detector 400 may be any one of an optical detector and an electrochemical detector.

The reaction detector may include an image acquisition module. The reaction detector may include a camera module. The reaction detector may acquire partial images of a reaction region. The reaction detector may combine the acquired partial images. The reaction detector may acquire a single image of a reaction region. The reaction detector may acquire partial images of the reaction region or a single image of the reaction region, and the combining of the partial images may be performed by an image processing module.

5. Clinical Chemistry 5.1 Meaning 5.1.1 Clinical Chemistry

Although immunoassay refers to diagnosis using antigen-antibody binding, applications of a patch PA are not limited thereto, and the patch PA may also be applied in similar fields in which diagnosis is performed using a specific interaction.

Particularly, application of a patch PA may be expanded similarly to the clinical chemistry diagnostic field in which diagnosis is performed on bodily fluid as a sample SA by using a specific reaction. Clinical chemistry is one specific field of laboratory medicine and refers to performing diagnosis on bodily fluid in particular. Bodily fluid refer to liquid components collected from the human body such as blood, urine, cerebrospinal fluid (CSF), tears, and nasal mucus, and also includes pus and effusion.

The specific interaction used in the diagnosis encompasses various forms of chemical and biochemical reactions. For example, a factor which indicates a presence of disease may be detected using a diagnostic reagent, or a concentration of a specific component in the blood may be measured to determine normality. Also, for example, an enzyme-substrate reaction may be used, or an activity of enzymes may be measured.

A diagnosis result may be acquired by detecting the specific interaction. In detecting the specific interaction, colorimetric measurement, color development detection, fluorescence detection, and electrochemical detection may be usefully utilized.

5.1.2 Relationship with Immunoassay

The above-described method of performing immunoassay using a patch PA may also be performed similarly in clinical chemistry diagnosis. In other words, since clinical chemistry diagnosis may also be performed on a plate PL and performed using the patch PA, the same advantageous effects as the immunoassay may be expected.

For example, diagnosis may also be performed by applying or smearing a sample SA on the plate PL in performance of clinical chemistry diagnosis. Consequently, since an effective contact surface area is maximized, a diagnosis result with sufficient validity may be expected even with a small amount of sample SA. Also, since the clinical chemistry diagnosis may be performed using the patch PA, it is extremely easy to pour a reagent which is involved in target detection onto the plate PL on which the target detection process is performed and remove the reagent from the plate PL. Therefore, an amount of reagents used in the detection and time taken for diagnosis may be saved.

5.2 Embodiments of Clinical Chemistry

5.2.1 Hormone Detection

Clinical chemistry diagnosis according to an embodiment of the present application may be used in hormone detection.

Clinical chemistry diagnosis according to an embodiment of the present application may be performed by applying a sample SA on a plate PL, providing a reagent to the plate PL by using a patch PA, and detecting a target hormone from the sample SA.

The sample SA applied on the plate PL may be blood or urine. The applying of the sample SA on the plate PL may include applying the sample SA on the plate PL and fixating the sample SA. Some reagents that are involved in the hormone detection may be placed on the plate PL in advance.

The detecting of the target hormone may include detecting cortisol in accordance with the Porter-Silber technique. The detecting of the target hormone may include detecting any one of a follicle-stimulating hormone (FSH), an adrenocorticot-ropin hormone (ACTH), a growth hormone (GH), a thyroid-stimulating hormone (TSH), and a thyroid hormone (T4).

The detecting of the target hormone may include detecting a reaction between a target hormone present in the sample SA and a reagent provided to the sample SA. The detecting of the reaction may be performed using any one of a colorimetric technique, fluorescence detection, luminescence detection, and an electrochemical sensor.

5.2.2 Cholesterol

Clinical chemistry diagnosis according to an embodiment of the present application may be used in measuring cholesterol in the blood. In this case, an enzyme technique may be used.

Clinical chemistry diagnosis according to an embodiment of the present application may be performed by applying a sample SA on a plate PL, providing a reagent to the plate PL by using a patch PA, and measuring cholesterol content from the sample SA.

The sample SA applied on the plate PL may be serums. The applying of the sample SA on the plate PL may include applying the sample SA on the plate PL and fixating the sample SA. Some reagents used in the cholesterol detection may be placed on the plate PL in advance.

The reagent provided to the plate PL by using the patch PA may be an enzyme reagent. The enzyme reagent may include at least some of 4-aminoantipyrine (4AA), peroxidase, cholesterol esterase, and cholesterol oxidase.

The detecting of the cholesterol content may include measuring a level of light absorption.

Clinical chemistry diagnosis according to another embodiment of the present application may be performed using an enzyme technique in measuring triglyceride in the blood.

A sample SA may be applied on the plate PL, a reagent may be provided to the plate PL by using a patch PA, and a triglyceride content may be measured from the sample SA.

The sample SA applied on the plate PL may be serums. The reagent provided to the plate PL by using the patch PA may be an enzyme reagent. The enzyme reagent may include at least some of glycerol kinase, lipase, phenol, 4-aminoantipyrine, peroxidase, and pyruvate kinase.

The detecting of the cholesterol content may include measuring a level of light absorption.

5.2.3 Blood Glucose Measurement

Clinical chemistry diagnosis according to an embodiment of the present application may be used in measuring a concentration of a specific component contained in a sample SA. The specific component of which a concentration is to be measured may be blood glucose.

Clinical chemistry diagnosis according to an embodiment of the present application may be performed by applying a sample SA on a plate PL, providing a reagent to the plate PL by using a patch PA, and measuring an amount of glucose included in blood, that is, blood glucose, from a reaction due to the reagent. In this case, an enzyme technique may be used.

The sample SA applied on the plate PL may be any one of whole blood, plasmas, serums, urine, CSF, and a pleural effusion fluid. The reagent provided to the plate PL may include any one of glucose oxidase and hexokinase.

The measuring of the blood glucose may be performed by measuring a result of a pigment reaction of a reaction due to the reagent. The measuring of the blood glucose may be performed using a reflectance light intensity measurement technique or an electrochemical measurer.

The above description is merely illustrative of the technical spirit of the present disclosure, and those of ordinary skill in the art to which the present disclosure pertains should be able to make various modifications and changes within a scope not departing from essential characteristics of the present disclosure. Therefore, the above-described embodiments of the present disclosure may also be implemented separately or in combination.

The embodiments disclosed herein are for describing the technical spirit of the present disclosure instead of limiting the same, and the scope of the technical spirit of the present disclosure is not limited by such embodiments. The scope of the present disclosure should be interpreted on the basis of the claims below, and all technical spirits within the equivalent scope should be interpreted as belonging to the scope of the present disclosure.

The invention claimed is:

1. An antibody-containing patch comprising:
   antibodies that react specifically with a target protein; and
   a mesh structural body provided in a mesh structure forming micro-cavities in which the antibodies are contained that is configured to come into contact with a reaction region comprising the target protein and provide some of the contained antibodies to the reaction region, wherein the reaction region is external to the antibody-containing patch, wherein the mesh structure comprises nano-sized pores.

2. The antibody-containing patch of claim 1, wherein the antibodies that react specifically with the target protein are primary antibodies which specifically bind to a target antigen.

3. The antibody-containing patch of claim 1, wherein the antibodies that react specifically with the target protein are secondary antibodies which specifically bind to antibodies which have a property of binding specifically to a target antigen.

4. The antibody-containing patch of claim 1, wherein:
   the target protein is an antigen;
   the antibodies are a pair of antibodies formed by binding of a primary antibody which specifically binds to the antigen and a secondary antibody which specifically binds to the primary antibody; and
   the pair of antibodies react specifically with the antigen.

5. The antibody-containing patch of claim 1, wherein:
   the target protein is plural;
   the plurality of target protein include a first target protein and a second target protein; and the antibodies include a first antibody that reacts specifically with the first target protein and a second antibody that reacts specifically with the second target protein.

6. The antibody-containing patch of claim 1, further comprising a liquid substance containing the antibodies and wherein the liquid substance is formed of a single component having fluidity.

7. The antibody-containing patch of claim 6, wherein the single component is a single chemical element or a compound comprising a plurality of chemical elements.

8. The antibody-containing patch of claim 1, further comprising a liquid substance containing the antibodies and wherein the liquid substance is a mixture comprising a plurality of components.

9. The antibody-containing patch of claim 8, wherein the mixture is a solution and a portion of the plurality of components is a solvent and another portion of the plurality of components is a solution.

10. The antibody-containing patch of claim 8, wherein the mixture is a uniformly distributed substance.

11. The antibody-containing patch of claim 8, wherein the mixture is a uniformly mixed mixture.

12. The antibody-containing patch of claim 8, wherein the plurality of components are uniformly distributed and comprise (i) a solvent and (ii) a substance that is not dissolved in a solvent.

13. The antibody-containing patch of claim 1, wherein the mesh structural body is a three-dimensional mesh.

14. The antibody-containing patch of claim 1, wherein the mesh structural body is a gel-type structural body.

15. The antibody-containing patch of claim 1, wherein the mesh structural body is a continuously distributed solid structure.

16. The antibody-containing patch of claim 1, wherein the mesh structural body is a sponge structure.

17. The antibody-containing patch of claim 1, further comprising a liquid substance containing the antibodies and wherein a density of the mesh structural body is within a predetermined range based on a limit in which a form of the liquid substance is maintained as a liquid.

18. The antibody-containing patch of claim 1, wherein the antibodies are absorbed into the mesh structural body from an external medium.

* * * * *